(12) United States Patent
von Badinski et al.

(10) Patent No.: US 11,188,124 B2
(45) Date of Patent: Nov. 30, 2021

(54) WEARABLE COMPUTING DEVICE

(71) Applicant: Proxy, Inc., San Francisco, CA (US)

(72) Inventors: Curt C. von Badinski, San Francisco, CA (US); Michael J. Strasser, San Francisco, CA (US); Peter Twiss, San Francisco, CA (US)

(73) Assignee: Proxy, Inc., San Francisco, CA (US)

( * ) Notice: Subject to any disclaimer, the term of this patent is extended or adjusted under 35 U.S.C. 154(b) by 0 days.

(21) Appl. No.: 17/013,348

(22) Filed: Sep. 4, 2020

(65) Prior Publication Data
US 2020/0401183 A1 Dec. 24, 2020

Related U.S. Application Data

(60) Continuation of application No. 16/224,686, filed on Dec. 18, 2018, now Pat. No. 10,768,666, which is a
(Continued)

(51) Int. Cl.
*G06F 1/16* (2006.01)
*A61B 5/00* (2006.01)
(Continued)

(52) U.S. Cl.
CPC ........... *G06F 1/163* (2013.01); *A61B 5/01* (2013.01); *A61B 5/021* (2013.01); *A61B 5/0205* (2013.01); *A61B 5/02416* (2013.01); *A61B 5/1118* (2013.01); *A61B 5/1455* (2013.01); *A61B 5/14532* (2013.01); *A61B 5/332* (2021.01); *A61B 5/349* (2021.01); *A61B 5/681* (2013.01); *A61B 5/6826* (2013.01); *G01P 15/00* (2013.01); *G02B 19/0052* (2013.01); *G02B 19/0061* (2013.01); *G04G 21/02* (2013.01);
(Continued)

(58) Field of Classification Search
CPC ...................................................... G06F 1/163
See application file for complete search history.

(56) References Cited

U.S. PATENT DOCUMENTS 7,312,722 B2 * 12/2007 Tillotson .................. G08G 1/14
340/932.2
10,096,247 B1 * 10/2018 Sandbrook ............. G08G 1/143
(Continued)

OTHER PUBLICATIONS

European Office Action for application EP14866236.4 dated Apr. 28, 2021.

*Primary Examiner* — Travis R Hunnings

(57) ABSTRACT

A smart ring includes a curved housing having a U-shape interior storing components including: a curved battery approximately conforming to the curved housing, a semi-flexible PCB approximately conforming to the curved housing and having mounted thereon: a motion sensor for generating motion data from physical perturbations of the smart ring, a memory for storing executable instructions, a transceiver for sending data to a client computer, a temperature sensor, and a processor for receiving motion data and performing executable instructions in response thereto, and a potting material disposed in the interior, forming an interior wall of the smart ring, wherein the potting material encapsulates the components and is substantially transparent to visible light, infrared light, and/or ultraviolet light.

20 Claims, 33 Drawing Sheets

Related U.S. Application Data division of application No. 15/444,217, filed on Feb. 27, 2017, now Pat. No. 10,156,867, which is a division of application No. 14/556,062, filed on Nov. 28, 2014, now Pat. No. 9,582,034.

(60) Provisional application No. 62/006,835, filed on Jun. 2, 2014, provisional application No. 61/910,201, filed on Nov. 29, 2013.

(51) Int. Cl.

| | |
|---|---|
| H02J 7/35 | (2006.01) |
| A61B 5/332 | (2021.01) |
| A61B 5/349 | (2021.01) |
| G01P 15/00 | (2006.01) |
| G04G 21/02 | (2010.01) |
| G06F 3/01 | (2006.01) |
| G06K 9/00 | (2006.01) |
| G08B 21/02 | (2006.01) |
| G08C 17/02 | (2006.01) |
| G06F 3/14 | (2006.01) |
| G08B 5/36 | (2006.01) |
| H02J 7/00 | (2006.01) |
| H02S 40/22 | (2014.01) |
| G02B 19/00 | (2006.01) |
| H02S 99/00 | (2014.01) |
| A61B 5/01 | (2006.01) |
| A61B 5/021 | (2006.01) |
| A61B 5/024 | (2006.01) |
| A61B 5/11 | (2006.01) |
| A61B 5/145 | (2006.01) |
| A61B 5/1455 | (2006.01) |
| G06F 21/32 | (2013.01) |
| G06K 9/62 | (2006.01) |
| A61B 5/0205 | (2006.01) |

(52) U.S. Cl.
CPC ......... *G04G 21/025* (2013.01); *G06F 1/1635* (2013.01); *G06F 3/014* (2013.01); *G06F 3/017* (2013.01); *G06F 3/14* (2013.01); *G06F 21/32* (2013.01); *G06K 9/00885* (2013.01); *G06K 9/00892* (2013.01); *G06K 9/6202* (2013.01); *G08B 5/36* (2013.01); *G08B 21/02* (2013.01); *G08C 17/02* (2013.01); *H02J 7/0044* (2013.01); *H02J 7/0047* (2013.01); *H02J 7/35* (2013.01); *H02S 40/22* (2014.12); *H02S 99/00* (2013.01); *A61B 2560/0214* (2013.01); *A61B 2560/0412* (2013.01); *A61B 2562/146* (2013.01); *A61B 2562/164* (2013.01); *A61B 2562/166* (2013.01); *G02B 19/0042* (2013.01); *G06K 2009/00939* (2013.01); *G08C 2201/30* (2013.01); *Y02E 10/52* (2013.01)

(56) References Cited

U.S. PATENT DOCUMENTS

| | | | |
|---|---|---|---|
| 10,373,493 B1 * | 8/2019 | Sandbrook | G08G 1/04 |
| 10,510,250 B2 * | 12/2019 | Sandbrook | G08G 1/04 |
| 10,748,424 B2 * | 8/2020 | Sandbrook | G08G 1/04 |
| 2006/0212344 A1 * | 9/2006 | Marcus | G07B 15/02 |
| | | | 705/13 |
| 2006/0250278 A1 * | 11/2006 | Tillotson | G08G 1/14 |
| | | | 340/932.2 |
| 2012/0293107 A1 | 11/2012 | Ajagbe | |
| 2013/0226486 A1 | 8/2013 | Henderson et al. | |
| 2015/0277559 A1 * | 10/2015 | Vescovi | G06F 1/163 |
| | | | 345/173 |
| 2017/0024619 A1 * | 1/2017 | Wu | G06T 5/00 |
| 2017/0039852 A1 * | 2/2017 | Nordbruch | B64C 39/024 |
| 2017/0236417 A1 * | 8/2017 | Carrara | G08G 1/147 |
| | | | 340/932.2 |

\* cited by examiner

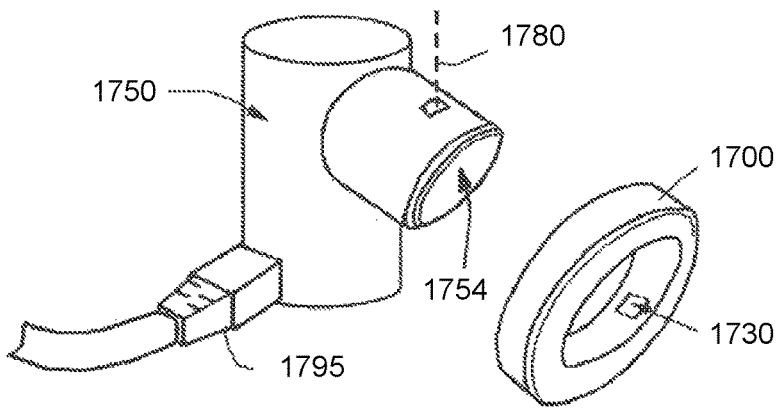
FIG. 15
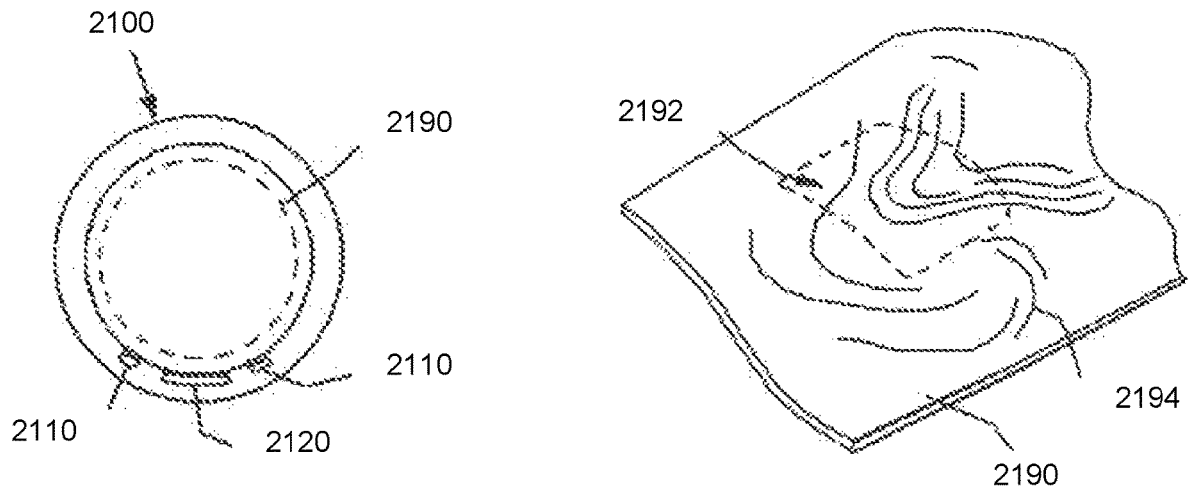
FIG. 16A
FIG. 16B
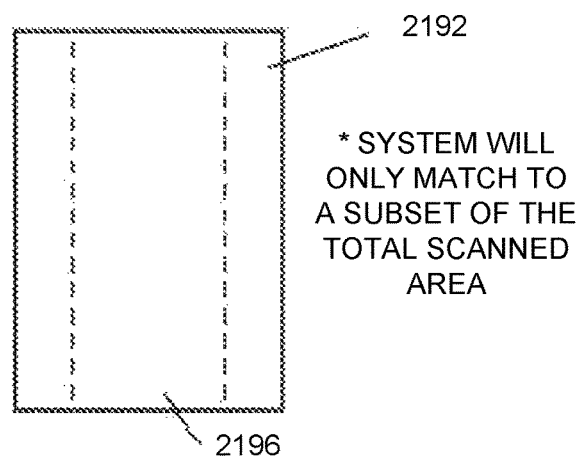
FIG. 16C

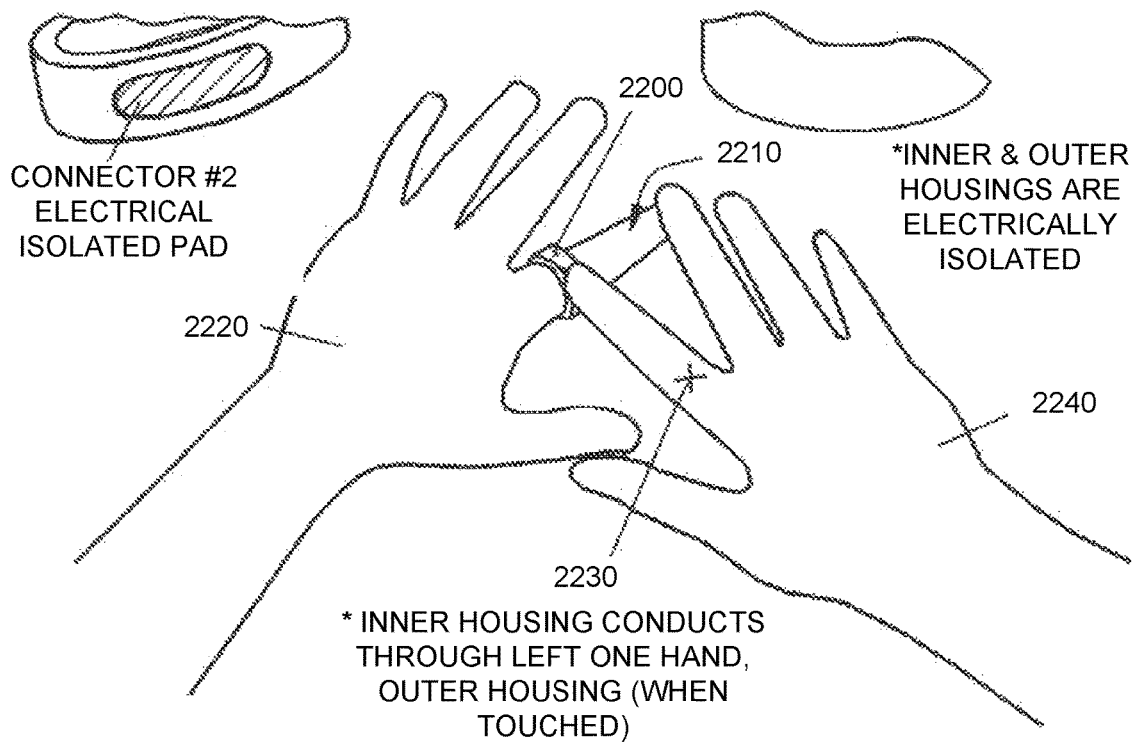
FIG. 17A
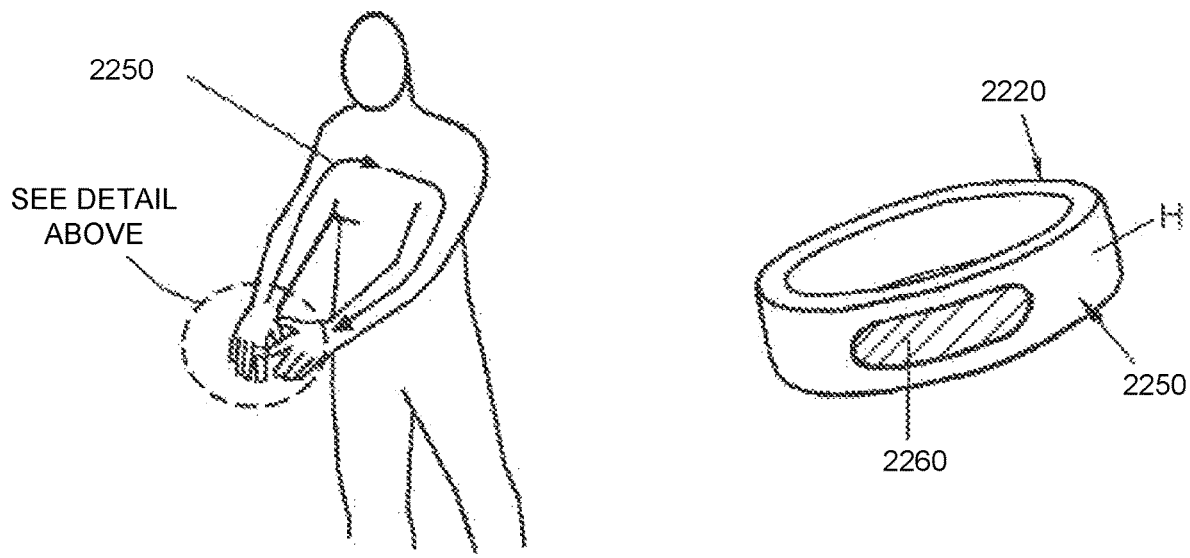
FIG. 17B
FIG. 17C

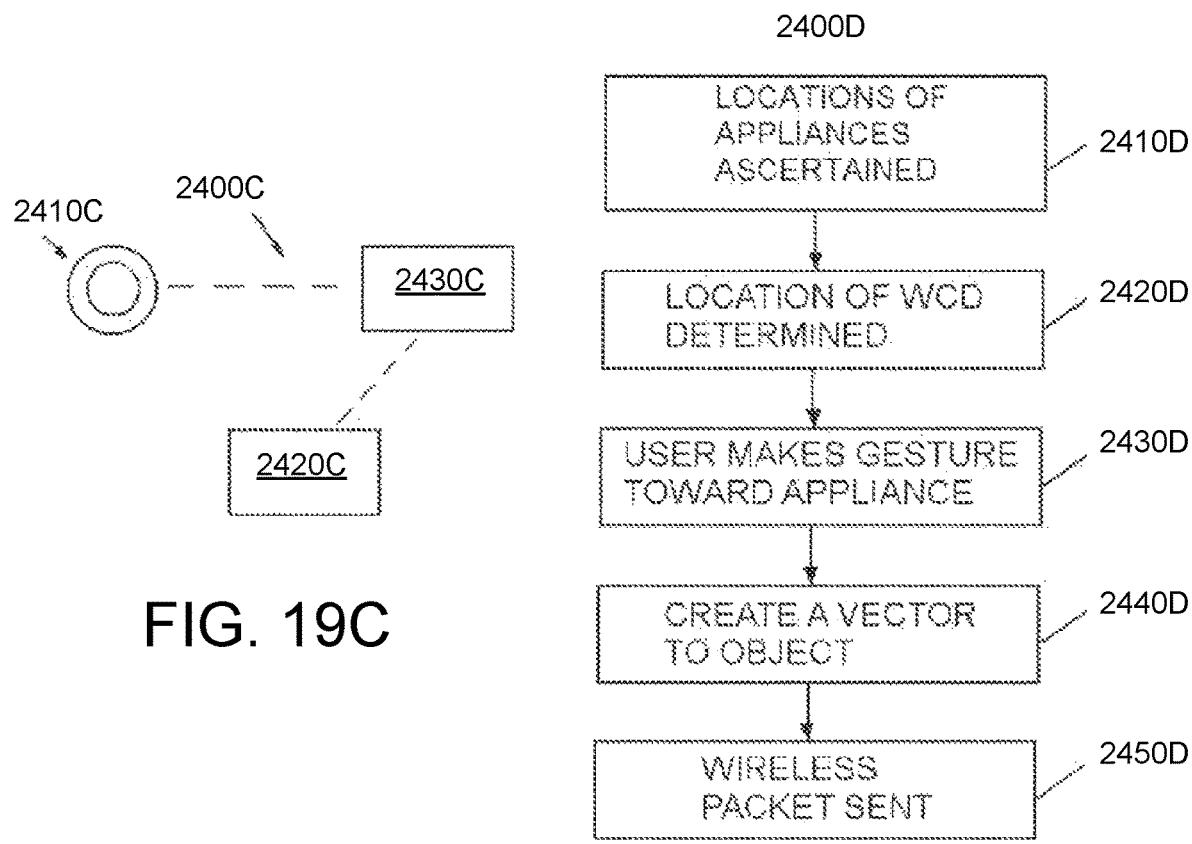
FIG. 19C
FIG. 19D
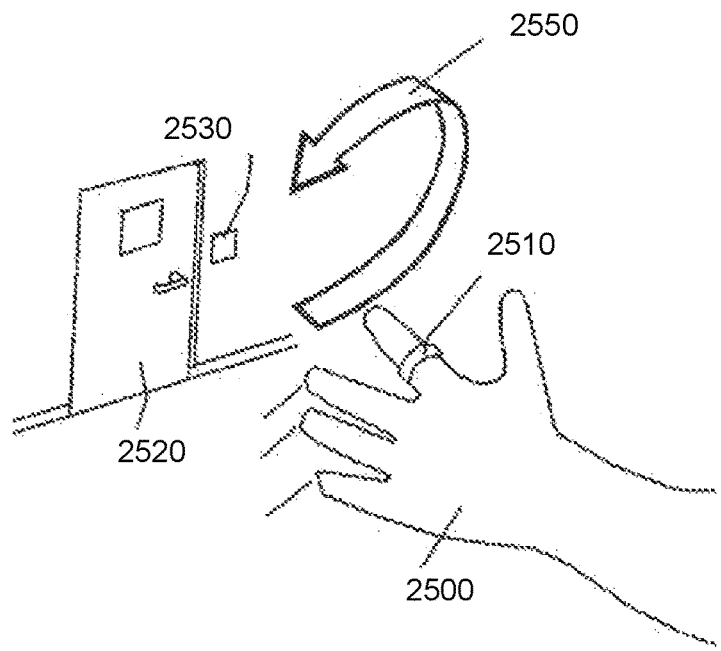
FIG. 20

WEARABLE COMPUTING DEVICE

CROSS-REFERENCE TO RELATED APPLICATIONS

This application is a continuation of Ser. No. 16/224,686, filed Dec. 18, 2018, now U.S. Pat. No. 10,768,666 issued Sep. 8, 2020 which is a divisional of U.S. patent application Ser. No. 15/444,217, filed Feb. 27, 2017, now U.S. Pat. No. 10,156,867 issued Dec. 18, 2018, which claims the benefit of U.S. patent application Ser. No. 14/556,062, filed Nov. 28, 2014, now U.S. Pat. No. 9,582,034 issued Feb. 28, 2017, and U.S. Provisional Application Ser. No. 62/006,835, filed Jun. 2, 2014, entitled WEARABLE COMPUTING DEVICE and U.S. Provisional Application Ser. No. 61/910,201, filed Nov. 29, 2013, entitled FINGER RING DEVICE FOR ACTIVITY MONITORING OR GESTURAL INPUT. The disclosures of each of the above applications are herein incorporated by reference for all purposes.

FIELD OF THE INVENTION

This invention is in the field of wearable electronic devices.

BACKGROUND OF THE INVENTION

Wearable electronics are an emerging technology with many applications for the wearer. They can improve lifestyles, ease access to technology and help monitor activity within the wearer's body. However, many current wearable electronics are bulky and can be intrusive or interfere with a person's daily life. In this regard, the wearer may not be comfortable wearing the device for extended periods of time.

SUMMARY OF THE INVENTION

This invention overcomes the disadvantages of the prior art by providing a wearable computing device (WCD) in the shape of a ring. The wearable computing device can be worn for extended periods of time and can take many measurements and perform various functions because of its form factor and position on the finger of a user.

One aspect of the disclosure provides a wearable computing device, comprising: an interior wall; an exterior wall; a flexible printed circuit board disposed between the interior wall and the exterior wall; at least one component disposed on the flexible printed circuit board; and wherein at least one of the interior wall and the exterior wall defines a window that facilitates at least one of data transmission, battery recharge, and status indication.

In one example, the window comprises an internal window defined by the interior wall.

In one example, the window comprises an exterior window defined by the exterior wall.

In one example, the window comprises a plurality of exterior windows defined by the exterior wall.

In one example, the plurality of exterior windows comprises a first exterior window and a second exterior window, wherein the first exterior window facilities battery charging and the second exterior window facilities data transmission.

In one example, at least one concentrated photovoltaic cell, an antenna, and at least one LED are accessible via the window.

Another aspect of the disclosure provides a wearable computing device, comprising: an internal housing portion configured to be disposed near a finger of a user; a flexible printed circuit board arranged around a portion of a circumference of an interior surface of the internal housing; at least one component disposed on the flexible printed circuit board; and an external housing portion configured to seal the at least one component and the printed circuit board in an internal space defined by the interior surface of the internal housing.

In one example, the external housing portion comprises a substantially transparent external potting.

In one example, the at least one component comprises at least one LED configured to emit at least one of visible light, infrared radiation, and ultraviolet radiation through the external potting.

In one example, the at least one component comprises a concentrated photovoltaic cell configured to receive concentrated light through the transparent external potting.

In one example, the flexible printed circuit board includes a plurality of stiffener elements configured to engage with a corresponding plurality of flanges disposed on the internal housing portion.

Another aspect of the disclosure provides a wearable computing device, comprising: an external housing portion; a flexible printed circuit board arranged around a portion of a circumference of an interior surface of the external housing; at least one component disposed on the flexible printed circuit board; and an internal housing portion configured to seal the at least one component and the printed circuit board in an internal space defined by the interior surface of the external housing.

In one example, the internal housing portion comprises a substantially transparent internal potting.

In one example, the at least one component comprises at least one LED configured to emit at least one of visible light, infrared radiation, and ultraviolet radiation through the internal potting.

In one example, the at least one component comprises a concentrated photovoltaic cell configured to receive concentrated light through the transparent internal potting.

In one example, the flexible printed circuit board includes a plurality of stiffener elements configured to engage with a corresponding plurality of flanges disposed on the external liaising portion.

Another aspect of the disclosure provides a system, comprising: a wearable computing device, including a housing and a photovoltaic element disposed at least partially within the housing; and a base assembly, the base assembly including a concentrated light source directed at the photovoltaic element.

In one example, the wearable computing device includes at least one ferrous element disposed within the housing, and wherein the base assembly includes at least one magnetic element disposed therein.

In one example, the concentrated light source is arranged circumferentially around the wearable computing device when the wearable computing device is engaged with the base assembly.

In one example, the concentrated light source comprises at least one of a laser diode and a light emitting diode (LED).

In one example, a housing of the WCD defines an opening through which the WCD is configured to receive concentrated light.

In one example, the base assembly comprises an optical element for focusing concentrated light emitted from the concentrated light source.

In one example, the optical element comprises a lens and is selected from the group consisting of concave, convex, plano-concave, plano-convex.

In one example, the WCD comprises at least one transparent potting configured to allow concentrated light to pass therethrough.

In one example, the WCD is ring-shaped and the base assembly comprises at least one post configured to engaged with a finger space of the WCD.

In one example, the photovoltaic cell comprises a plurality of photovoltaic cells.

Another aspect of the disclosure provides an enclosure for a wearable computing device, the enclosure comprising: a base defining a receptacle for receiving the wearable computing; a lid configured to engage with the base to substantially enclose the wearable computing device, the lid having an optical element configured to direct incident electromagnetic radiation to a photovoltaic cell disposed on the wearable computing device to allow charging thereof.

In one example, the lid includes a plurality of vent holes that prevent overheating within the enclosure.

In one example, the optical element comprises a lens.

In one example, the lens has a focal length and wherein a distance between a central portion of the lens and the photovoltaic cell is greater than or less than the focal length.

Another aspect of the disclosure provides a timepiece system, comprising: a timepiece having a substantially planar under surface; and a timepiece computing device adhered to the planar under surface, the timepiece computing device being substantially cylindrical and comprising: a processor; a memory; and at least one sensor.

Another aspect of the disclosure provides a wearable computing device system, comprising: a wearable computing device; an attachment frame coupled to the wearable computing device; and an optical element removably coupled to the attachment frame, wherein the optical element is configured to direct electromagnetic radiation to a photovoltaic cell disposed on a surface of the wearable computing device to allow for charging of the wearable computing device.

In one example, the attachment frame is removably coupled to the wearable computing device.

In one example, the attachment frame engages with an inward-facing surface of the wearable computing device.

Another aspect of the disclosure provides a method of identifying an authorized user of a wearable computing device, comprising: illuminating a portion of a skin surface of the user; imaging the portion of the skin surface of the user to generate at least one first image; generating a reference capillary map corresponding to the user based at least in part on the at least one image.

In one example, the method further includes rotating the wearable computing device during the illuminating and imaging steps.

In one example, the method further includes imaging the portion of the skin surface of the user to generate at least one second image; and comparing the at least one second image to the reference capillary map in order to authenticate the user.

Another aspect of the disclosure provides a method of navigating, comprising: gesturing in a first direction while wearing a wearable computing device; comparing the first direction to a predetermined direction in a predetermined set of directions; providing feedback based on the comparison of the first direction of the predetermined direction.

In one example, the gesture comprises pointing a finger and the first direction comprises a first heading.

Another aspect of the disclosure provides a method of regulating temperature, comprising: measuring a skin temperature of a user via a first temperature sensor; measuring an ambient temperature via a second temperature sensor; comparing the skin temperature to a predetermined threshold temperature; and adjusting the ambient temperature based in part on the comparison.

In one example, measuring the skin temperature comprises measuring the skin temperature via a first temperature sensor disposed at an inward facing surface of a wearable computing device.

In one example, measuring the ambient temperature comprises measuring the ambient temperature via a second temperature sensor disposed at an outward facing surface of the wearable computing device.

Another aspect of the disclosure provides a method for controlling appliances, comprising: identifying a position of a first appliance in a room; gesturing a first gesture in a direction of the first appliance; identifying the direction of the first direction via a wearable computing device; issuing a controlling command to the first appliance based in part on the identified direction of the gesture.

Another aspect of the disclosure provides a method of generating an alert, comprising: authenticating a first wearer of a first wearable computing device as a first authenticated user; transmitting first biometric data associated with the first wearer; associating the first biometric data with a first profile associated with the first wearer of the first wearable computing device; comparing the first biometric data with a group profile comprising aggregated biometric data from a plurality of distinct wearers of a plurality of distinct wearable computing devices; and generating an alert if the first biometric data falls outside of a predetermined threshold set by the aggregated biometric data.

In one example, the biometric data comprises at least one of heart rate; ECG profile; blood sugar, and blood pressure.

In one example, the plurality of distinct wearers share a common trait, resulting in their aggregation into the group profile.

In one example, the common trait comprises at least one of: age, gender, profession, and location.

Another aspect of the disclosure provides a method of determine a sampling rate of a wearable computing device, comprising: determining an activity level of a wearer of a wearable computing device based at least in part on data from at least one sensor disposed onboard the wearable computing device; comparing the activity level to a predetermined activity threshold; and increasing a first sensor sampling rate if the activity level is above a predetermined activity threshold.

In one example, the method further includes decreasing the first sensor sampling rate if the activity level is below a predetermined activity threshold.

In one example, the predetermined activity threshold comprises an acceleration measurement.

BRIEF DESCRIPTION OF THE DRAWINGS

The invention description below refers to the accompanying drawings, of which:

FIG. 15 is a perspective view of a base assembly and WCD according to one or more aspects of the disclosure;

FIG. 16A is a schematic view of a WCD showing components used for identifying the wearer of the WCD;

FIGS. 16B-C are perspective views of a skin surface according to one or more aspects of the disclosure;

FIGS. 17A-C are perspective views according to one or more aspects of the disclosure;

FIGS. 19A-D are various embodiments for controlling environments of a user according to one or more aspects of the disclosure;

FIG. 20 is a perspective view of the hand of a user employing a two-factor authentication technique according to one or more aspects of the disclosure;

DETAILED DESCRIPTION

The present disclosure describes a wearable computing device (WCD) that enables a wearable fitness monitor(s)/computer(s) which is suitable for prolonged usage with accurate results. The WCD can be in the form of a ring that can be worn on the finger of a human (or animal) user. Although the WCD of the present disclosure is depicted as a ring that can be worn on the finger of a user, other shapes, designs, and form factors can be utilized for the WCD. For example, the WCD can be in the form of a wrist band, bracelet, necklace, earring, or any other type of wearable accessory. In this regard, references to the finger of a user in the present application can be considered to apply to other portions of a human body depending on the form of the WCD, such as wrist, neck, ear, etc.

The term "coupled" as used herein means connected directly to or connected through one or more intervening components or circuits. Any of the signals provided over various buses described herein may be time-multiplexed with other signals and provided over one or more common buses. Additionally, the interconnection between circuit elements or software blocks may be shown as buses or as single signal lines. Each of the buses may alternatively be a single signal line, and each of the single signal lines may alternatively be buses, and a single line or bus might represent any one or more of a myriad of physical or logical mechanisms for communication (e.g., a network) between components. The present embodiments are not to be construed as limited to specific examples described herein but rather to include within their scope all embodiments defined by the appended claims.

Figure 1A:
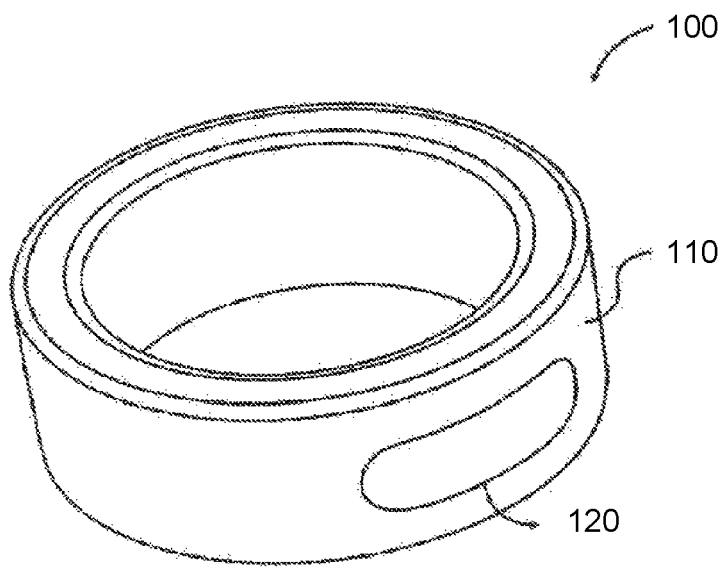
FIGS. 1A-C are perspective views of a WCD in accordance with some embodiments.
Figure 1B:
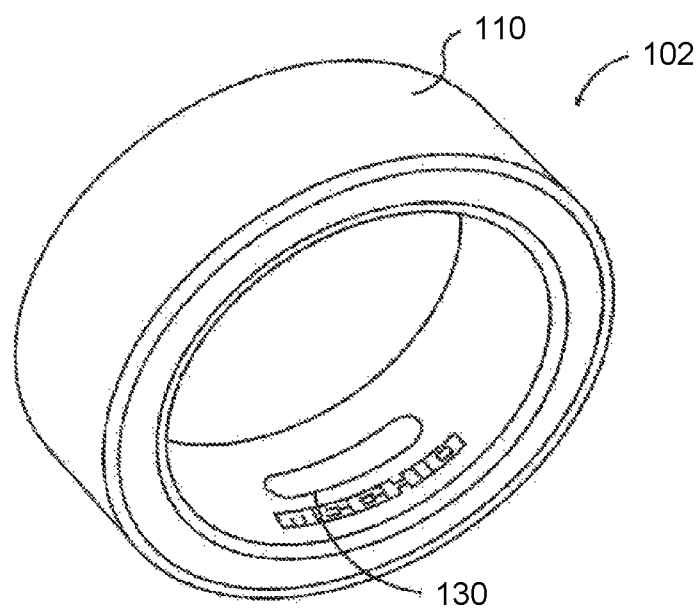

FIG. 1A is a perspective view 100 of a WCD 110 illustrating an exterior window 120 in accordance with some embodiments, and FIG. 1B is a perspective view 102 of the WCD 110 of FIG. 1A illustrating an interior window 130.

As previously mentioned, it is recognized in the present disclosure that conventional wearable fitness monitors such as clip-on devices, wristbands, or watch-pipe monitors still often suffer from inaccuracy mainly because they lack constant and consistent ways to read from the body areas they aim to monitor. It can also be an extra burden for the person to remember and wear such conventional fitness monitors each time the person perform exercises in order to create an accurate history tracking the exercise activities.

Accordingly, the present embodiments of the WCD 110 can function as fitness monitors/computer which is suitable for prolonged usage so as to create accurate results. In addition or as an alternative to fitness monitoring, as will be discussed in more detail below, the WCD 110 can function as a remote input device through, for example, gesture recognition. In some embodiments, the WCD 110 can further function as a sleep monitor, a heart rate sensor, a cardiac monitor a body temperature detector, or the like. It is noted that, for those embodiments which can function as a cardiac monitor (e.g., that measures electrocardiogram (EKG)), it may be necessary to establish a closed loop (e.g., for the electrical measurement of EKG) across the heart. As such, in some of those embodiments, a separate conductive pad can be coupled to the WCD 110 so that a user can pinch the pad with fingers on an opposite hand.

Specifically, in some embodiments of the present disclosure, the WCD 110 can be worn by the user (e.g., on a finger) for fitness, physical activity, biological data monitoring as well as for gestural input or other suitable purposes. As shown in FIGS. 1A and 1B, the WCD 110 can include the exterior window 120 on its exterior wall for input/output data transmission and reception, battery recharge, or status indication. The WCD 110 can also include the interior window 130 on its interior wall for various monitoring or sensing activities. The form factor of the WCD 110 allows it to be worn for prolonged hours with constant and consistent contact with the skin area, thereby creating a more reliable and extended recording (e.g., as compared to aforementioned conventional fitness monitors) of the user's fitness activity, physical exercise, as well as health information such as heart rates and body temperature. More implementation details regarding the WCD 110 are discussed below.

Figure 1C:
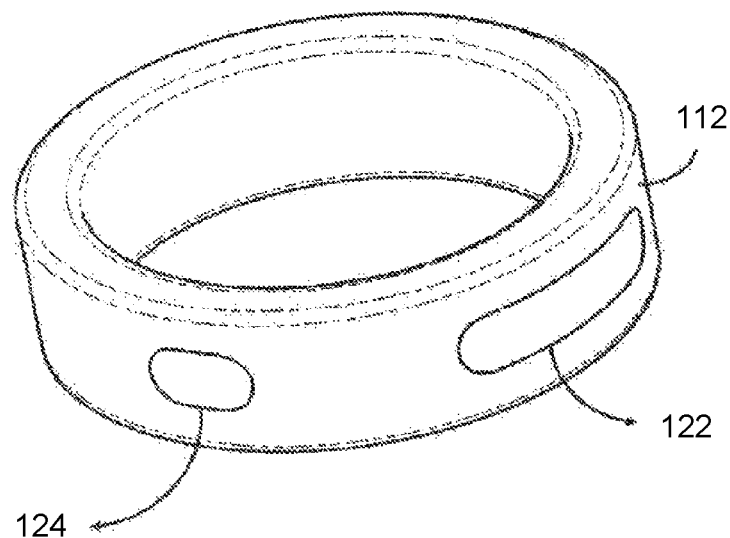

FIG. 1C is a perspective view of an alternative WCD design 112 of the WCD 110 of FIG. 1A in accordance with some embodiments. As shown in FIG. 1C, the WCD 112 includes a second exterior window 124 in addition to a first exterior window 122. The two exterior windows 122 and 124 can include spacing between the two windows 122 and 124 so that the mechanical strength of the housing structure of the WCD 112 may be stronger than that of the WCD 110, which is shown to include one single exterior window 120. Further, in some embodiments, radio antennas (e.g., Bluetooth) or other sensitive circuitry can be positioned in the second exterior window 124 away from the first exterior window 122 so that quality of reception may be improved.

Figure 2:
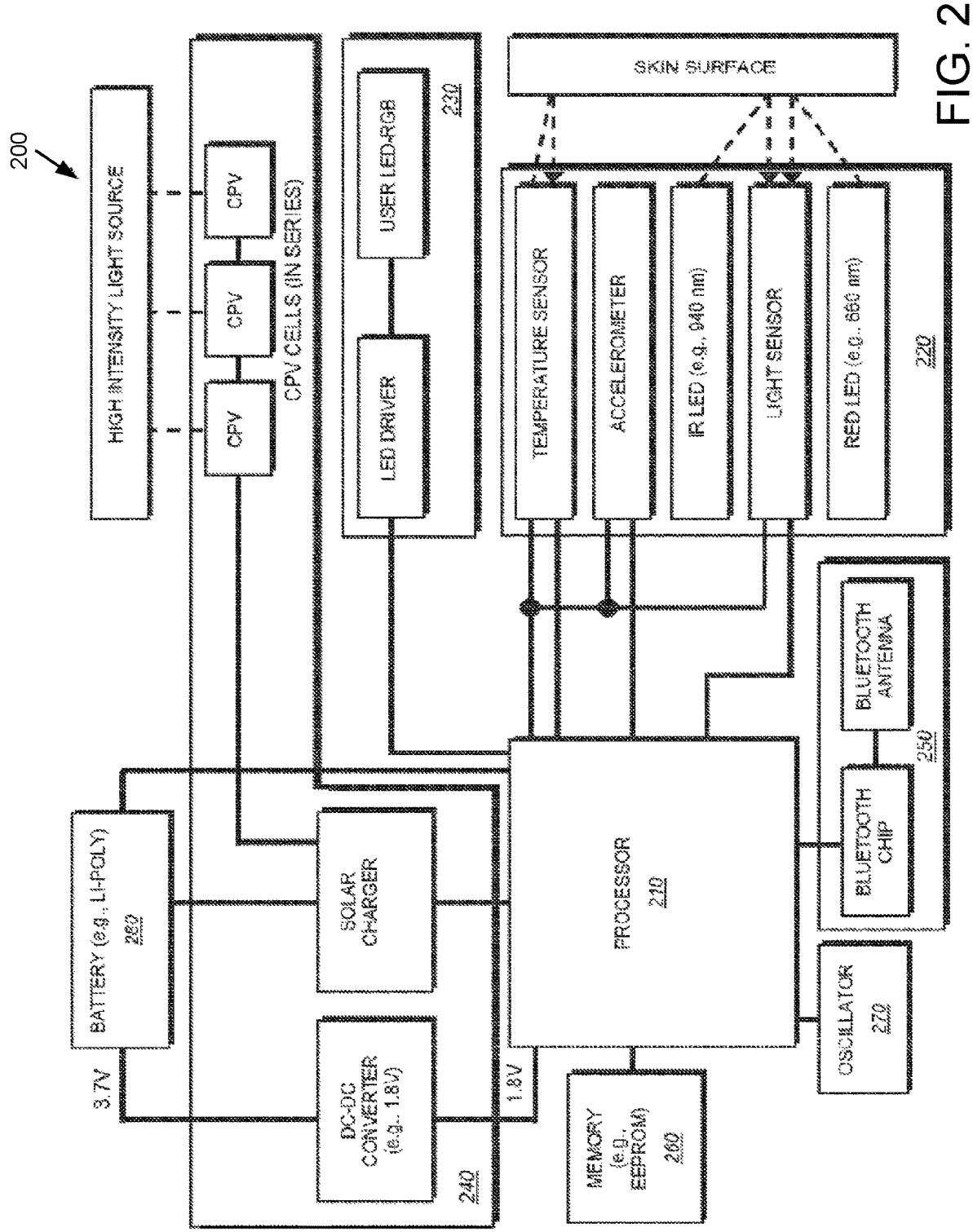
FIG. 2 is an abstract functional diagram illustrating example components within the WCD in accordance with some embodiments.

FIG. 2 is an abstract functional diagram 200 illustrating example components within the WCD (e.g., WCD 110) in accordance with some embodiments. As shown in diagram 200, the WCD 110 can include a processor module 210, a plurality of sensor modules 220, a status indicator module 230, a power generation and management module 240, a communication module 250, a memory 260, and miscellaneous modules 270 (e.g., a real-time clock (RTC) crystal oscillator as illustrated in FIG. 2). The WCD 110 can also include a battery module 280 that provides electrical power for the WCD 110. In some embodiments, the battery 280 can be of a lithium-polymer type or a zinc-polymer type. It is noted that modules illustrated in diagram 200 are for purposes of facilitating a better understanding of the present embodiments; other suitable modules may be included in the WCD 110 and are not shown for simplicity. As used herein, the term "components" is considered to generally include any of the modules depicted and/or described in FIG. 2, as well as any other modules described herein.

It is noted that the aforementioned modules are intended for purposes of enabling the present embodiments, rather than limiting. As such, a person of ordinary skill in the art will understand that the present disclosure covers apparent alternatives, modifications, and equivalents (e.g., combining or separating the modules) made to the techniques described herein. For example, in some embodiments, a portion of the communication module 250 (e.g., the Bluetooth Chip as shown in FIG. 2) can be combined into the processor module 210. For another example, one or more modules herein can be combined into one to form a system-on-the-chip (SOC).

The processor module 210 can have generic characteristics similar to general purpose processors or may be application specific integrated circuitry that provides arithmetic and control functions to the WCD 110. The processor can be any type of processor, such as a processor manufactured by Atmel, Freescale, Nordic Semiconductor, Intel®, AMD®, or an ARM® type processor. The processor module 210 can include a dedicated cache memory (not shown for simplicity). The processor module 210 is coupled to all modules 220-270 in the WCD 110, either directly or indirectly, for data and control signal transmission.

The memory 260 may include any suitable type of storage device including, for example, ROM, such as Mask ROM, PROM, EPROM, EEPROM; NVRAM such as Flash memory; Early stage NVRAM, such as nvSRAM, FeRAM, MRAM, or PRAM, or any other type, such as, CBRAM, SONOS, RRAM, Racetrack memory, NRAM, Millipede memory, or FJG. Other types of data memory can be employed as such are available in the form factor desired.

In addition to storing instructions which can be executed by the processor module 210, the memory 260 can also store data generated from the processor module 210. It is noted that the memory 260 can be an abstract representation of a generic storage environment. According to some embodiments, the memory 260 may be comprised of one or more actual memory chips or modules. In some embodiments, the memory 260 can function as a temporary storage (e.g., for firmware updates, and/or for avoiding accidental malfunctions (such as so-called "bricking")).

Figure 3A:
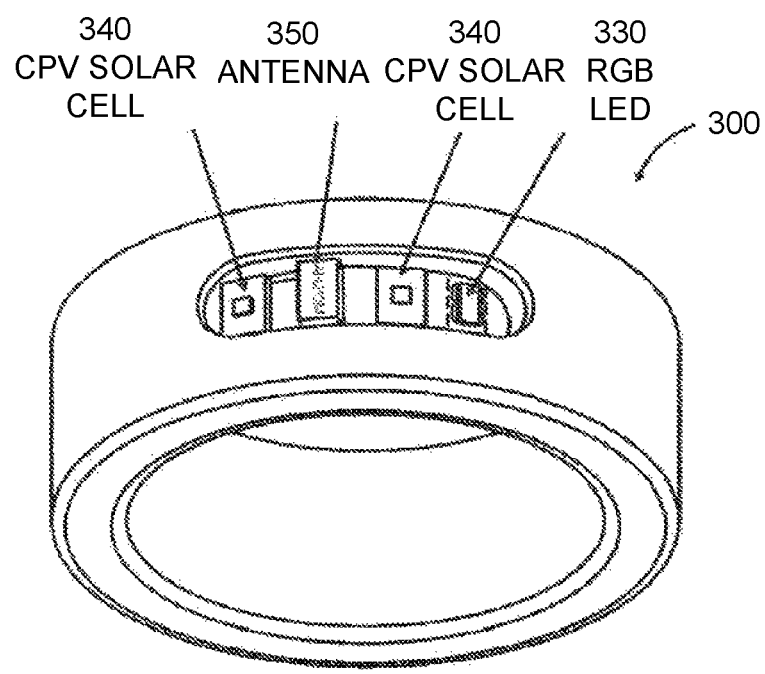
FIGS. 3A-C are views of windows of a WCD with example components exposed in accordance with some embodiments.
Figure 3B:
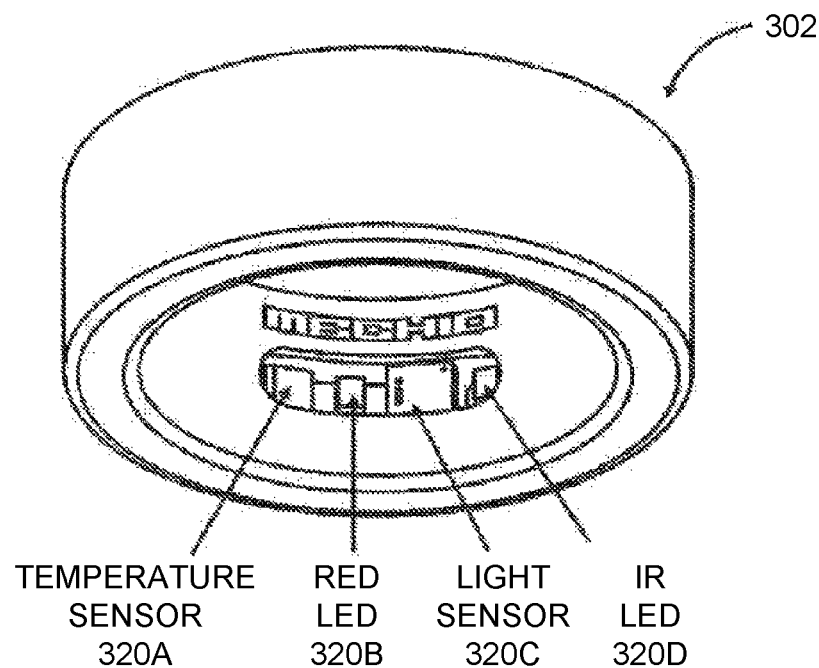

In accordance with one or more embodiments, the sensor modules 220 can include various sub-modules for the WCD 110 to perform different monitoring or sensing activities. A view 302 of the interior window (e.g., window 130) of a WCD (e.g., WCD 110) with example components exposed is shown in FIG. 3B. As shown in the example of FIG. 3B, the sensor modules 220 can include a temperature sensor 320a, a red light emitting diode (LED) 320b, a light sensor 320c, and an infra-red LED 320d. Among the sensors in the sensor modules 220, those sensors (e.g., sensors 320a-320d) which are directly related to biological sign monitoring can be configured and positioned in a way that is close to the skin (e.g., facing the interior window 130 of the WCD 110). Although not shown in FIG. 3B for simplicity, the sensor modules 220 can further include sensors that are not directly related to biological sign monitoring; some examples of these sensors include accelerometers, gyroscopes, vibration, sensors (e.g., a magnetometer or a digital compass), or other suitable sensors (e.g., for gesture recognition). The magnetometer can measure the strength and/or direction of a prevailing magnetic field. In this regard, the magnetometer can be used during global positioning and/or navigation. In particular, the magnetometer can be used to measure a directional heading when the WCD is in motion and can supplement position data where the WCD is out of communication range. In one or more embodiments, the accelerometers in the sensor modules 220 can detect movements in multiple (e.g., 3) dimensions or axes. The accelerometer can measure force of acceleration of the WCD and can measure gestures performed by a user while wearing the WCD. In other examples, the accelerometer can detect acceleration of the user while wearing the WCD. This can permit tracking of activity level, such as steps taken or number of laps swum in a pool.

The temperature sensor can be any type of sensor that detects temperature, such as a thermistor, PTC, NTC, etc. In another example, the temperature sensor can use IR light emitted from an object to calculate a surface temperature of the object in a manner clear to those of ordinary skill in the art.

Together, the processor module 210 and the sensor modules 220 can enable the WCD 110 to perform multiple functions including, for example, pedometer, sleep monitor (e.g., which monitors sleep quality), heart rate sensor, pulse oximetry, skin (and in select embodiments, ambient) temperature. In addition, some embodiments of the WCD 110 can further function as a gesture input device. In particular, the present embodiments recognize that the WCD 110 can detect finger motions or gestures which may be difficult for conventional fitness sensors to detect, such as a tap, a snap, a knock on the table, and the like. In some embodiments, the WCD 110 can utilize the accelerometer to measure the activity level (e.g., arm movement) in conjunction with the measured heart rate to determine if the user is walking horizontally, running, swimming, or climbing stairs. Other activities can be identified by the WCD 110 may include biking or sleeping.

In some embodiments, the WCD 110 can also be programmed to learn particular gestures or physical exercise from the user using, for example, a training mode. For example, the user can instruct (e.g., using a computer or a mobile device of the user) the WCD 110 to enter the training mode and perform the gesture or physical exercise; the WCD 110 can record the readings from the sensor modules 220, recognize patterns therefrom, and store the result in, for example the memory 260, so that such gesture or exercise can be recognized by the WCD 110 after the training. The WCD 110 can be configured (e.g., via a mobile application running on a mobile device of the user) so that the recognized gestures can perform functions designated by the user, such as clicks, swipes, unlocks, or media player controls. In one embodiment, the WCD 110 can include near field communication (NFC) chips so that certain functions (e.g., unlocking a smart phone) can be performed when the WCD 110 touches upon or otherwise be detected by another NFC device. In some embodiments, the unlocking function of the WCD 110 can also unlock a user device (e.g., a phone) via the communication module 250 (e.g., Bluetooth) by the WCD 110 transmitting a proper unlock code.

Moreover, the WCD 110 can function as a key or a control device for keyless access to home, automobile, or other suitable user authentication processes. The WCD 110 can also be integrated with games and game consoles so that it can function as an input device to those games and consoles. In some embodiments, the WCD 110 can be adapted for use in medical and home health monitoring, or as a transportation safety device (e.g., that broadcasts emergency messages to relevant authorities). Additional examples of sensors/functionalities of the WCD 110 can include an inertial measurement unit (IMU) (e.g., for more complex gesture recognition, a near-infrared (NIR) spectrometer (e.g., for measuring light absorption and deriving blood glucose/blood alcohol/CO2 content), a Galvanic skin response sensor (e.g., for measuring sweat/nervousness), an electrocardiogram (ECG or EKG), and so forth.

In some embodiments, the processor module 210 can determine (e.g., based on identified physical activities, routine pattern, and/or time) a frequency at which one or more sensors in the sensor modules 220 should operate. Because it is recognized in the present disclosure that the heart rate of a human being typically does not vary too widely (e.g., beyond a certain percentage of what has been previously measured), in some embodiments, the WCD 110 can automatically adjust the sensor modules 220 (e.g., to slow down) so as to save power. More specifically, some embodiments of the WCD 110 can include a phase-locked loop or logic to predict the pulse width by determining lower and upper ranges in which the heart rate is predicted to be, thus only powering up the sensor modules 220 at the time of the predicted heartbeats. For one example, if the WCD 110 determines that the user is at sleep (e.g., based on the heart rate, the body temperature, together with the movements detected by the accelerometer and/or the vibration detector), the WCD 110 can slow down its heart rate detection frequency (e.g., from 1 measurement per second to 1 measurement per 10 seconds) and skip the measurement of several heartbeats because it is unlikely that the heart rate will change drastically during that period. Conversely, if the WCD 110 determines that the user is performing a high intensity physical exercise, the WCD 110 can increase the frequency of monitoring and recording of the sensor modules 220.

In accordance with one or more embodiments, the WCD 110 also includes various modules coupled to the processor module 210 for, by way of example but not limitation, input/output data transmission, battery recharge, or status indication. A view 300 of the exterior window (e.g., window 120) of a WCD (e.g., WCD 110) with example components exposed is shown in FIG. 3A. As shown in the example of FIG. 3A, the modules configured to face the exterior window 120 of the WCD 110 can include parts from the status indicator module 230, the power generation and management module 240, and the communication module 250.

Specifically, one embodiment of the WCD 110 includes the status indicator module 230 coupled to the processor module 210 to indicate various statuses. In some embodiments, the status indicator module 230 includes a light emitting diode (LED) 330, such as shown in FIG. 3A. The LED 330 can be a single red/green/blue (RGB) LED. In other embodiments, the status indicator module 230 can include other suitable types of indicator devices including, for example, a single color LED, an electrophoretic ink (or "e-ink") display, a persistent display, or the like. In accordance with some embodiments, the WCD 110 can utilize the indicator module 230 (e.g., via the RGB LED 330 through the exterior window 130) to visually communicate with the user. For example, a red color can be displayed (e.g., for a predetermined period of time) by the LED 330 that the WCD 110 needs to be recharged, and a green color can be displayed to indicate that the WCD 110 is fully charged. For another example, a blue color can be displayed when the communication module 250 is in use. In one or more embodiments, the user can program a fitness goal (e.g., a target heart rate) to the WCD 110 so that, for example, a green color can be displayed when the heart rate is below the target, a yellow color can be displayed when the target is reached, and a red color can be displayed when the heart rate is above a certain percentage of the set target. Some embodiments of the WCD 110 include the communication module 250 for wireless data transmission. Particularly, in some embodiments, the communication module 250 includes one Bluetooth chip and a Bluetooth antenna 350, such as shown in FIG. 3A. One or more embodiments of the WCD 110 also provides the capability of storing activity logs (e.g., in the memory 260). More specifically, fitness activities, exercise histories, as well as recorded biological signs such as heart rate and body temperature, can be stored onboard in the memory 260 of the WCD 110. Each data entry in the activity logs can be time-stamped using, for example, an onboard real-time clock (e.g., which may be included in miscellaneous modules 270). For power saving and other purposes, the activity log can be downloaded (e.g., via the communication module 250) when requested by the user. In other embodiments, the activity log can be pushed (e.g., via email or other suitable means) by the WCD 110 to a user device at a time designated by the user. In some embodiments, the memory 260 can store up to a full week worth of activity logs.

The WCD 110 can include the power generation and management module 240 for recharging the battery 280 and for providing electrical power to various modules 210-270 in the WCD 110. Particularly, in some embodiments, the power generation and management module 240 includes one or more concentrated photovoltaic (CPV) cells 340, such as shown in FIG. 3A. The CPV cells 340 can be high-efficiency tandem solar cells and can be attached on the flexible printed circuit (e.g., circuit 415, 515). Because the small form factor of the embodiments of the WCD 110, CPV cells 340, which can absorb more light energy from a wider spectrum of light than the traditional solar cells, are used. In some embodiments, multiple (e.g., 3) CPV cells 340 can be configured in series to provide sufficient voltage and/or current for charging the battery 280.

According to some embodiments, the WCD can include one or more sensing or imaging devices that can be any type of device capable of detecting electromagnetic radiation, such as visible light, IR, NIR, UV, etc. In one example, the device is an imaging device, such as a CMOS or CCD camera.

According to some embodiments, the WCD 110 can be placed or docked into a charging station for recharging.

Figure 6:
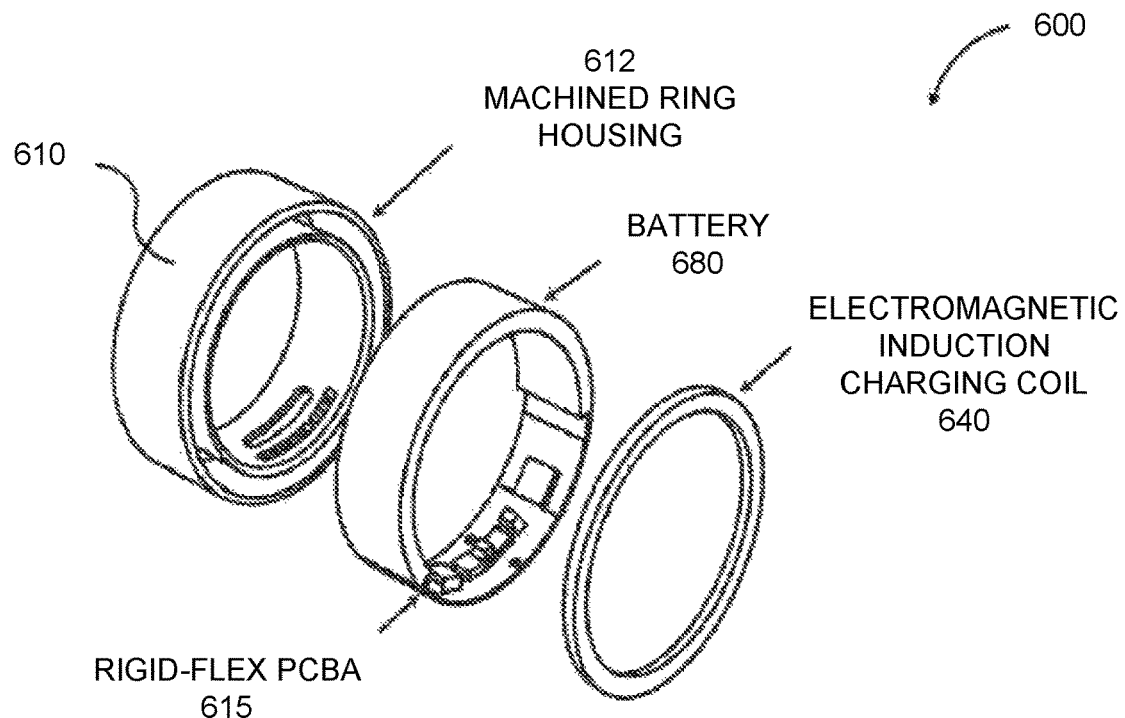
FIG. 6 is an exploded view of a WCD with an alternative charging mechanism in accordance with some embodiments.

In some embodiments, the power generation and management module 240 can include electromagnetic induction charging coil so that a WCD (e.g., ring 610) can be charged using an inductive charger. FIG. 6 shows an exploded view 600 of such alternative embodiment of WCD with the inductive charging mechanism including the charging coil 640, as well as battery 680, housing 612, and rigid-flex PCBA 615. However, it is noted that there may be a need to manufacture the inductive charging coil 640 in different sizes that correspond to different ring sizes. Further, it is noted that the efficiency of the electromagnetic induction charging mechanism may be adversely affected by the adoption of a metallic housing. Additionally or alternatively, to avoid multiple sized coils mounted to the edge of the ring, the coil can be placed on the inner or outer sides of the ring by positioning the coil beneath a window in the metal housing of the ring.

In order to achieve optimal power management of the WCD, one or more of the components can be selected to minimize power usage. For example, a processor, memory, or any other component can be selected based on rated power usage. In one example, it may be desirable to select components that draw current on the order of microamps in order to extend the battery life of the WCD and to allow the WCD to perform health/activity monitoring functions between charging sessions.

Figure 7:
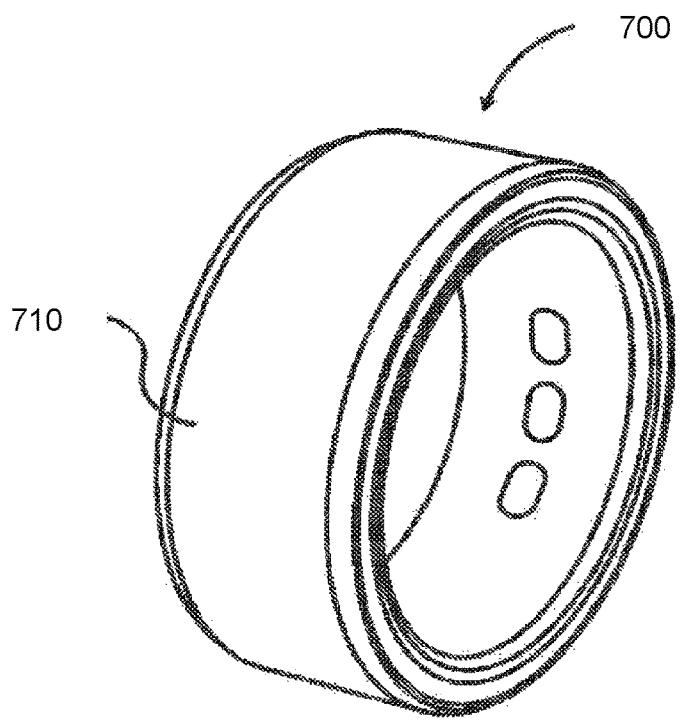
FIG. 7 is a perspective view of an alternative design of a WCD in accordance with some embodiments.
Figure 8:
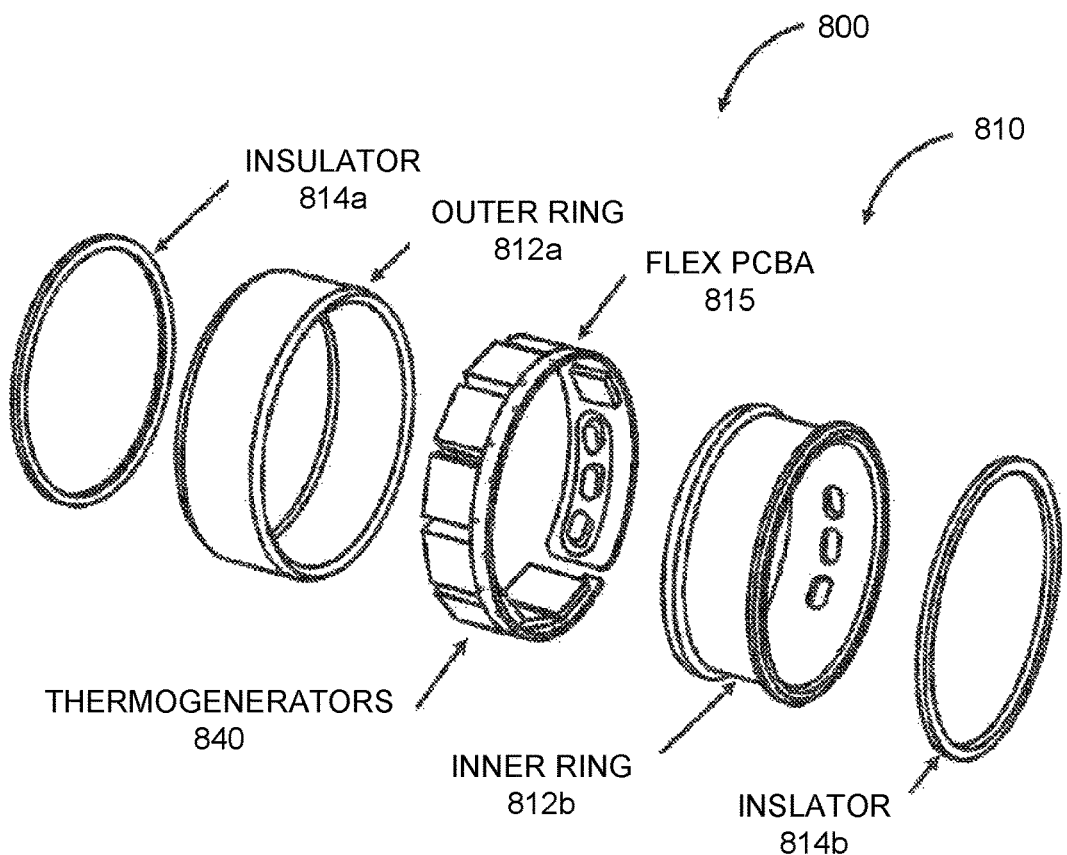
FIG. 8 is an exploded view of the WCD of FIG. 7 illustrating another alternative charging mechanism in accordance with some embodiments.

In still some other alternative embodiments, the power generation and management module 240 can include thermoelectric generator (TEG) modules so that a WCD (e.g., WCD 710, 810) can be charged by the difference between the body temperature and the ambient temperature. FIG. 7 is a perspective view 700 of such alternative design, and FIG. 8 is an exploded view 800 of the WCD 710 of FIG. 7. Also shown in FIGS. 7 and 8 is an alternative design of the housing for the WCD where the ring includes an outer ring 812a, an inner ring 812b, and insulators 814a and 814b. However, it is noted that utilizing TEGs for charging the battery may be less than ideal since the difference between body temperature and ambient temperature might not be great enough to fully charge the battery, and that in many occasions (e.g., during sleep), the temperature difference needed for TEG to generate electricity may quickly disappear (e.g., since the WCD 710, 810 may be covered inside the comforter).

The battery can be any type of battery, such as a rechargeable battery. The battery can be a thin, flexible lithium ceramic chemistry battery. In another example, the battery can be a circular formed lithium polymer or lithium ion battery. The battery can provide power to any of the components described above. In one example, the battery can be a lithium cell integrated directly with the flexible PCB described above. Other implementations can integrated the battery directly onto the housing to reduce the volume of space taken up by battery packaging.

The WCD can also include one or more polymer or piezo actuators for providing appropriate haptic or physical feedback and alerts to a user while the user is wearing the ring. The piezo actuator can also provide audible feedback to a user.

Figure 9A:
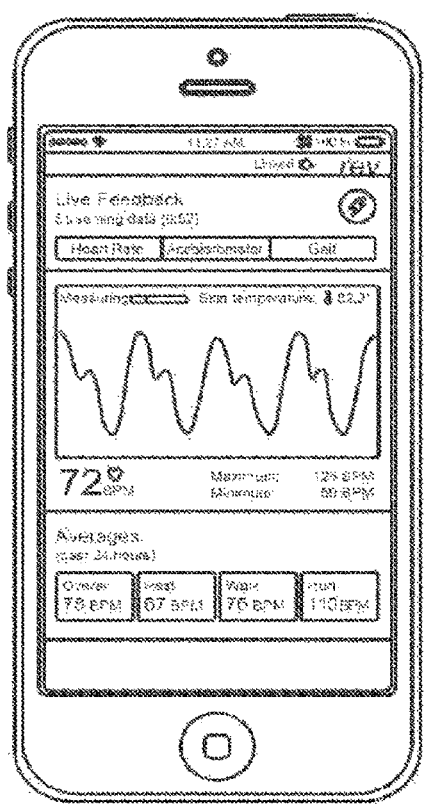
FIGS. 9A-B are example screenshots illustrating a user interface of a mobile application in accordance with some embodiments.

As previously mentioned, the WCD 110 can be used with a software application (e.g., a mobile phone application for the Apple iOS or the Google Android OS) which can run on the user's computing device (e.g., a mobile device such as a smart phone). Specifically, the software application can facilitate the mobile device of the user to couple to the WCD 110 (e.g., via the communication module 250) for data communication, such as downloading activity logs, changing configuration and preferences, training the WCD. The software application can also generate a user interface showing the results or readings from the health and fitness tracking performed by the WCD 110. FIG. 9A is an example screenshot illustrating such user interface 1000 displaying fitness monitoring readings in accordance with some embodiments.

Figure 9B:
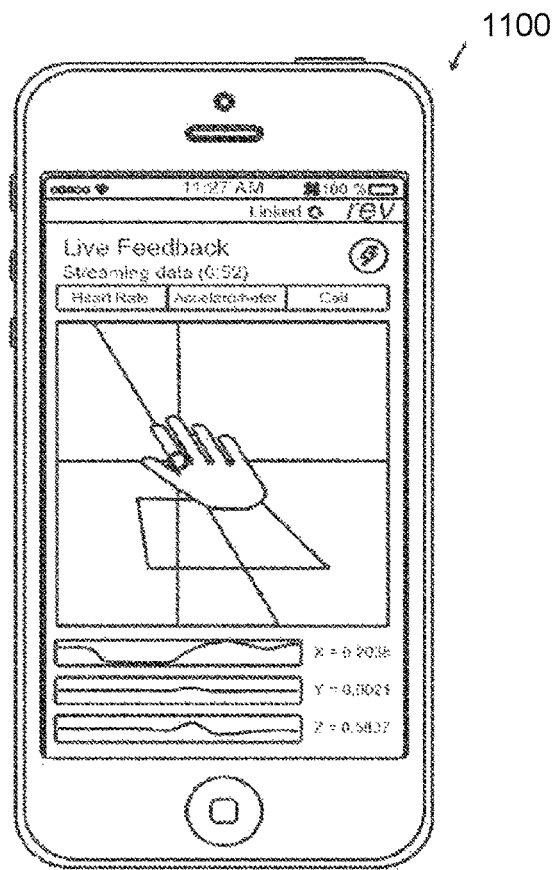

Further, the WCD 110 can be used for gesture input, and the software application can facilitate the user to customize gesture input and control. FIG. 9B is an example screenshot illustrating such user interface 1100 displaying sensor readings (e.g., for calibration purposes) in accordance with some embodiments. In one or more embodiments, the WCD 110 can also be used directly with other Bluetooth enabled devices such as electronic locks or keyless car entry. In other examples, the WCD 110 can also control other devices via a smartphone and other Wireless LAN enabled devices such as home automation systems.

Figure 3C:
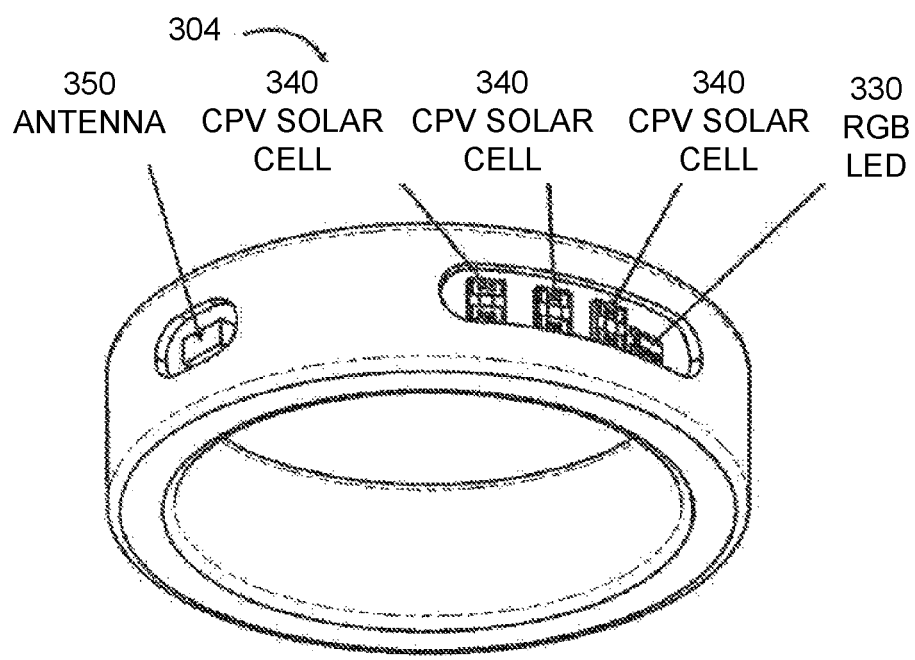

FIG. 3C is a view 304 of two exterior windows of an alternative WCD (e.g., WCD 112 of FIG. 3C) with example components exposed in accordance with some embodiments. The components 330, 340, and 350 shown in FIG. 3C function similarly to those components described in FIG. 3A. However, some components (e.g., antenna 350) can be positioned to face a different exterior window than the exterior window the rest of the components face. This may increase the mechanical strength of the housing structure of the ring, and/or may reduce signal interference among the components.

Figure 4:
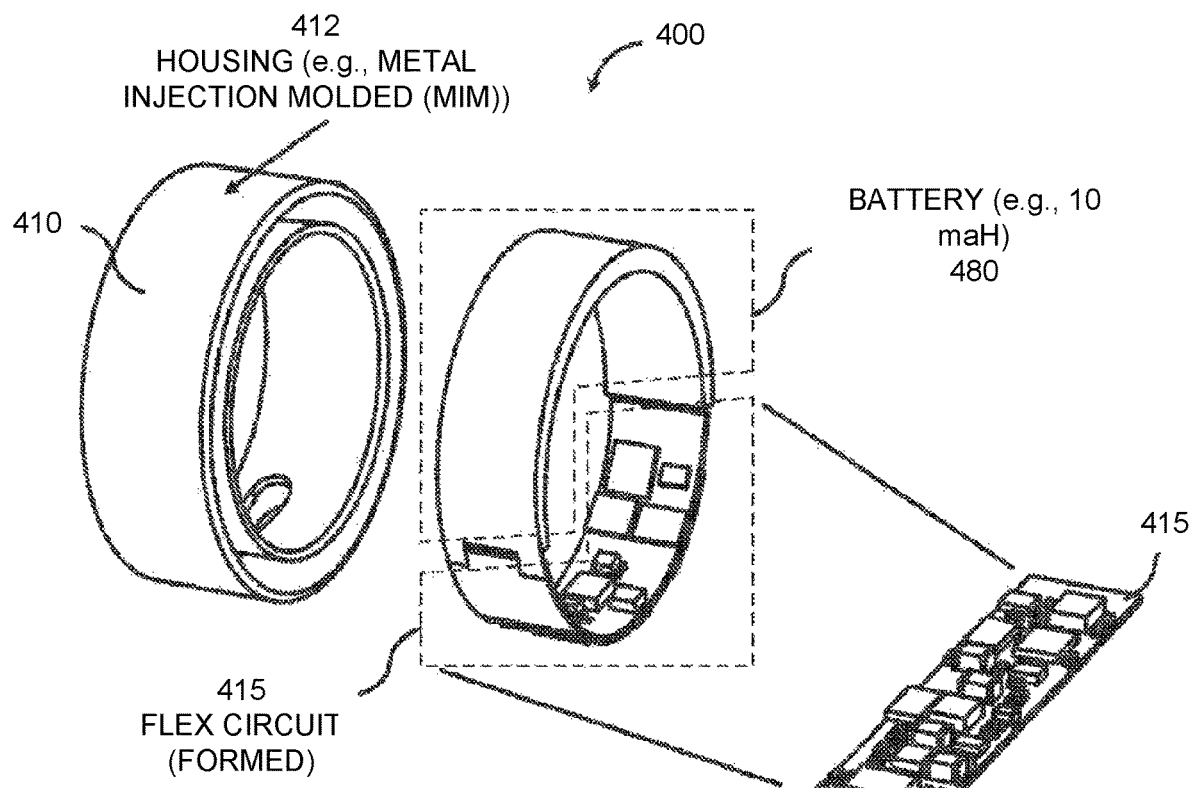
FIG. 4 is an exploded view of a WCD illustrating a battery and a flexible circuit which are configured to fit inside the housing of the WCD in accordance with some embodiments.
Figure 5:
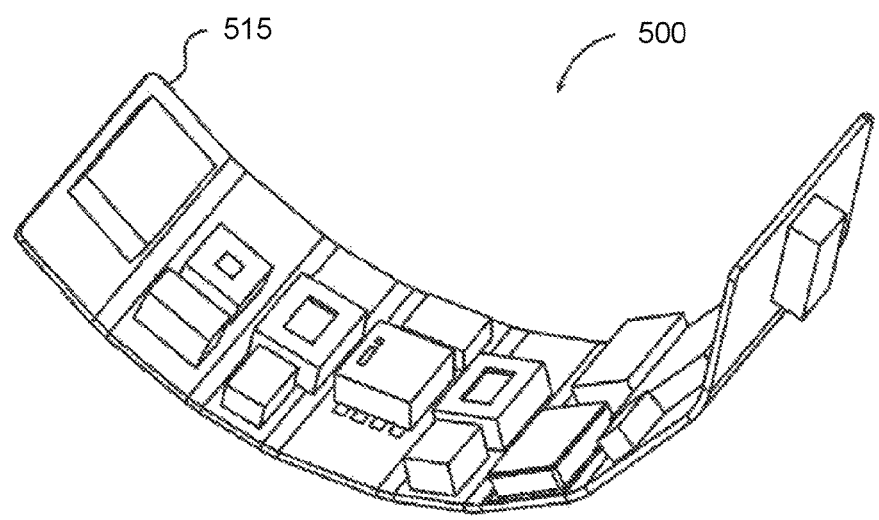
FIG. 5 is a perspective view of the flexible circuit of FIG. 4 in accordance with some embodiments.

FIG. 4 is an exploded view 400 showing an exemplary WCD 410 (e.g., WCD 110) illustrating a battery 480 and a flexible circuit 415 which are configured to fit inside a housing 412 of the WCD 410. It is recognized by the present disclosure that a human being's finger can come in various different sizes and so should the WCD 410. In order to reduce the cost of manufacturing different sizes of printed circuits, in some embodiments, the modules 210-270 (of FIG. 2) are formed on a flexible or rigid-flex printed circuit (FPC) board, an example 500 of which is shown as FPC 515 in FIG. 5. In particular, one or more embodiments provide that the FPC 515 and the battery 480 are not specific to a ring size, and that the same circuitry and/or battery can fit a multitude of sizes.

According to some embodiments, the WCD 410 provides a desirable form factor for a user to wear it for a prolonged period of time. The edges and the shape of the WCD 410 can be configured in a way that is comfortable and ergonomic; for example, the finished parts of the embodiments are to be free from burrs and sharp edges. The material which forms the housing portion of the WCD 410 can include medical grade metallic alloys that reduce the likelihood of allergic reactions. Examples of the housing material include stainless steel, tungsten carbide, titanium alloy, silver, platinum or gold.

In the examples shown in FIG. 4, the U-shape of the ring housing 412 allows for the flexible PCB 415 to be inserted into the edge of the WCD 410. The windows (e.g., windows 120, 130) on the walls of the WCD 410 can align with the operating circuitry to allow, for example, battery charging, Bluetooth connection, and user feedback LED/micro display on the outer wall, and biological feedback sensors (e.g., pulse oximetry, temperature sensor) on the inner wall. In one or more embodiments, the WCD 410 can be completely sealed using potting epoxy. The sealing epoxy can be transparent to allow light to pass through for the CPVs and sensors. In some embodiments, the WCD 410 can be potted with two different compounds. In these embodiments, the body of the WCD 410 can be filled with clear material, and the edge of the WCD 410 can be filled with an opaque material so that different colors can be incorporated (e.g., as a decorative element). It is noted that sealing the assembly using potting epoxy can also bring the additional benefit of making the WCD 410 completely or almost completely waterproof as well as increasing the structural rigidity of the WCD 410.

Internal Housing/External Potting

Figure 10A:
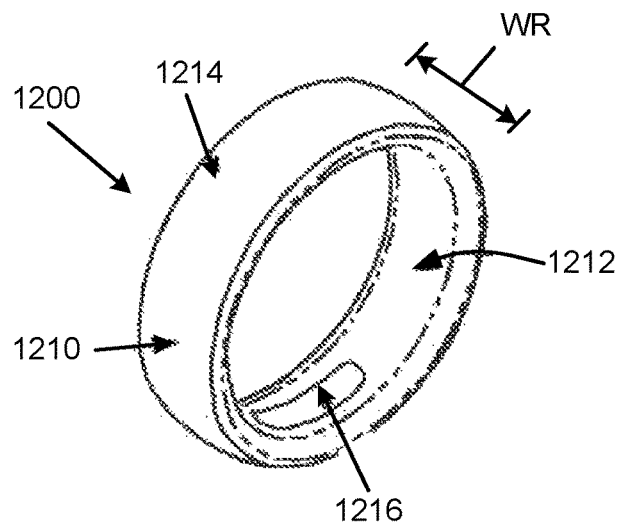
FIGS. 10A-F are perspective views of a wearable computing device (WCD) according to one or more aspects of the disclosure.
Figure 10B:
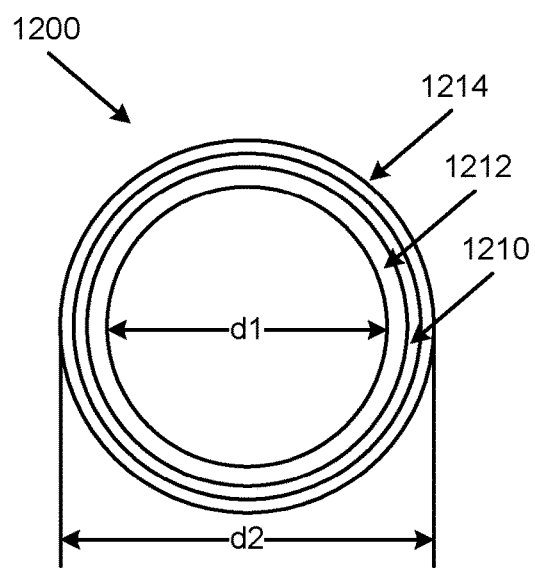
Figure 12A:
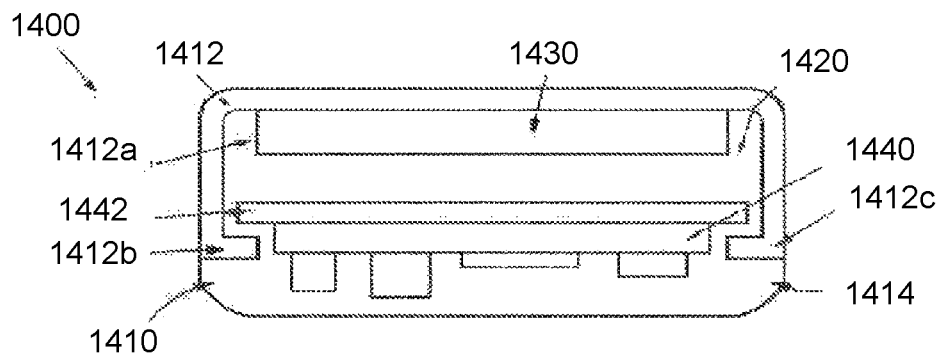
FIGS. 12A-E are views of a WCD according to another aspect of the disclosure.

FIG. 12A is a perspective view and FIG. 10B is a side view of a WCD 1200 according to one or more aspects of the disclosure. The WCD 1200 can be in the shape of a ring and can be worn on any of the five fingers (including the thumb) of (typically) a human user. In this regard, the WCD 1200 can define an interior diameter di and exterior diameter $d_2$. The interior diameter di can be defined as the distance between opposing points on the interior surface of the ring, with the interior surface being the portion of the WCD facing the finger of a user while the device is worn by the user. The interior surface of the WCD can generally define a finger space for receiving the finger of the user. The exterior diameter $d_2$ can be defined as the diameter between opposing points on the exterior surface of the ring, with the exterior surface being the portion of the WCD opposed to the interior surface and facing away from the finger of the user.

The interior diameter di and exterior diameter $d_1$ can be any size to accommodate any finger size. In one example, $d_2$ is determined by di plus a thickness of any components and/or flexible circuit boards disposed within the WCD. Additionally, although depicted as being circular, the finger space of the WCD 1200 can be any shape, such as ovular, elliptical, or the like, to accommodate users with atypical finger profiles. In these examples, the dimensions of the interior and/or exterior diameter may be measured according to other variables, such as length, width, major diameter, minor diameter, etc. By way of non-limiting example, the WCD interior diameter di (the diameter generally defining the ring size) can be in an approximate range of 12 mm to 24 mm so as to accommodate finger sizes ranging from a small child to a larger adult, and on any acceptable finger, including the thumb. The exterior diameter $d_2$ can also be any reasonable size or shape, and can define an approximate range of between 18 mm and 30 mm. Likewise, the thickness between diameters $d_1$ and $d_2$ can vary widely, but can typically reside in an approximate range of 1.5 mm to 3 mm. The width WR of the WCD along the direction of finger extension (finger longitudinal direction) is widely variable, and can be selected, in part to accommodate internal and external components. In a non-limiting, example, the width WR is in a range of approximately 3 mm to 8 mm.

The WCD 1200 can include an overall housing 1210 that includes an internal housing 1212 and an external potting or encapsulant 1214. Together, the internal housing 1212 and external potting 1214 combine to form the overall form factor of the WCD 1200, in addition to providing a housing for one or more electronic components stored within the housing 1210 of the WCD 1200, as will be described in greater detail below.

The internal housing 1212 can be formed of any material, such as a nonconductive material, a conductive material, a ferrous material and/or a nonferrous metal, composite material (e.g. carbon-fiber and/or glass fiber composite) a dielectric material, or a combination of any of the above. In one example, the material of the inner housing 1212 is conductive and nonferrous, such as aluminum, titanium, or stainless steel. In other examples, the internal housing can be formed of a polymer, such as plastic. The external potting 1214 can be formed of any material, solid or gelatinous, that can provide resistance to shock and/or vibration and can prevent moisture and/or debris from entering the housing 1210 of the WCD 1200, such as silicone, epoxy, polyester resin or any other polymer.

In one example, the external potting 1214 can be transparent. In this regard, the transparent external potting can allow electromagnetic radiation, such as visible, IR, or UV light sources from inside the housing 1210 to pass through the external potting 1214 without the need of a window or discontinuity in the external potting 1214 and without changing the optical properties of the radiation. In the same vein, electromagnetic radiation sources, such as visible, IR, or UV light, external to the housing can pass through the external potting 1214 and can be detected by, sensed by, or fall incident upon internal components of the WCD 1200 without the need for a window or discontinuity in the housing and without changing the optical properties of the radiation. In another example, the external potting 1214 can be tinted. The tint can be cosmetic and can prevent the internal components of the WCD to be visible by the user. In this regard, depending on the tint, optical properties of light passing therethrough may be slightly changed. For example, certain colors of the light can be filtered and can result in decreased power transmission. The above description regarding external potting 1214 can be applied to any of the pottings described below.

The internal housing 1212 can define a window 1216. In one example, the internal housing is formed of a material that completely or partially prevents light (or other electromagnetic radiation) from passing through the internal housing 1212. In this regard, the internal housing 1212 can define the window 1216 to allow for such radiation to pass through the housing 1212. As shown, the window 1216 can be generally elliptical-shaped, but can be any other suitable shape according to other examples, such as rectangular, circular, ovular, etc. Since the window 116 is defined by the internal housing 1212, the window 1216 can face the finger of the user while the user is wearing the WCD 1200, which can provide many advantageous features and implementations, as will be described in greater detail below.

Figure 10C:
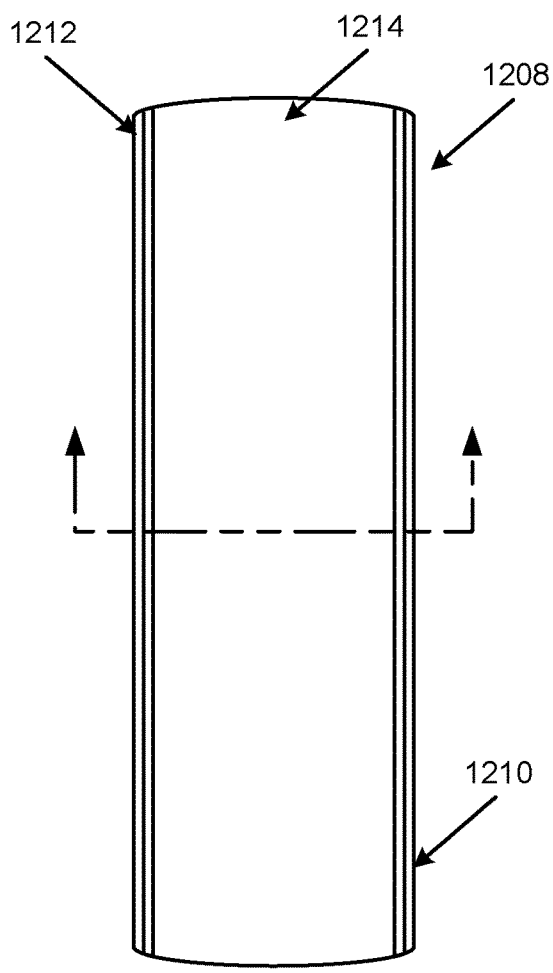
Figure 10D:
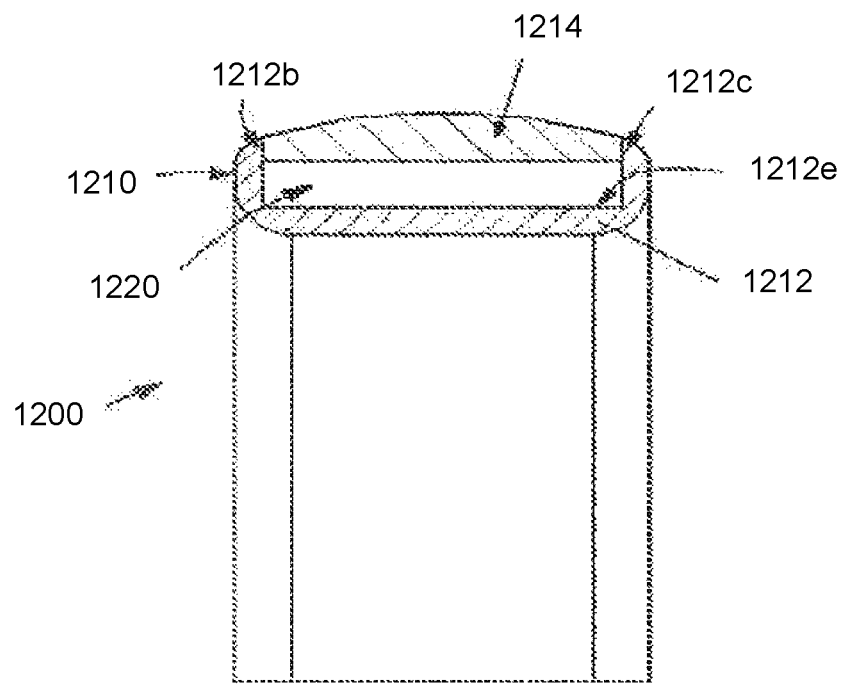

FIG. 10C is a front view of the WCD and FIG. 10D is a cross section of the WCD 1200 along the line A-A of FIG. 10C. As shown, the internal housing 1212 can have a generally U-shaped internal surface 1212a to accommodate one or more internal components and can define a pair of flanges 1212b and 1212c. The external potting 1214 can extend between the flanges 1212b and 1212c of the internal housing to provide an internal space 1220 to accommodate one or more components. By virtue of the external potting 1214, the internal space 1220 defined by the internal surface 1212a and the external potting 1214 can be hermetically sealed, thereby preventing debris, dust, moisture, or any other unwanted fluids or materials from interacting with the internal components of the WCD 1200. Although not depicted, the internal components can reside within the internal space 1220, and the external potting 1214 can be disposed immediately atop the components to provide the seal.

Figure 10E:
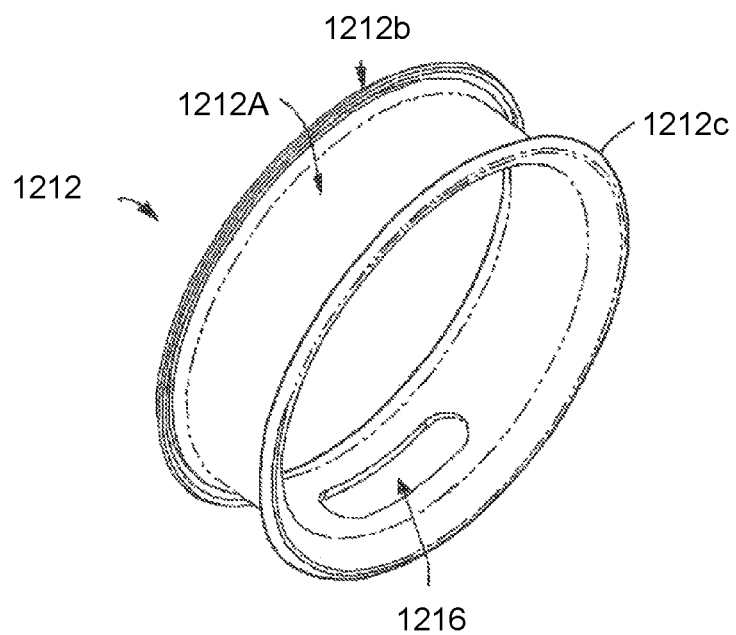

FIG. 10E is a perspective view of the internal housing 1212 without external potting 1214. As shown, the internal surface 1212a defines a generally U-shaped surface for receiving the components.

Figure 10F:
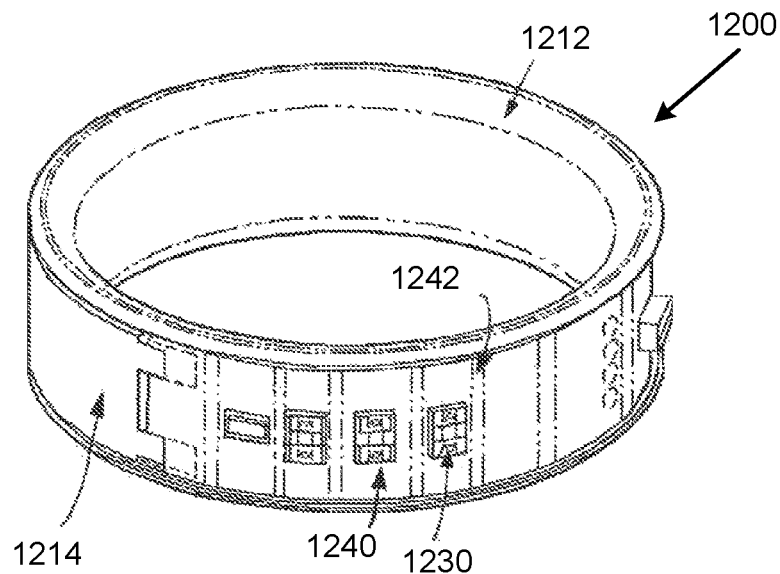

FIG. 10F is a perspective view of the internal housing 1212 with a portion of the external potting 1214 removed and showing one or more components 1230 and printed circuit board (PCB) 1240. The components and PCB can be constructed as flex circuits, thereby allowing the components 1230 and PCB 1240 to be geometrically configured within the ring shaped internal space 1220. The PCB 1240 can be any type of flexible material clear to those of skill, such as polyimide, PEEK, etc. Additionally, the PCB could be rigid-flex whereby panels of RF4 are connected together with a flexible substrate.

As shown, the PCB 1240 and the components 1230 can be disposed within the internal space 1220 generally defined by the internal surface 1220a and the flanges 1220b-c. The PCB 1240 can define one or more folding regions 1242 that allow the PCB 1240 to conform to the circumference and/or perimeter of the internal surface 1212a. The PCB 1240 can extend around at least a portion, or up to an entire circumference, of the internal surface 1212a. In one example, the size of the internal diameter di of the WCD can determine the portion of the internal surface 1212a around which the PCB 1240 extends, illustratively, for a larger ring size and a larger internal diameter $d_1$, the PCB 1240 can extend only a portion (an arc) of the overall circumference, while for smaller ring sizes a greater portion (arc) of the circumference can be employed to accommodate PCB 1240 and the internal components 1230. The adjacent portions of PCB can form an arc angle therebetween by virtue of the folding regions disposed therebetween, allowing for the PCB to be conform to the internal surface 1212a.

External Housing/Internal Potting

Figure 11:
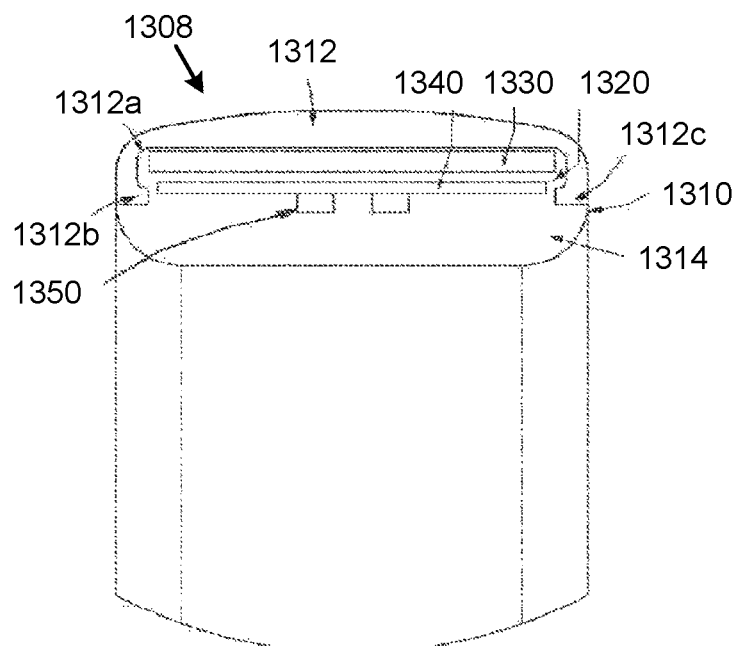
FIG. 11 is a cross section of a WCD according to another aspect of the disclosure.

FIG. 11 is a cross section of a WCD 1300 according to another aspect of the disclosure and illustrative embodiments. In this example, the WCD 1300 includes a housing 1310 that includes an external housing 1312 and an internal potting or encapsulant 1314. The external housing 1312 includes an internal surface 1312a that has a generally C-shaped cross section but alternate cross section shapes, such shapes with an external notch or groove. The external housing includes flanges 1312b-c that extend toward each other, beyond portions of the internal surface 1312a, to define a partially enclosed internal space 1320. In an assembled state, the WCD 1300 can include a battery 1330, a PCB 1340, and components 1350, which can be at least partially or completely disposed within the partially enclosed internal space 1320. The internal potting 1314 can extend between the flanges 1312b-c and can seal the partially enclosed internal space 1320. The components can be encapsulated by the internal potting 1314. The PCB 1340 and components 1350 can extend along an inner circumference of the internal surface 1312a.

Illustratively, the external housing 1312 can be formed of the same materials as the internal housing 1212 described above, and the internal potting 1314 can be formed of the same materials as the external potting 1214 described above. As also described above, the internal potting 1314 can be transparent and the external housing 1312 can define one or more windows according to one or more aspects of the disclosure.

FIG. 12A is a cross section of a WCD according to another aspect of the disclosure and illustrative embodiment. In this example, the WCD 1400 includes a housing 1410, internal surface 1412a, an internal or external housing 1412, an internal or external potting 1414, an internal space 1420, a battery 1430, a flexible circuit 1440, and one or more components 1450. This example is similar to the examples described above with respect to FIGS. 10 and 13, except the addition of a stiffener element 1442 and the flanges 1412b-c extend further into the space 1420 toward one another such that the flanges 1412b-c overlap with the stiffener element 1442.

Figure 12B:
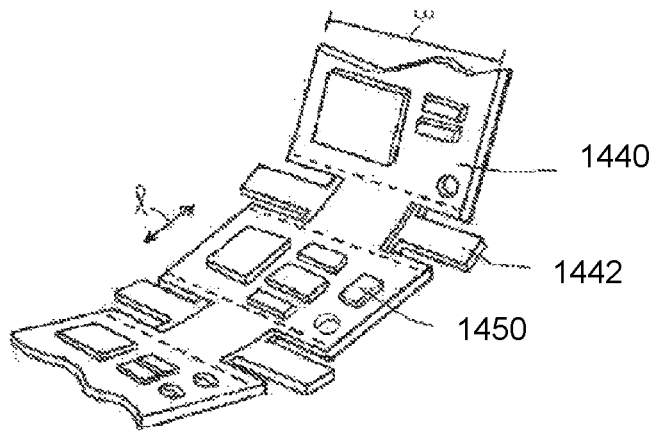
Figure 12C:
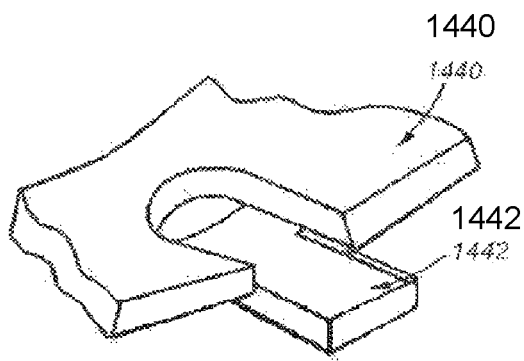

FIG. 12B is a perspective view of the PCB and stiffener element of FIG. 12A. As shown in FIG. 12B, the stiffener element 1442 extends beyond an overall width w of the PCB 1440 and extends wider than a distance between flanges 1412b-c. The stiffener element is disposed between folding regions 1444. The PCB 1440 can include one or more stiffener elements 1442 attached thereto, and the elements 1442 can be disposed periodically (in separated intervals) along a length l of the PCB 1440. As shown in FIG. 12C, the stiffener element 1442 can be disposed underneath the flexible circuit 1440, e.g., on a face of the flexible circuit 1440 opposed to the face on which the components 1450 are disposed, and can be permanently or semi-permanently attached thereto. The stiffener element can be implemented in any of the configurations described, and in particular, with either the internal housing/external potting arrangement or the external housing/internal potting arrangement.

The stiffener element 1442 can be formed of any material, such as polyamide or thin FR4, depending on construction of the PCB 1440. In particular, the material of the stiffener can be chosen to be more or less flexible than the PCB 1440. In one example, the stiffener element 1442 can be a polyamide stiffener disposed on a back surface of a flexible PCB. In another example, the stiffener element 1442 can be FR4 and can be substantially flush with respect to the flanges 1412b-c. In this regard, the stiffener element can extend substantially the distance between flanges 1412b-c and may not deform upon insertion into the space 1420. The stiffener element can include surface features disposed on an edge thereof, with the edge facing one of the flanges 1412b-c. The surface features can include a sawtooth profile (e.g., intersecting straight lines at acute angles), or any other type of feature capable of providing an interference fit between flanges 1412b-c.

Figure 12D:
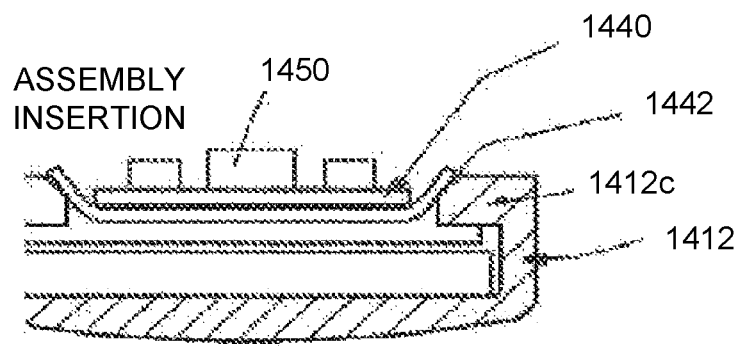

FIG. 12D shows a cross section of the WCD at a point in time during assembly/manufacture when the PCB 1440 is being inserted into the internal space 1420 and prior to the application of potting 1414. As shown, the stiffener 1442 contacts the flanges 1412b-c of the housing 1410 by virtue of the width w of the stiffener element 1442. Upon an application of force, the PCB 1440 and stiffener 1442 assembly can be inserted into the internal space 1420. In this regard, the stiffener element has a predetermined flexibility that allows for a certain amount of flexion, as shown in FIG. 12D. The flexion allows for the flexible circuit 1440 to be inserted within the internal space 1420 and can prevent the flexible circuit 1440 from being removed or from accidentally falling out once inserted. In this regard, the flexible circuit 1440 is held in place within the space 1420 by virtue of the width of the stiffener element 1442 and the distance between the flanges 1412b-c. Once inserted, the potting 1414 can be applied free of the concern of improper positioning of the flexible circuit 1440.

Figure 12E:
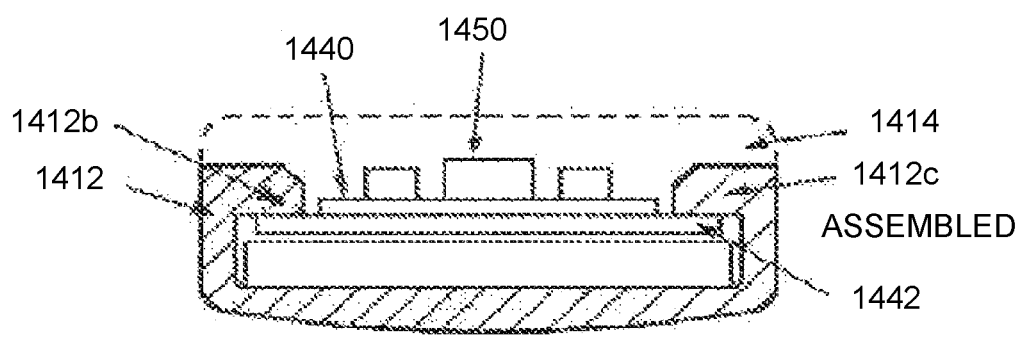

FIG. 12E is a cross section of the WCD of after a potting material 1414 has been applied subsequent to the WCD of FIG. 12D.

Inner/Outer Bands

Figure 13A:
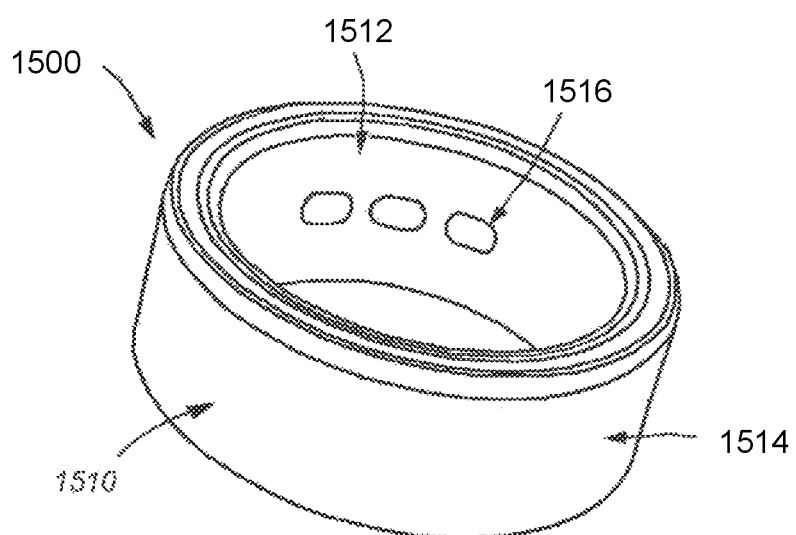
FIGS. 13A-B are views of a WCD according to another aspect of the disclosure.

FIG. 13A depicts a perspective view of a WCD 1500 according to another aspect of the disclosure. In this example, the WCD includes a housing 1510 that includes an internal housing 1512 and an external housing 1514. The internal housing 1512 can be similar to the internal housing described above with respect to internal housing 1212, and the external housing can be similar to the external housing described above with respect to external housing 1312. The internal housing 1512 can include one or more windows 1516 that can allow electromagnetic radiation (e.g. visible and near-visible light) to pass therethrough, allowing it to fall incident upon components disposed within the housing 1510 and allowing EM radiation sources (e.g. visible light, RF, IR, etc.) within the housing to exit the housing.

Figure 13B:
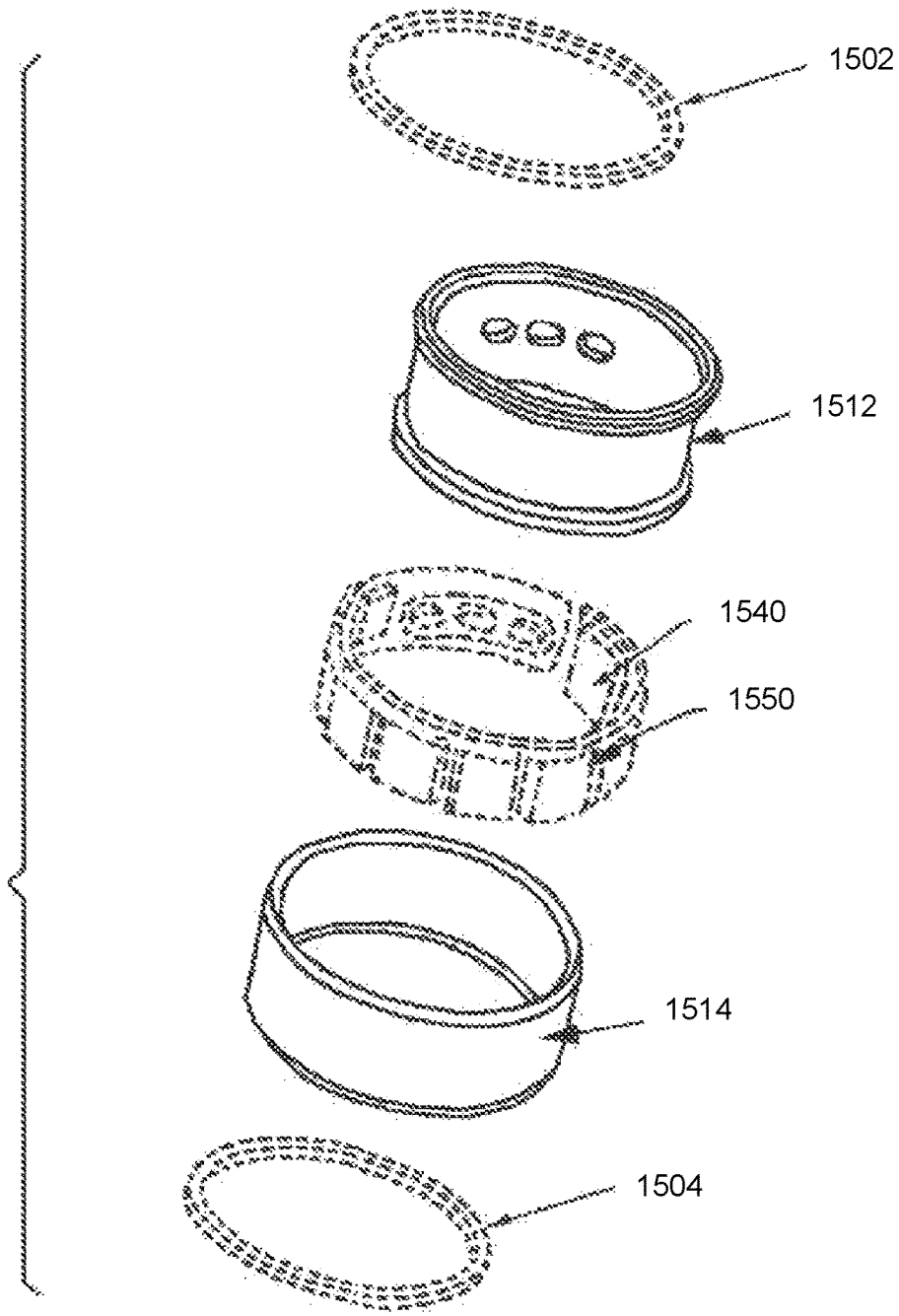

FIG. 13B is an exploded view of the WCD 1500. As shown, the WCD can include internal housing and external housing 1512 and 1514. The WCD can further include a PCB 1540 and components 1550. Once the housings 1512-1514 are assembled and the PCB 1540 and components 1550 are assembled within space defined between the housings 1512-414, potting layers 1502 and 1504 can be applied to seal the WCD at both sides thereof to ensure a secure seal.

Inner/Outer Bands with U Shaped Window

Figure 14A:
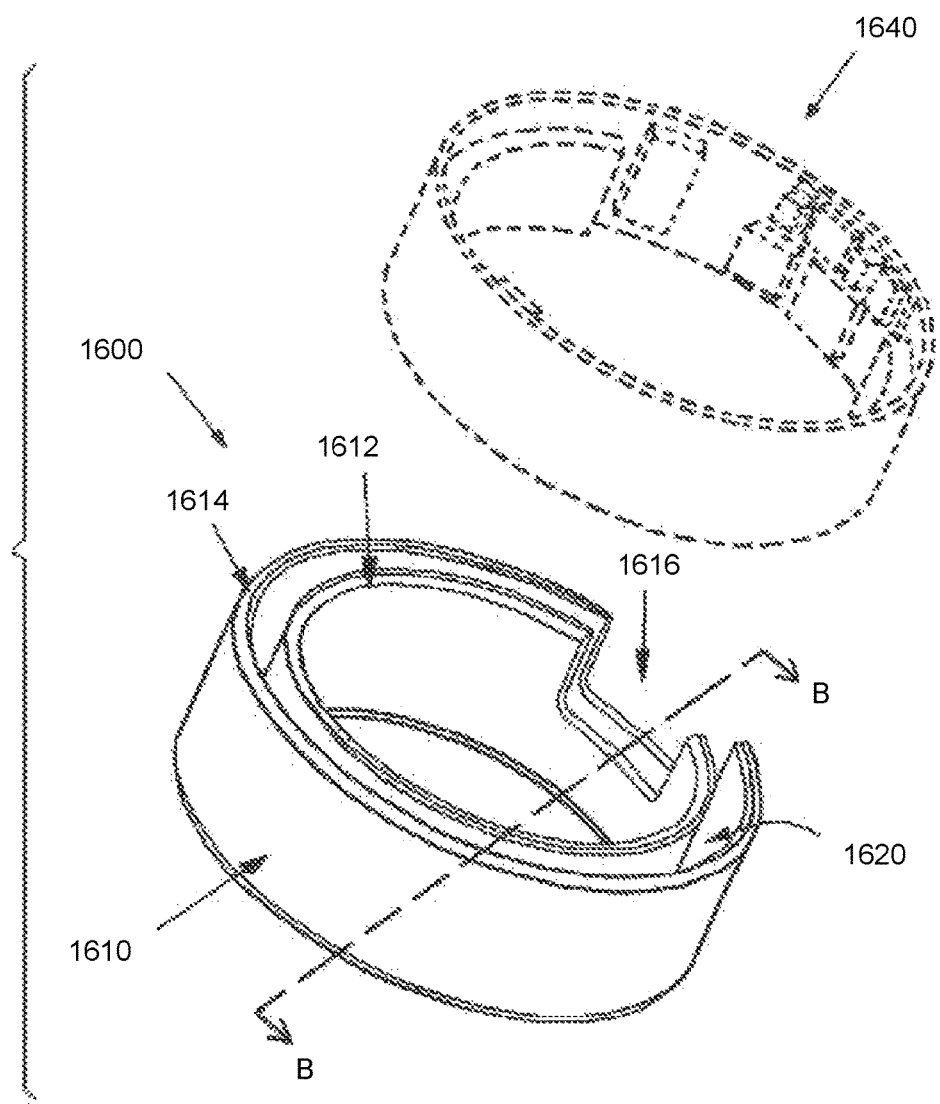
FIGS. 14A-C are views of a WCD according to one or more aspects of the disclosure.

FIG. 14A is an exploded view of a housing 1610 and a PCB of a WCD according to one or more aspects of the disclosure. The WCD 1600 comprises a housing 1610 with an integral inner wall and outer wall 1612 and 1614. The housing can be made of any material, such as any material described above with respect to the internal/external housing structures. In this example, the inner and outer walls 1612, 1614 each define a window in the shape cutaway portions 1616. The cutaway portions are bounded on three sides by the walls 1612 and 1614 and unbounded at the other side thereof. The cutaway portions 1616 can be aligned with one another to ensure transmission of radiation into/out of the housing 1610. The space 1620 between the inner and outer walls 1612, 1614 can receive a PCB 1640, battery, components, etc.

Figure 14B:
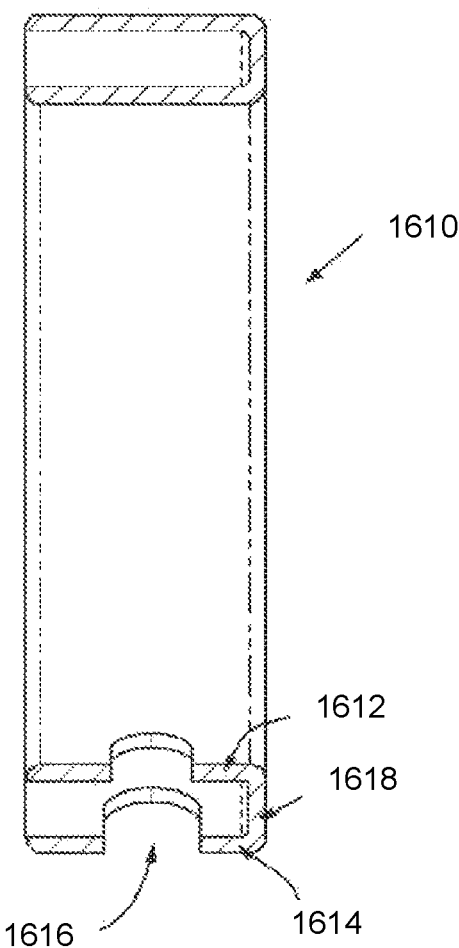

FIG. 14B is a cross section of FIG. 14A along line B-B. As shown, the inner and outer walls 1612, 1614 are directly connected by a floor 1618. The space 1620 is defined by the space between the inner and outer walls 1612, 1614 and the floor 1618.

Figure 14C:
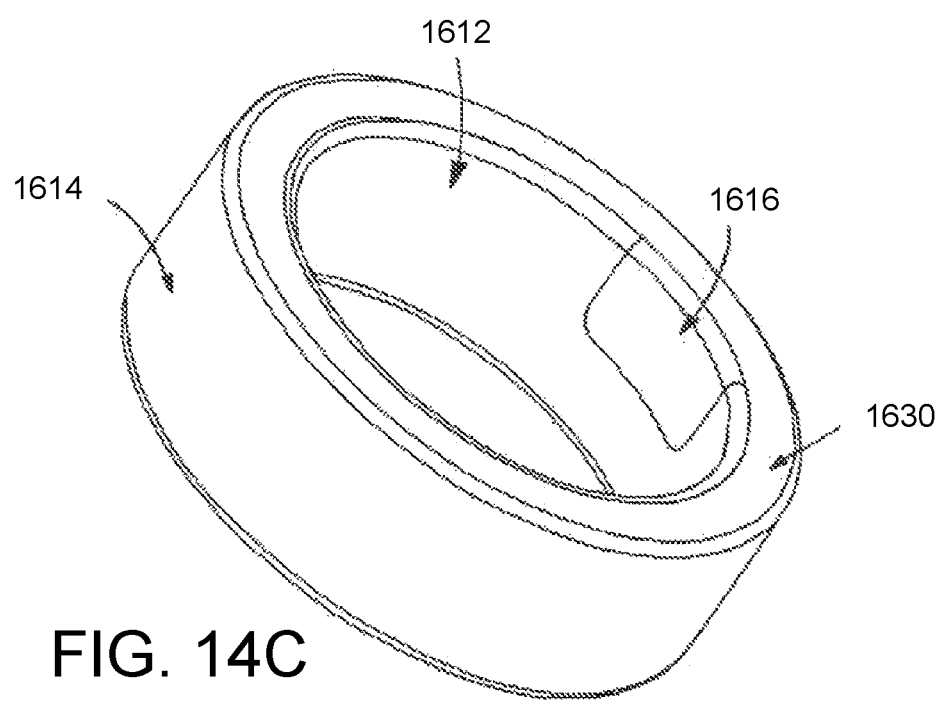

FIG. 14C is a perspective view of the WCD with potting material 1630. As described above, the PCB, battery, and components can be disposed within the space. Once disposed therein, a potting 1630 can be provided atop the components and within the cutaway portion 1616. The potting 1630 can be transparent to allow for transmission of light through the cutaway portions 1616.

FIG. 15 is a perspective view of a base assembly 1750 and WCD 1700 according to one or more aspects of the disclosure. As shown, the WCD 1700 is in the shape of a ring and the base assembly 1750 includes a post 1754 for receiving the ring. The post 1754 can be cylindrical and can be sized and shaped according to an internal diameter of the WCD in order for the WCD to be received on an external surface of the post. The first opening 1752 of the base assembly 1750 is formed on a portion of the post 1754 such that, when the WCD 1700 is stored on the post, the second opening 1712 can be aligned with the first opening 1752 to ensure alignment of the CPV and the concentrated light source. The base assembly can receive/transmit power and/or data via external input/output 1795, which can be a DC power input, a USB input connection or any other acceptable connection/form factor.

In some examples, the WCD can be adapted to uniquely identify the wearer of the WCD using, for example biometric features unique to the user.

FIG. 16A is a schematic view of a WCD 2100 showing components used for identifying the wearer of the WCD. As shown, the WCD 2100 can include one or more infrared illumination sources 2110 and an infrared CMOS imaging device 2120. The finger 2190 can extend through the finger space of the WCD and the IR source 2110 can illuminate a portion of the skin of the finger 2190. The IR CMOS imaging device 2120 can receive light that has been reflected from the skin surface and produce an image of the skin of the finger 2190. As shown, the IR source 2110 and the imaging device 2120 are positioned near the interior surface of the WCD, e.g., the surface facing the skin of the finger. The IR illumination can pass through a window provided on the interior housing or can pass through a transparent potting material.

During the imaging process, the WCD 2100 can be rotated about an axis passing through the center of the finger space and along the longitudinal direction of the finger. In this regard, the imager 2120 can capture a larger swath of the skin surface than if the WCD 2100 were held stationary with respect to the finger during the imaging process.

At the time of first use, or any time thereafter, the user can generate a reference capillary map in order to identify himself/herself as the authorized user of the WCD. As described above and illustrated in FIGS. 16B-C, the user can rotate the WCD around the finger to capture image data of an analyzed section of skin 2192 and on or more capillaries 2194 of the user currently wearing the WCD. The image data can correspond to an overall analyzed section of the skin 2196 of the wearer. The image data of the capillaries can be used to generate a reference capillary map of the wearer, which can be stored in the memory, such as flash memory or EEPROM, of the WCD.

When the same user puts the WCD on his or her finger after generation of the reference capillary map, the WCD can capture image data of the wearer's skin surface that can be compared to the reference capillary map stored in the memory. In this regard, the user need not rotate the device around the finger. Instead, the WCD can compare a subset of the gathered image data to a corresponding subset of reference capillary map. If there a match, within a predetermine error tolerance, the WCD can uniquely identify the wearer as an authorized user of the WCD and as the unique individual who generated the reference capillary map. Once authorized, the wearer can have access to certain functions, features, data, or other content that is not otherwise available without authorization. In another example, the identification can be a step in a transaction or other type of authorization, such as an electronic payment, bank transaction, etc. If the gathered data does not match the reference capillary map, then the user may be prevented from accessing certain features on the WCD.

Illustratively, the comparison process between sensed capillaries and some or all of the capillary map can be implemented using basic pattern recognition algorithms (processes) instantiated in the electronics of the WCD. Such processes can rely on edge detection and similar techniques that should be clear to those of skill in the art and can be sourced from various commercial vendors of biometric recognition software.

In another example, the illumination can include NIR illumination and can project radiation into the skin of the finger. The reflected NIR illumination can then be analyzed to determine one or more characteristics of the blood, such as blood alcohol levels, blood glucose levels, and blood oxygenation levels. In this regard, the WCD analyzes the reflected radiation to identify wavelengths that were absorbed from the projected radiation by the blood of the user. Techniques and processed used in conjunction with commercially available venous oximeters (for example) can be employed to undertake certain readings.

FIG. 17A is a perspective view of a user employing ECG monitoring according to one or more aspects of the disclosure. In this example, the user can wear the WCD 2200 on a first finger 2210 of first hand 2220, and can touch a second finger 2230 of a second hand 2240 to an exterior surface of the WCD 2200. This can provide an electric pathway 2250 through the body, as shown in FIG. 17E, allowing for the transmission of electrical current between distant portions of the body.

FIG. 17C is a perspective view of a WCD that can employ ECG monitoring according to one aspect of the disclosure. In this example, the WCD 2200 includes an internal/external housing 2250 with a conductive pad 2260. The conductive pad 2260 can be electrically isolated from the external/internal housing 2250 of the WCD, thereby providing distinct and isolated electrical contacts on the WCD. The internal/external housing 2250 can be in electrical communication with the first finger 2210 of the first hand, while the conductive pad 2260 can be in electrical communication with the second finger 2230 of the second hand. In this regard, an electrical path 2250 is formed through the respective hands 2220, 2240 and through the rest of the user's body, particularly through the chest. In this regard, the WCD can take various electrical measurements of the user, such as ECG. The ECG measurement can include measurements of the various waveforms, such as P-U waveforms. The WCD can store such ECG data in a memory and/or can communicate the data to a wirelessly connected mobile device. In another example, the WCD can employ electrically isolated internal and external housings, such as those described above. In this regard, the conductive pad may not be utilized, and the user can wear the WCD on a first finger and apply the second finger anywhere on the external housing.

The WCD can also serve as a monitor for those who are mobility impaired or who are prone to falls, such as disabled persons and/or retired persons. The accelerometer onboard the WCD detect a fall of the user via a sudden change in acceleration data. The WCD, in conjunction with a mobile device and/or one or more base stations positioned around the home of the user, can determine the position of the user within the house. For example, the mobile device can employ GPS capabilities, and either the mobile device or the base stations can use GPS in combination with WiFi signal strengths to determine the location of the user within the house. The WCD can then issue an alert, either directly or indirectly (via the mobile device or base station) to a third party that a fall has occurred. The alert can be a phone call, text message, e-mail, or any other type of communication. The third party can then take appropriate measures to aid the fallen user.

The WCD can also monitor heart rate and/or temperature, in addition to the other monitored characteristics described above. If any of the monitored characteristics is abnormal, e.g., measured parameters outside of a predetermined threshold range, an alert can be sent to a third party, in some examples, the third party can be a medical health professional, such as a doctor, nurse, caretaker, etc. It is noted that, for those embodiments which can function as a cardiac monitor (e.g., that measures electrocardiogram (EKG)), it can be necessary to establish a closed loop (e.g., for the electrical measurement of EKG) across the heart. As such, in some of those embodiments, a separate conductive pad or other skin-contacting structure/probe can be coupled to the WCD so that a user can pinch the pad with fingers on an opposite hand.

Since the WCD has the form factor of a ring, the WCD is designed to be worn over long periods of time by a user with little to no discomfort or interference. In this regard, the WCD can monitor the above-described, monitored characteristics over long periods of time (e.g. weeks, months, etc.), and determine trends in the data. For example, the WCD can measure heart rate over a long period of time and determine a unique resting heart rate for a user. If the user's heart rate deviates from the resting heart rate, the WCD can be arranged to issue an alert to a third party. In one specific example, the WCD can use appropriate processes to analyze both the trends of monitored characteristics, as well as current accelerometer data. In this way, if a person's heart rate deviates from a resting heart rate, but the accelerometer indicates that the user is exercising and/or engaging in strenuous activity that provides an equivalent workout, then the WCD may not issue an alert in this circumstance.

Figure 18A:
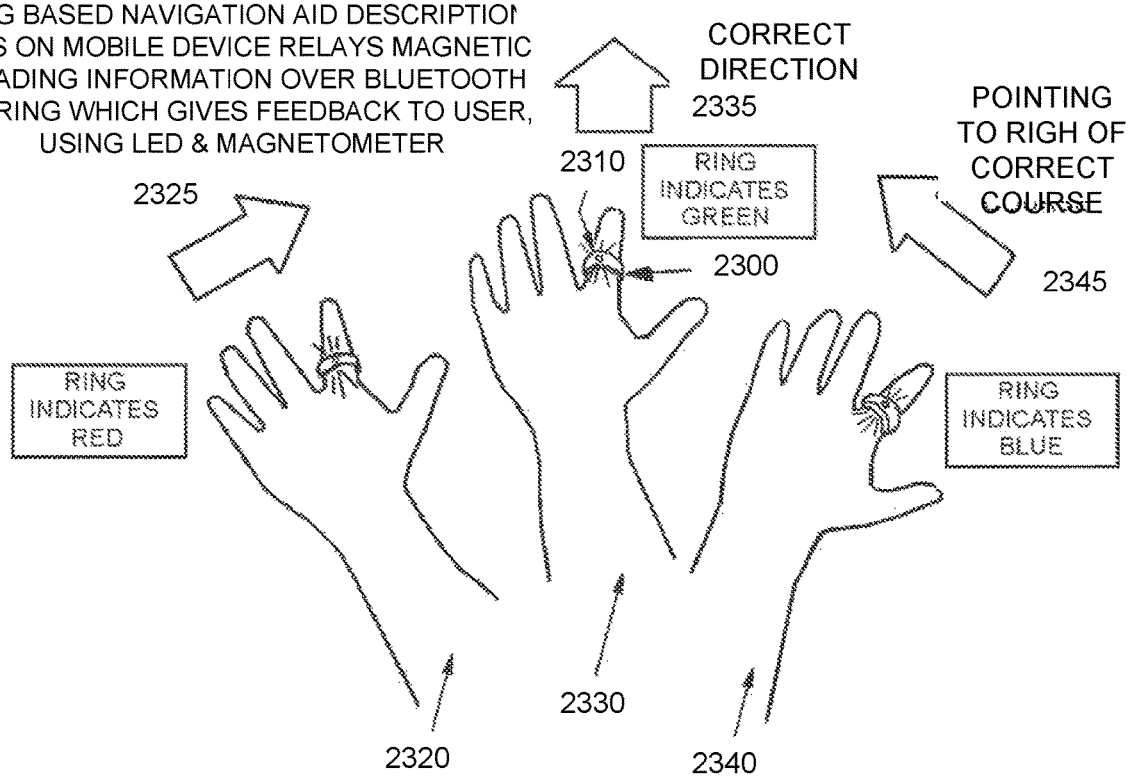
FIGS. 18A-B are embodiments employing the navigational features of the WCD.

FIG. 18A is a perspective view of the hand of a user in various positions employing the navigational features of the WCD. As described above, the WCD can communicate with a mobile device though one or more wireless communication protocols. The mobile device can include a processor and a memory and can execute a map application/process that can provide turn-by-turn walking or driving directions to the user based on the user's GPS location. A portion of those directions can include information regarding heading, distance to travel at that heading, waypoints, and the direction of next turn. By way of the wireless communication, the mobile device can communicate one or more of pieces of information relating to directions, such as the heading. Once the heading is received the WCD, the WCD can give feedback to the user regarding the actual heading measured by the onboard magnetometer and the heading set forth in the direction information. In one example, the feedback can be haptic or physical feedback provided by one or more actuators, such as the actuators 670 described above.

FIG. 18A depicts a user's hand in various positions of navigation, each hand including a WCD worn thereon. In this example, the heading provided by the mobile device is the heading 2335, which represents the direction in front of the hand position 2330. In this regard, if the user gestures, e.g., points a ring finger, in the direction of the correct heading, the WCD 2300 can give feedback to the user indicating the correct heading. The feedback can include, for example, an LED indicator 2310 showing a green visible light. In the example of hand position 2320, the finger is gesturing in a direction to the left of the correct course 2325. In this way, the WCD 2300 can provide feedback to correct the heading of the user. Such feedback can include illumination of an LED indicator showing (e.g.) a red visible light. Similarly, hand 2340 is gesturing in direction 2345, which is to the right of the correct/appropriate direction. The WCD can provide (e.g.) a blue indicator informing the user to change heading.

Figure 18B:
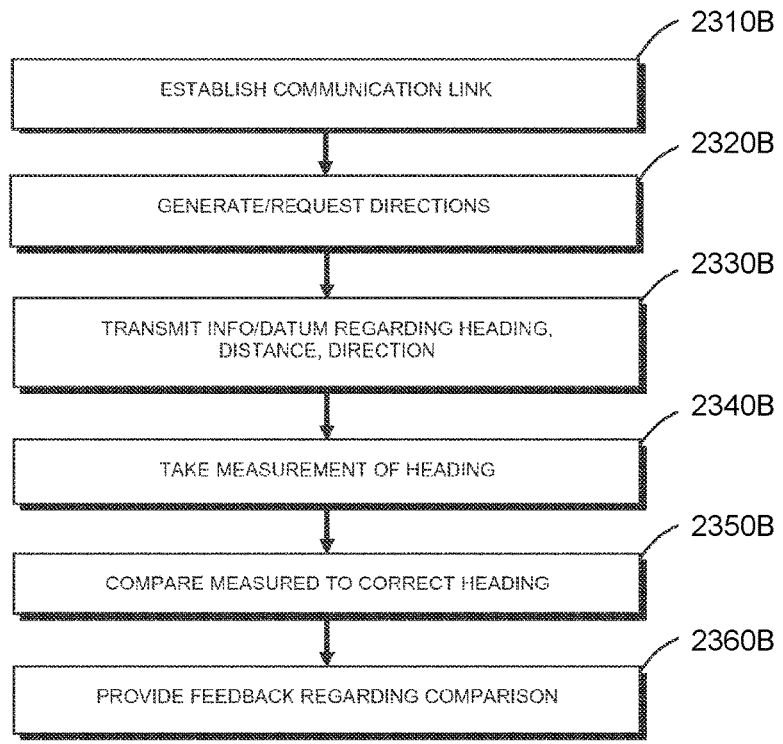

FIG. 18B is a flow chart 2300B depicting a method of providing feedback to a user according to one or more aspects of the disclosure. At block 2310B, a user can establish a communication link between a WCD and a mobile device. At block 2320B, the user can generate or request a set of directions at the mobile device, including information/data regarding heading, distance to travel at that heading, and the direction of next turn. At block 2330B, the mobile device can transmit at least one of the information items/datum regarding heading, distance to travel at that heading, and the direction of next turn. At 2340B, the WCD can take a measurement of heading by measuring a heading associated with an explicit gesture by the user's finger donning the ring. Such gesture can include pointing in a proposed heading of travel. At block 2350B, the WCD can compare the measured or proposed heading to the correct heading provided by the mobile device. At 2360B, the WCD can provide feedback to the user based on the comparison at 2350B, e.g., if the user is gesturing in the correct direction, a green LED indicator may appear. In other examples, if the gesture is in a direction that does not correspond with the correct direction, a (e.g.) blue or red indicator can appear. In one specific example, indicators representing left and right course alterations can be different so a user can easily discern a correct direction of travel.

Figure 19A:
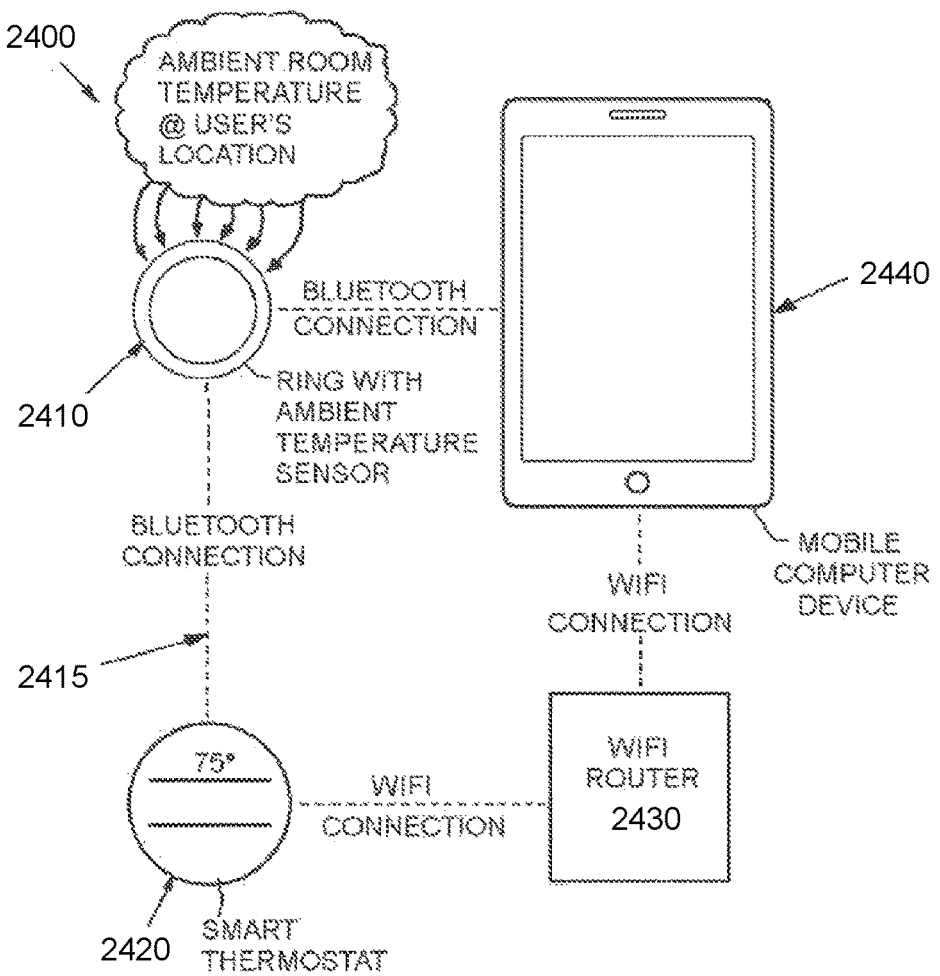

FIG. 19A is a schematic diagram of a system 2400 for controlling an environment of a user according to one or more aspects of the disclosure. As shown, the WCD can be connected, wired or wirelessly, to one or more appliances in the home of a user. The system 2400 can include a WCD 2410, a thermostat 2420, a wireless access point (e.g., WiFi router) 2430, and a mobile device 2440. The WCD can be wirelessly connected (e.g., link 2415) to both the thermostat and the mobile device by any type of wireless communication protocol, such as Bluetooth. The access point can be wirelessly connected to the thermostat and the mobile device by any type of wireless communication protocol, such as WiFi. It is noted that a wide range of commercially available appliances, thermostats, lighting controllers, home controllers, and the like, can interface with the WCD using WiFi or another conventional/proprietary communication protocol, as described further below.

Figure 19B:
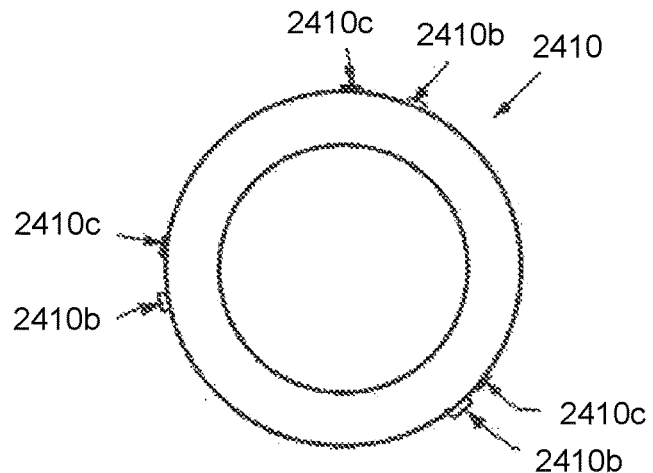

The WCD 2410 can include one or more temperature sensors. In one example, the WCD can include at least one internal facing temperature sensor 2410a and an at least one outward facing temperature sensor 2410b, as shown at FIG. 19B. The inward facing temperature sensor 2410a can be near the skin of a user when the user is wearing the ring, and can therefore measure the skin temperature of the user. The outward facing temperature sensors 2410b can be disposed away from the finger of the user, and can therefore be arranged to measure an ambient temperature of the room in which the user currently resides with sufficient thermal isolation from the user's hand and his/her body heat. In particular, in order to ensure accurate ambient temperature measurements, the WCD can employ a combination of multiple light sensors 2410c and outward facing temperature sensors 2410b. In this regard, the temperature sensor 2410b associated with the light sensor 2410c that receives the most light can be the most accurate, as it is most likely that this sensor is furthest from the finger or palm of the user. In another example, the WCD can employ multiple outwardly facing temperature sensors 2410b and compare the temperature values of each to the inward facing sensor 2410a. The WCD can then select the most accurate temperature value from the outward facing sensors.

Based on the measured skin temperature and measured ambient temperature, the WCD can automatically adjust the thermostat 2420 to alter the ambient temperature of the room. In this regard, if a user's skin temperature is too high, the WCD can instruct the thermostat 2420 to lower the ambient temperature. Similarly, if the user's skin temperature is too cold, the WCD can instruct the thermostat 2420 to raise the temperature. The WCD 2410 can instruct the thermostat (and/or an HVAC controller) directly, e.g., via a direct wireless link 2415, or indirectly, e.g., via one or more of the mobile device 2440 and the access point 2430. The WCD can also use historic temperature data to develop trend temperature data.

In another example illustrated in FIG. 19C, the WCD can be part of a system 2400C for controlling home appliances. The system 2400C can include a WCD 2410C, one or more home appliances 2420C, and an access point 2430C. Such home appliances 2420C can include, for example, a television, lights, speakers, microwave, range, stove, oven, etc. Each of the home appliances can include an antenna that allows the respective home appliances to communicate wirelessly with one or more access points 2430C. In one example, the appliances can include a ScenSor DW 1000 chip provided by DecaWave. In this way, the locations of the appliances in the room can be determined to an accuracy of approximately 10 cm. The location of the WCD 2410C can also be determined, using the above-referenced chip, or by using signal strengths of one or more base stations.

Having established the position of one or more home appliances and the user in a room, the user can make a gesture to control such home appliances 2420C. For example, the user can point at the TV (while wearing the WCD) in order to turn it on/off. Knowing the position of the user and the position of the TV, the direction of the gesture and the type of gesture can indicate what action to take on which device. The accelerometer and/or magnetometer on the WCD can be used to create a vector to the object to control, and a wireless packet can bet sent to a wireless access point to control the respective appliance.

FIG. 19D is a flow chart depicting a method 2400D of controlling home appliances according to one or more aspects of the disclosure. At block 2410D, the locations of one or more home appliances in a room and/or house can be ascertained/determined. As described above, the appliances can include a processor configured to identify location within a room. At block 2420D, the location of the WCD is determined. At block 2430D the user can make a gesture toward a home appliance to exert control over the home appliance. Such gesture can include a snap, a point, etc. At block 2440D, the accelerometer and/or magnetometer on the WCD can be used to create a vector to the object to control. At block 2450D, a wireless packet can bet sent to a wireless access point to control the respective appliance. The access point can then issue the command to the respective appliance.

FIG. 20 is a perspective view of the hand of a user employing a two-factor authentication technique according to one or more aspects of the disclosure.

As shown, the user 2500 is wearing a WCD 2510 and is approaching a locked door 2520 with an access node 2530 associated therewith. The access node 2530 can be a wireless access node of a conventional or custom arrangement, and can communicate wirelessly according to any type of wireless protocol, such as WiFi or Bluetooth. As the user approaches the door 2520, the WCD 2510 can initiate a communication link, e.g., Bluetooth or WiFi, with the access node 2530. In this way, the WCD and the access node can engage in one or more handshaking or query procedures to verify the WCD. For example, the access node 2530 can detect a MAC address, IP address, or other alphanumeric identifier associated with the WCD and compare it to a list of authorized users. Such network-based communication processes should also be clear to those of skill.

Once the MAC address or other identifier is verified, the user can engage in a pre-defined gesture 2550 to complete the authentication procedure. The gesture 2550 can be any type of hand and/or finger motion that can be performed by the user. In this regard, the accelerometer or magnetometer can detect the gesture 2550 performed by the user and provide the gesture information to the access node. If the provided gesture information corresponds with an authorized gesture stored at or accessible by the access node, then the user may be granted authorization and the door can be unlocked. The authorized gesture can be a general authorized gesture for all users, or can be a specific gesture authorized only for the particular MAC address.

In addition to a door, the method above can be used to gain access to other features, such as unlocking a mobile phone, unlocking a car door, starting a car. The authentication technique above is advantageous in that it can eliminate extraneous authentication devices, such as key fobs for a car, a door, keypads for entry control, etc., and can provide a secure two-factor authentication technique to avoid unwanted access. More generally any type of keyless entry system (e.g. a keypad, card-reader, keyless lock, etc.) can be equipped with appropriate communication interfaces (RF, IR, etc.) to communicate with the WCD and operate based on a gesture and/or proximity of the user using the techniques described above. The WCD can also be employed generally in this manner to activate or deactivate a residential or commercial alarm system substituting, for example, for a key fob used for this purpose.

Figure 21A:
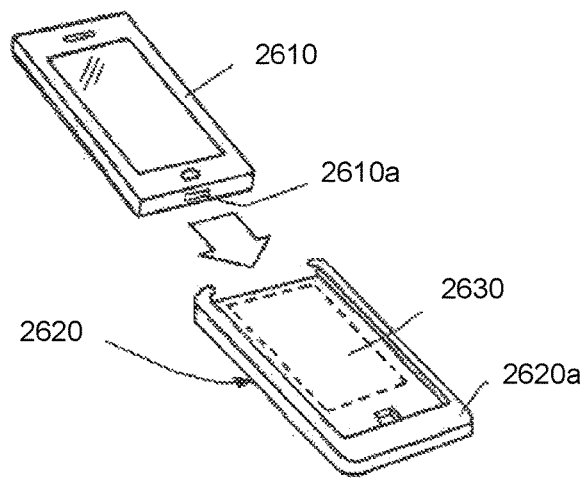
FIGS. 21A-D illustrate embodiments for charging according to one or more aspects of the disclosure.

FIG. 21A is a schematic view of a charging apparatus for charging the WCD according to one or more aspects of the disclosure. As shown, a mobile device 2610 can be received within a case 2620. The mobile device 2610 can be electrically connected to the case 2620 via a port 2610a on the mobile device 2610 and a connector 2620a on the case 2620. As shown in phantom, the case 2620 can include an integrated battery 2630 within the case that can charge the mobile device via the connector or can charge a WCD, as will be described in greater detail below.

Figure 21B:
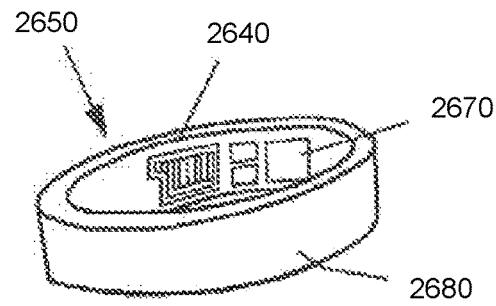
Figure 21C:
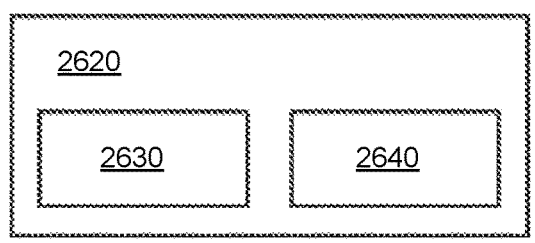

The integrated battery can be connected to an antenna 2640 disposed on or within the case 2620 that can emit an RF signal, as shown in the block diagram in FIG. 21C. The RF signal can have a power of less than 500 mW and a frequency of 13.56 MHz. The RR signal can be emitted in all directions around the case such that it can be received by a WCD in proximity to the case.

Figure 21D:
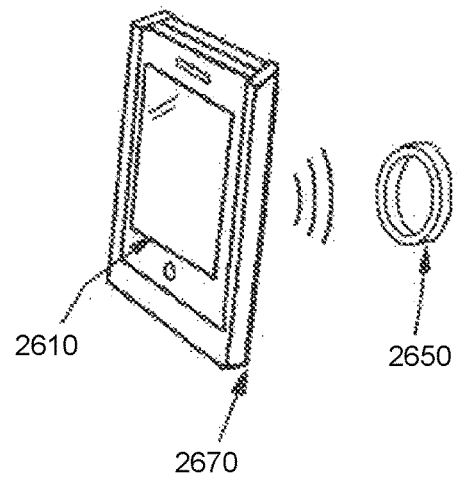

FIG. 21B shows a WCD 2650 including an RF antenna 2660 and charging circuitry 2670. The RE antenna 2640 can be disposed within the housing 2680 and can receive the RF signal emitted by the case 2620 and convert it to a current that can be used to charge the WCD battery (not shown). This can advantageously allow the user to charge the WCD without removing the WCD from the finger. As shown in FIG. 21D, the charging can occur whenever the WCD is in close proximity to the case, such as when a user talking on the phone or merely handling the phone. In another implementation, the case can utilize inductive charging to charge the WCD. In this regard, the case can include an induction coil subjected to a predetermined current to produce a magnetic field. A corresponding induction coil within the housing of the WCD can be subjected to the magnetic field to produce a current that can charge the onboard battery in accordance with known electromagnetic principles.

Figure 22A:
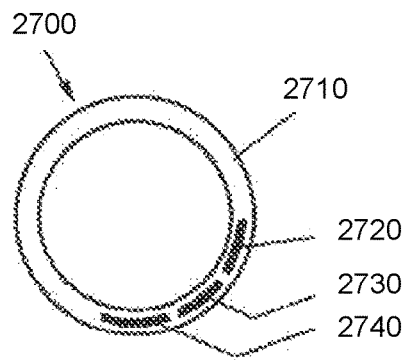
FIGS. 22A-B illustrate embodiments according to one or more aspects of the disclosure.
Figure 22B:
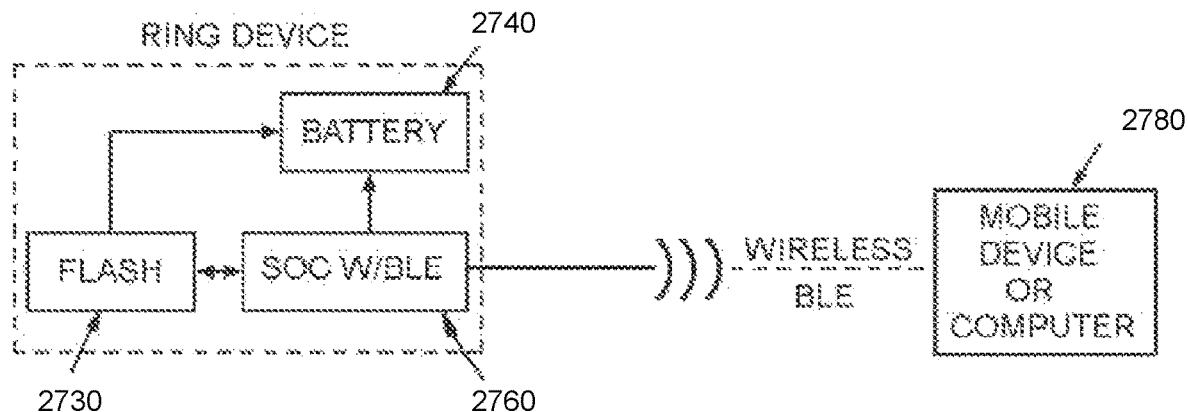

FIG. 22A is a pictorial diagram and FIG. 22B is a block diagram of a WCD employing flash storage according to one or more aspects of the disclosure. As described above, the WCD 2700 can include a housing 2710, an antenna 2720, and an integrated circuit (IC) 2730 including a flash memory 2740. The IC and the flash memory can be disposed within the housing 2710. The flash memory 2740 can be powered by a battery 2750 and connected to the IC 2730, which can be implemented as a system-on-a-chip (SoC) IC 2760. The IC can include Bluetooth Low Energy (BLE) capability to allow for communication with another device. The flash memory can be used to store data, or can be used in any of the authentication techniques described above. The WCD can transmit data stored on the flash memory to another device 2780 via the BLE connection, or can receive data and store the data on the flash memory.

Figure 23A:
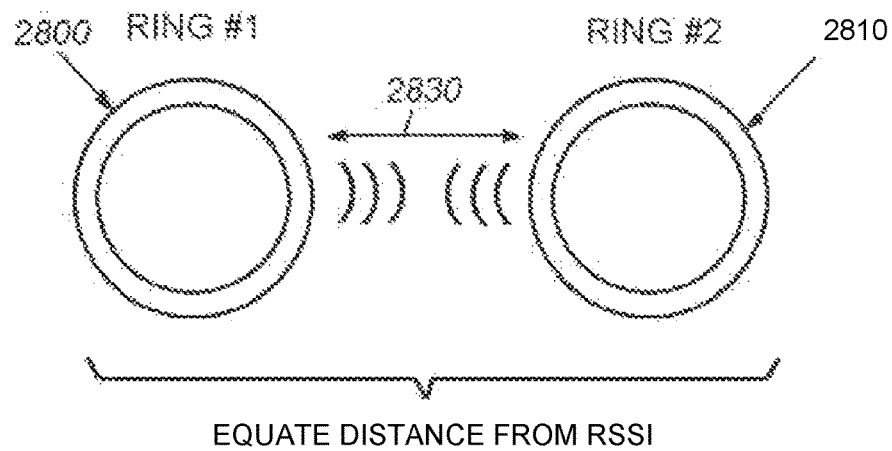
FIGS. 23A-B illustrate WCDs performing proximity functions according to one or more aspects of the disclosure.

FIG. 23A is a schematic diagram of one or more WCDs performing proximity functions according to one or more aspects of the disclosure. The WCD can detect a strength of an RF signal received by its antenna, and calculate a distance to the source of the RF signal using a Received Signal Strength Indicator (RSSI). In one example, the RF signal can be from a mobile device, an access point, or another WCD. The use of RSSI can have many applications in proximity detection. For example, the WCD can be placed on a child and can be connected to mobile device held by a parent. If the WCD travels a predetermined distance from the mobile device, the WCD can issue an alert to the mobile device, thereby alerting the parent that the child has wandered too far. In another example, the parent can wear a first WCD and the child can wear a second WCD. The first WCD can alert the parent that a child has wandered too far.

A single user can wear a first WCD 2800 on a first finger on a first hand and a second WCD 2810 on a second finger on a second hand. In this regard, the user can measure the relative distance between the first and second fingers using an RSSI via a wireless link 2830 between the WCDs 2800, 2810, such as a BLE connection. This can be used to measure an approximate dimension of an object held in both hands or to estimate a mid-air measurement.

In some examples, a first user can wear a first WCD 2800 and a second user can wear a second WCD 2810. The RSSI can be collected over a period of time and the processor can analyze the data to develop trends or statistics. For example, the RSSI data can indicate that the first and second users have spent a certain amount of time together and can serve as a relationship monitor.

Figure 23B:
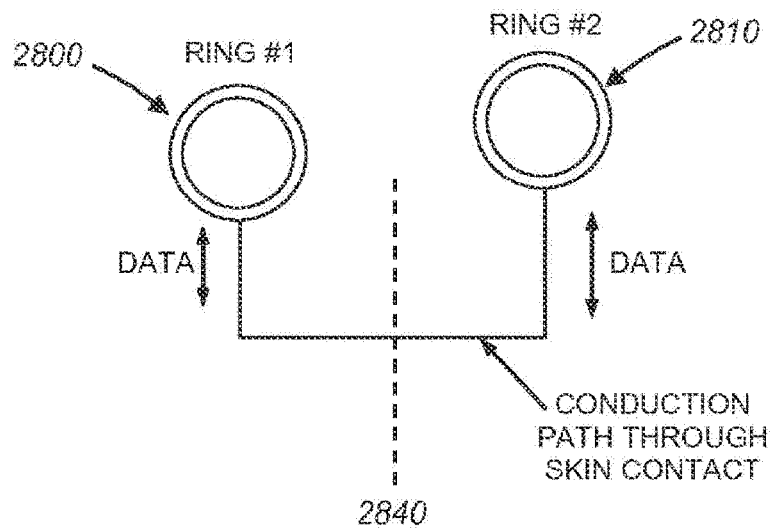

The WCD can also detect when the first user and second user are holding hands. FIG. 23B is a schematic diagram of one or more WCDs 2800, 2810 performing proximity functions according to one or more aspects of the disclosure. Similar to the ECG monitoring techniques described above, a circuit can be formed when the users hold hands 2840 (with the respective hands wearing the WCDs). The circuit can be used to transmit data and/or electrical impulses between the respective WCDs via the circuit. The WCDs can collect data regarding the length of time that the users are holding hands and, in combination with the amount of time spent together, monitor the relationship of the two users. In addition, the WCD can collect data regarding communication between the users, e.g., e-mail, social media, etc. Based on all of the above factors, the WCD can develop a relationship score between respective WCD users, with a higher relationship score indicating more and more frequent interactions.

Figure 24A:
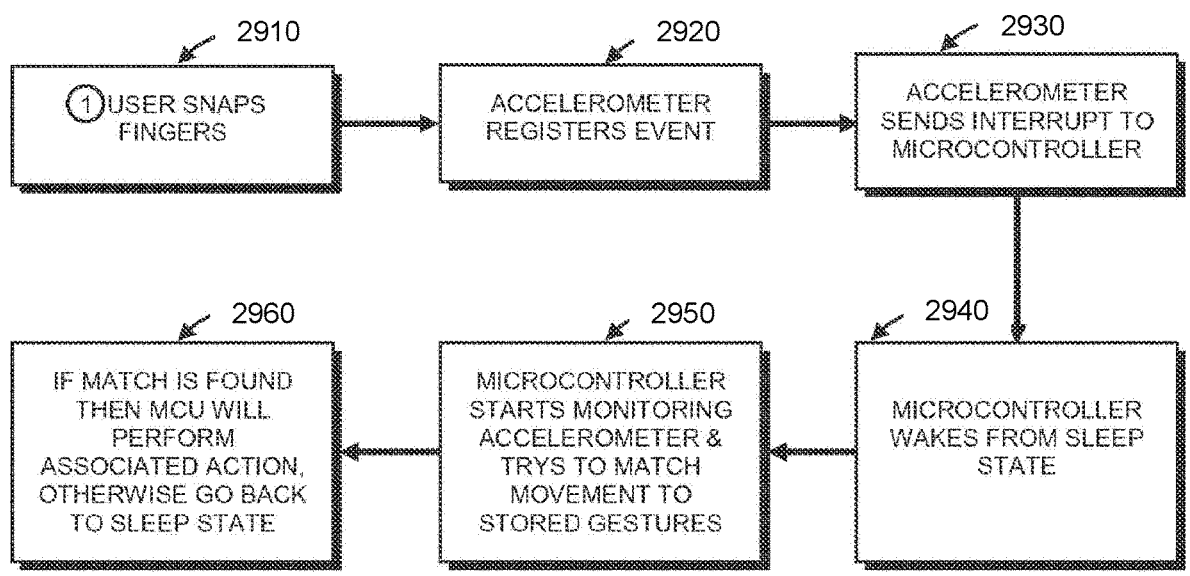
FIGS. 24A-B illustrate gesture inputs according to one or more aspects of the disclosure.

FIG. 24A is a flow chart depicting a method of initiating gesture input according to one or more aspects of the disclosure. The WCD can be used to perform one or more commands, or to instruct another device, such as a mobile device, to perform one or more commands. Such commands can include, initiate sleep state of WCD, initiate sleep mode or default mode of WCD, powering off/on of the WCD, turning on/off an LED light of the WCD, powering on/off of a mobile device, placing a phone call on the mobile device, etc. The user can establish one or more custom gestures to initiate any of the commands above. For example, the user can select a command to be customized from a number of commands. Once selected, the user can perform a custom gesture to be associated with that command. In some examples, the user can perform the custom gesture multiple times to allow the WCD to better identify the gesture and to develop error tolerances for registering the gesture.

At block 2910, the user can perform a first gesture. In this example, the user can perform a finger snap. At block 2920, WCD can register the gesture, via the accelerometer and/or the magnetometer. At block 2930, the accelerometer can send an interrupt signal to the processor. At block 2940, the processor can wake from a sleep or default system state. At block 2950, the processor can monitor the accelerometer for a second gesture, at which point the user can perform a second gesture. If the second gesture matches a gesture in the gesture command database, then the WCD can perform the associated command. If not, the WCD can return to the sleep state.

Figure 24B:
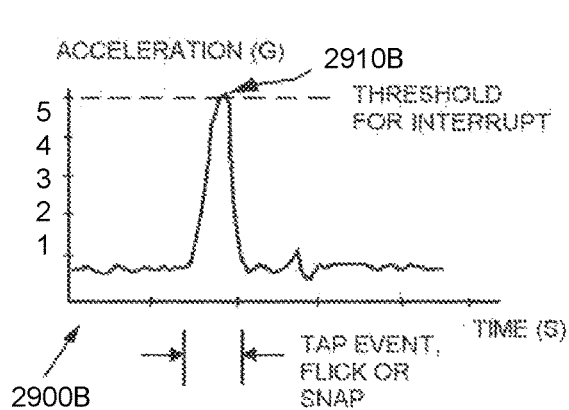

FIG. 24B is a chart 2900B showing an exemplary graph of acceleration vs. time as measured by the accelerometer of the WCD. As shown at peak 2910B, the gesture can only be registered if it reaches a predetermined acceleration threshold. If the gesture performed at 2910 meets the threshold, it can proceed to block 2930 where the interrupt procedure is performed.

Figure 25:
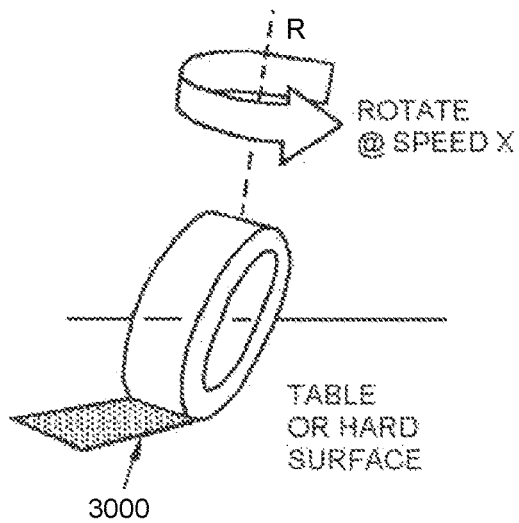
FIG. 25 is a perspective view of a WCD 2000 employing a reset function.

FIG. 25 is a perspective view of a WCD 3000 employing an illustrative reset function and associated procedure/process. As shown, the WCD 3000 can be removed from the finger of the user in order to initiate a system reset of the WCD. In one example, the system reset can be initiated by spinning about a rotation axis R at a predetermined speed. The predetermined speed can be any value, and in one example is a rotational velocity. Upon performing the reset procedure at the predetermined speed, operation of the WCD 3000 can be interrupted and the onboard components of the 3000 can power off, and revert to factory default settings. Additionally, a series of movements can initiate a rest, such as putting the ring on a table and turning it over several times.

Figure 26A:
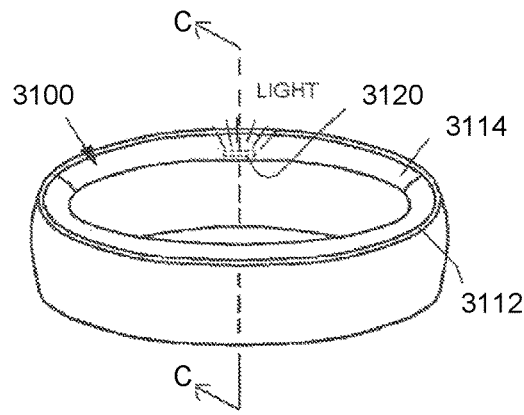
FIGS. 26A-C are views of a WCD including an LED indicator according to one or more aspects of the disclosure.

FIG. 26A is a perspective view of a WCD including an LED indicator according to one or more aspects of the disclosure. As shown, the WCD 3100 can include an internal/external housing 3112 and an internal/external potting 3114. The WCD can include an LED 3120 that can be visible through the internal/external potting 3114.

Figure 26B:
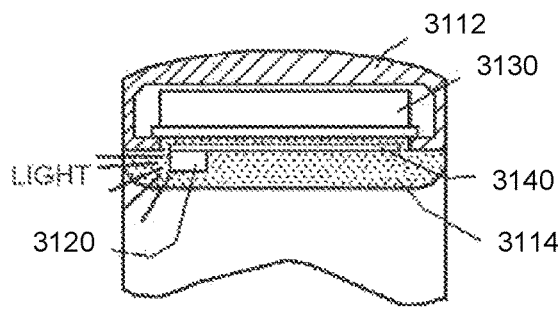
Figure 26C:
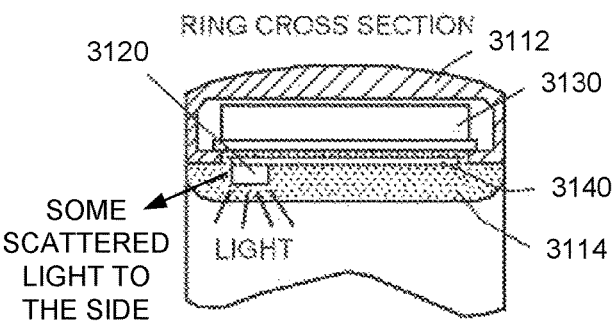

FIGS. 31B and 31C are cross sections along line C-C of a WCD employing an LED indicator according to one or more aspects of the disclosure. As described above, the WCD 3100 can have an internal and/or external potting 3114 that can be transparent. This allows light sources within the housing to pass through the potting without changing, or with minimal change to, the optical properties of the light. In this way, a light source 3120, such as an LED, can be disposed on the PCB 3140 and can be powered at least partially by battery 3130. The LED can be encapsulated by the potting 3112 and can project light through the potting 3112. As shown in FIG. 26B, the LED 3120 can include a vertical LED, while 31C depicts a right angle LED. The vertical LED can project light along direction L1, while the right angle LED can project light along direction L2. When light is projected along L2, the light can travel around a circumference of the finger of the user. Note that, according to aspects of the disclosure, the potting can be generally adapted in whole or in part to condition, filter or modify the wavelengths and/or projection qualities of light by for example, embedding lensmatic components, applying light-diffusive additives, light attenuating filter materials, etc.

Figure 27:
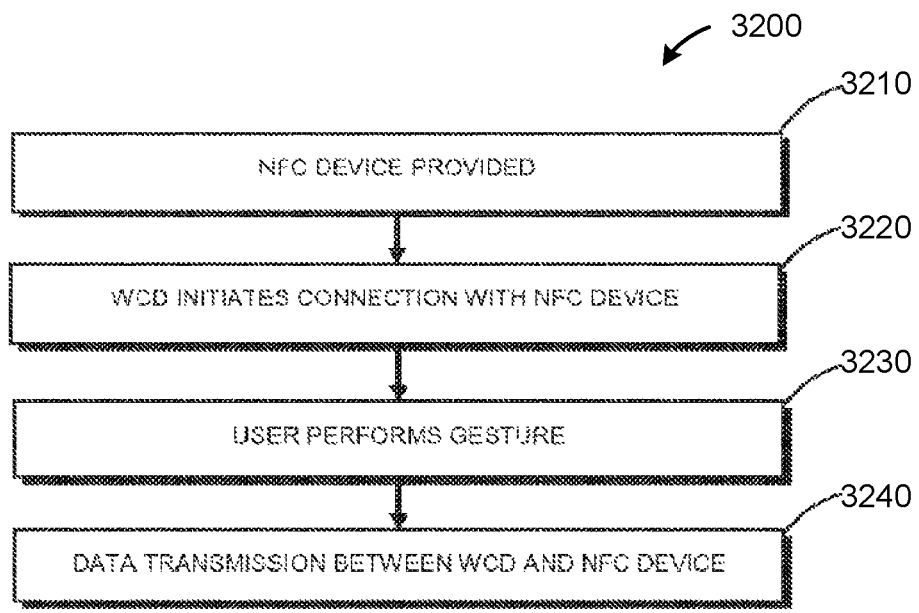
FIG. 27 is flow chart depicting a method of communicating with a near field communication (NFC) device according to one or more aspects of the disclosure.

FIG. 27 is flow chart depicting a method 3200 of communicating with a near field communication (NFC) device according to one or more aspects of the disclosure.

In some examples, the WCD can enable or disable NFC or change the functionality of a NFC device. For example, the WCD can itself engage in NFC with another computing device, or the WCD can be connected via wireless link to a computing device that engages in NFC with a different computing device. In certain existing NFC devices, NFC will connect and begin transmitting data as soon as it is queried. In the present example, NFC is enabled or begin transmitting data exclusively upon performing of a predetermined gesture. However, a variety of other transmission processes can be implemented—for example a periodic chirp or handshake request by the WCD for communication with appropriate devices.

At block 3210, a NFC capable device is provided. The device can be any type of device, such as a laptop, tablet, mobile device, or dedicated NFC device.

At block 3220, the WCD initiates a connection with the NFC device. The connection can be a direct connection via NFC, or an indirection connection via an intermediate device. At this point, no data has yet been transmitted between the WCD and the NFC device.

At block 3230, a user performs a predetermined gesture that is registered by the WCD. The gesture can be any type of gesture, such as a point, a snap, waving the hand, etc.

At block 3240, data transmission begins between the NFC device and the WCD.

In other examples, the user can perform another gesture to cease NFC communication. The gesture can be the same gesture as described above or a different gesture. Additionally, the user can remove the ring to disable the NFC. Upon donning the ring the user will be prompted by the application on the mobile device to re-authenticate by entering a PIN, whereby the proper PIN results in re-enabling the NFC functionality.

In yet another example, the WCD device employing NFC can be configured on the fly to map to different data sets stored thereon. For example, the WCD device employing NFC can employ data thereon to make purchases, e.g., account information, data to access a building, e.g., a key fob, and data thereon to board public transportation, e.g., smart card, metro card, etc. A user can perform a predetermined different gesture for each of the above data sets to access the data. Once accessed, the WCD device employing NFC can initiate a link with another computing device to initiate a transaction, to open a door, or to board public transportation, etc.

Figure 28:
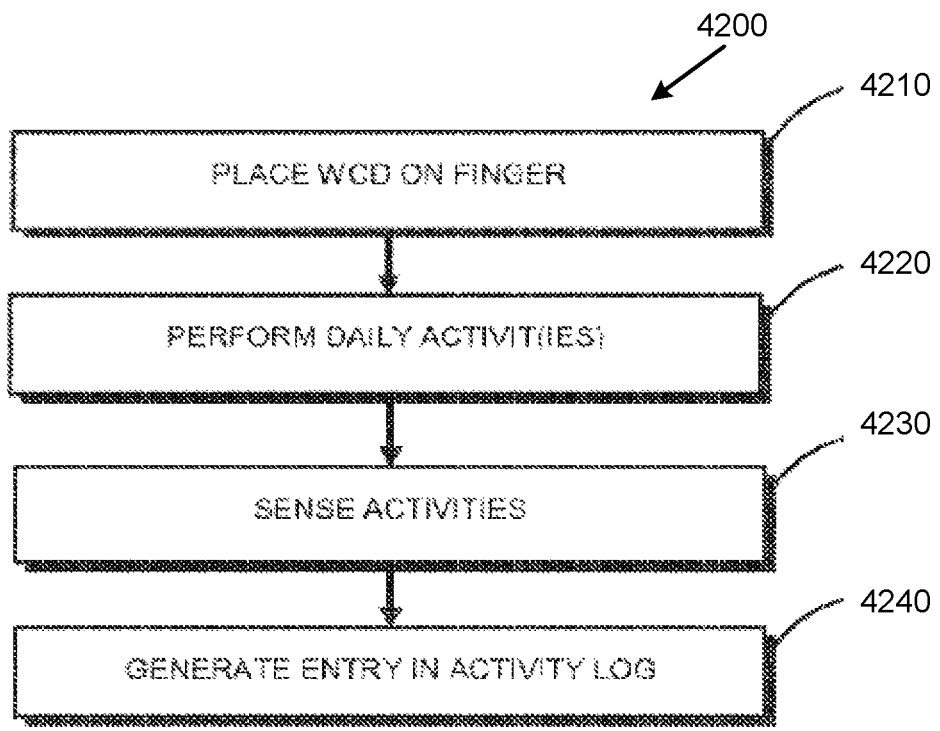
FIG. 28 depicts a method of monitoring activity according to one or more aspects of the disclosure.

FIG. 28 depicts a method 4200 of monitoring activity according to one or more aspects of the disclosure.

At block 4210, a user can don or place the WCD onto the finger to secure it in the wearing position.

At block 4220, a user can perform any number of daily activities, such as running on a treadmill, walking, exercising, typing, etc.

At block 4230, the WCD, contemporaneous with block 3220, can use one or more sensors to sense the activities of the user. For example, the sensors can detect location, speed, acceleration, orientation, heart rate, etc.

At block 4240, the WCD, or another computing device, can generate an entry in an activity log at the conclusion of a detected activity. If the activity detected by the sensors has a profile that has not yet been identified, the WCD can prompt the user to identify the activity. For example, the user can identify profiles such as "Run in Central Park," "Typing," "Run on Treadmill," etc. The WCD can associate the identity provided by the user with the activity profile identified by the sensors and store the identified activity in the WCD memory, or any other memory. Later, if the user performs the same activity and the WCD detects the activity profile as being similar to a saved activity, the WCD can identify the activity while the user is performing the activity and save the activity in the activity log. Each of the activities performed can be saved in the overall activity log and can be stored in a memory on the WCD, or other device, for later viewing.

Figure 29:
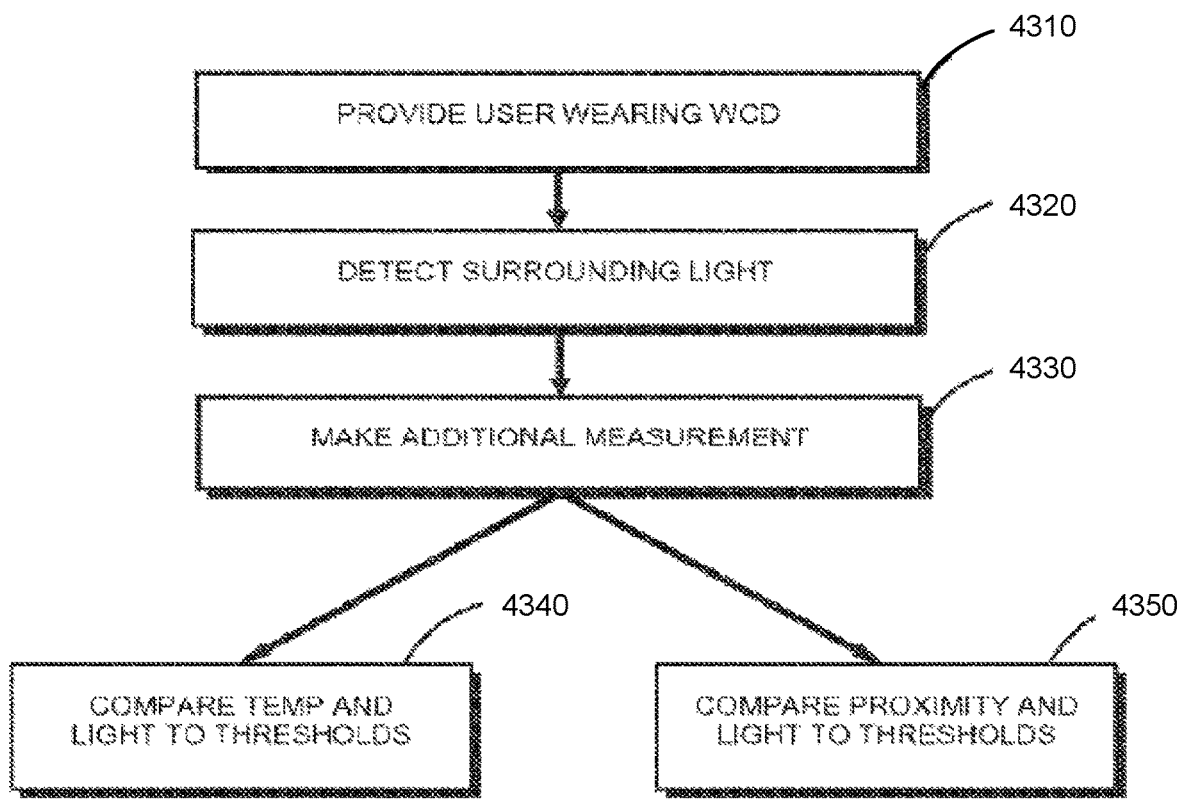
FIG. 29 depicts a method of determining whether a user is wearing gloves according to one or more aspects of the disclosure.

FIG. 29 depicts a method 4300 of determining whether a user is wearing gloves according to one or more aspects of the disclosure. At block 4310, a user is provided while wearing the WCD, where such user may or may not be wearing gloves.

At block 4320, one or more light sensors on board the WCD can detect surrounding ambient light. Such light sensors could include, for example, a CPV or other light sensitive element.

At block 4330, one or more additional measurements maybe made. Such additional measurements can include, for example, an ambient temperature measurement and or a proximity measurement, e.g., detecting proximity of an object to the WCD via reflected electromagnetic radiation in the form of IR light.

At block 4340, a measured ambient temperature and ambient light measurements are compared to predetermined thresholds. If the ambient temperature measurement is above a certain predetermined temperature threshold and the ambient light measurement is below a certain threshold, it can be determined that the user is wearing a glove over the WCD.

At block 4350, a measured proximity and ambient light measurements are compared to respective predetermined thresholds. If the proximity measurement is below a certain distance threshold (e.g., determines an item is in close proximity to the WCD) and the ambient light measurement is below threshold, it can determined that the user is wearing a glove over the WCD. In any of the above examples, an intensity of LED indicators of the WCD can be adjusted according to a detected ambient light using an appropriate algorithm or process that compares the ambient light to a scale and adjusts a desired driving current/voltage for the LEDs according to a predetermined formula (e.g. a proportional adjustment using an adjustment coefficient) or scale (e.g. a lookup table). For example, where there is abundant ambient light (e.g., detected ambient light above a predetermined threshold), the intensity of the LED indicators can be increased. In the same way, where there is little ambient light (detected ambient light below a predetermined threshold), the intensity of the LED indicators can be decreased.

In one example, the WCD can detect whether it is removed and or installed on the finger of the user. In this regard, as mentioned above, the WCD can have inward-facing light sensors, CPV, or temperature sensors. When a user installs a ring on his finger the measure of ambient light may decrease or the temperature may increase. Such changes in ambient light and/or temperature can be detected by one or more sensors onboard the WCD and a determination can be made that the user has removed and or installed the ring on his finger.

Figure 30:
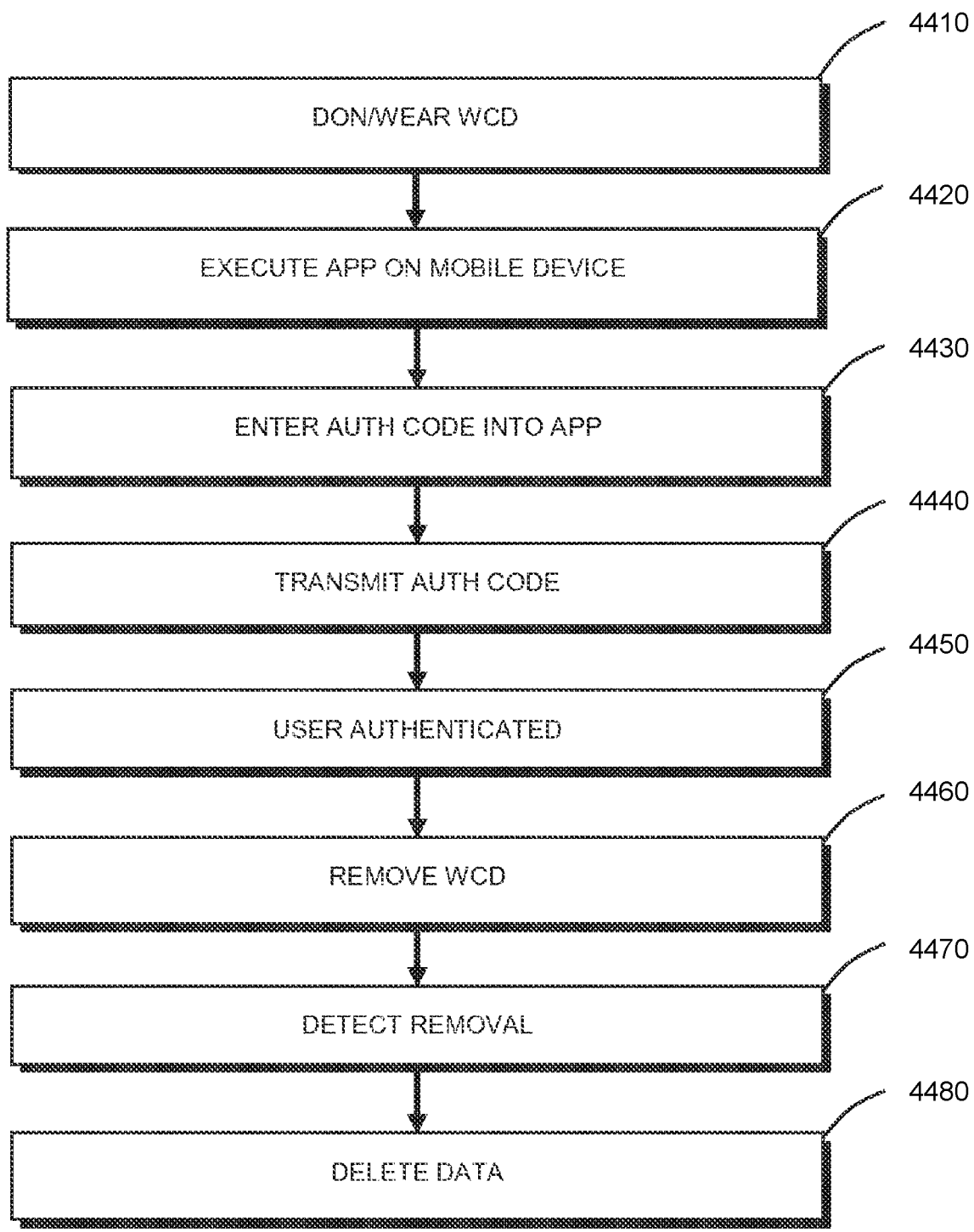
FIG. 30 depicts a method of securing data onboard the WCD according to one or more aspects of the disclosure.

FIG. 30 depicts a method 4400 of securing data onboard the WCD according to one or more aspects of the disclosure. At block 4410, a user may don the WCD on the finger. At block 4420, a user may execute an application on a mobile device, or other computing device, that can be previously associated and authenticated with the WCD. At block 4430, the user can enter an authorization code into the application running on the mobile device, such as a PIN code. At block 4440 the mobile device may transmit the authorization code to the WCD by any means of communication, such as, wired, wireless, Bluetooth, NFC, etc. At block 4450, the user wearing the WCD can now be again authenticated and associated with the WCD and can be granted access to certain functions and/or data storage of the WCD. At block 4460 a user may remove the WCD. At block 4470 the WCD can detect that it is removed such as bio detection (including e.g., biometric identification) techniques described above with respect to inward facing sensor changes, temperature changes, or heart rate decreasing to zero. At block 4480, the authorization code previously stored on the WCD can be automatically deleted upon detection of removal to avoid unauthorized access to such information by a subsequent wearer or other querying party. Further or alternatively, additional information can be automatically deleted upon removal of the WCD, for example any data and or instructions stored on the onboard memory of the WCD such as personal information, banking information, confidential information, or other sensitive data.

Figure 31:
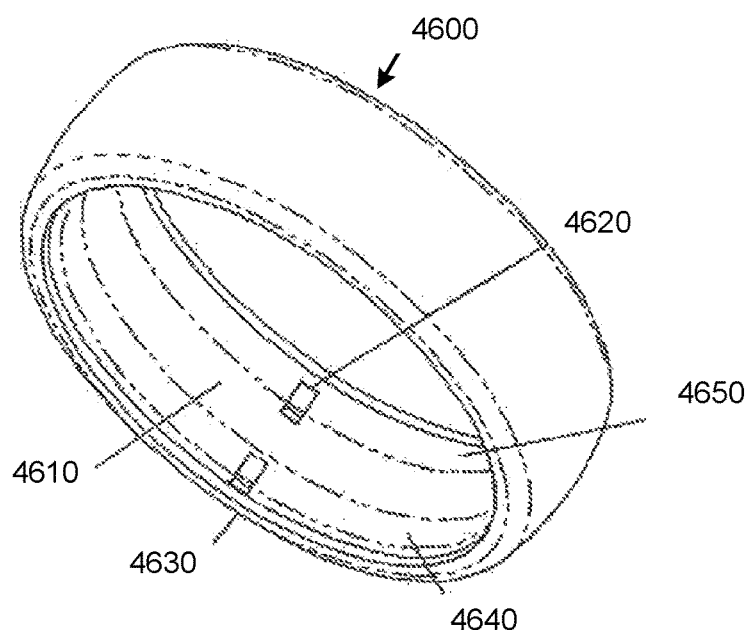
FIG. 31 depicts a WCD with a pair of LED indicators disposed at an inward-facing portion of the WCD.

FIG. 31 depicts a WCD 4600 with a pair of LED indicators 4610-4620 disposed at an inward-facing portion of the WCD. As shown, the WCD 4600 can include a pair of transparent regions 4640-3650 and an opaque region 4630. The LEDs 4610-3620 can be positioned under the transparent regions 4640-3650 to allow light from the LEDs to exit the WCD. In one example, the LEDs 4610-3620 can create a subtle diffuse glow to the skin to provide a desirable visual effect to user. In another example, a user feedback LED can be placed at an inward facing surface and a second can be placed at an outward facing surface of the WCD. Depending on the circumstances, one of the LEDs may be disabled to save battery life. For example, LEDs that are facing away from a user e.g. facing down or away from user's line of sight, may be disabled. As described above, the WCD can determine its orientation based on onboard sensors, such as the magnetometer, accelerometer, GPS, etc.

Figure 32A:
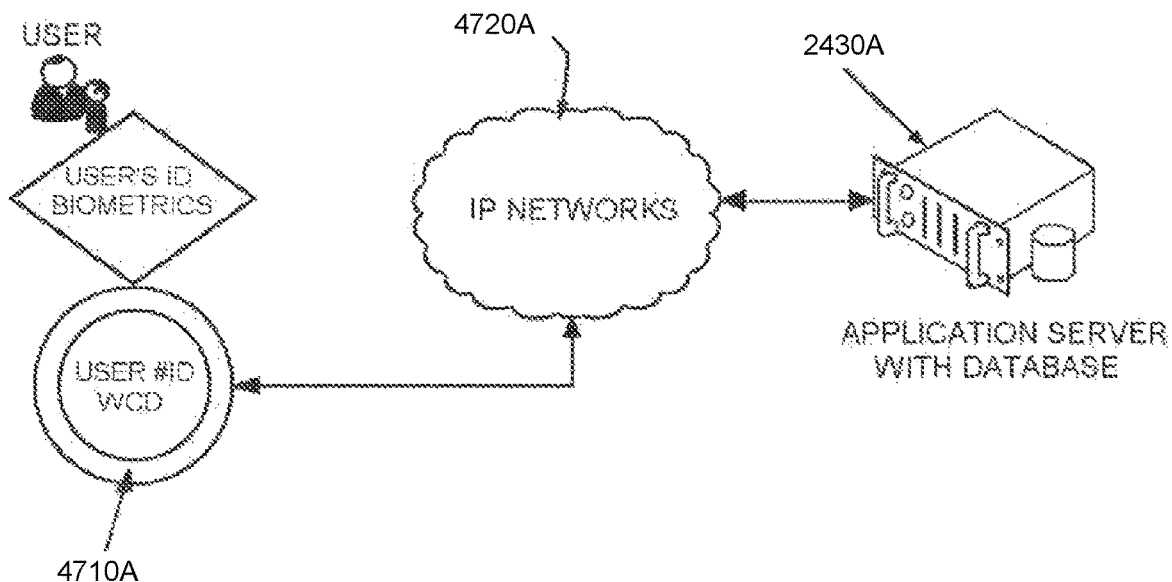
FIGS. 32A-C are alert embodiments according to one or more aspects of the disclosure.

FIG. 32A is a system for generating and managing alerts according to one or more aspects of the disclosure. As shown, the system can include a WCD 4710A, one or more networks 4720A, and one or more server computers 4730A according to one or more aspects of the disclosure. The WCD 4710A can communicate directly and/or indirectly with the server 4730A via the network 4720A. In this regard, data generated and/or stored at the WCD 4710A can be transmitted to the server 4730A and vice versa. In one example, such data can include biometric data pertaining to a user wearing the WCD that is detected and stored by the WCD.

Figure 32B:
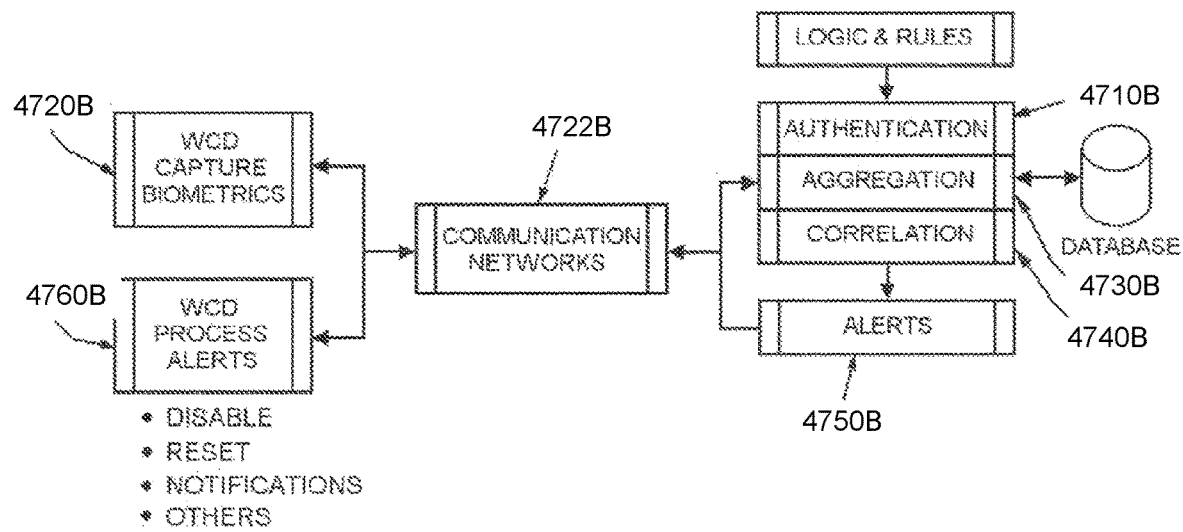
Figure 32C:
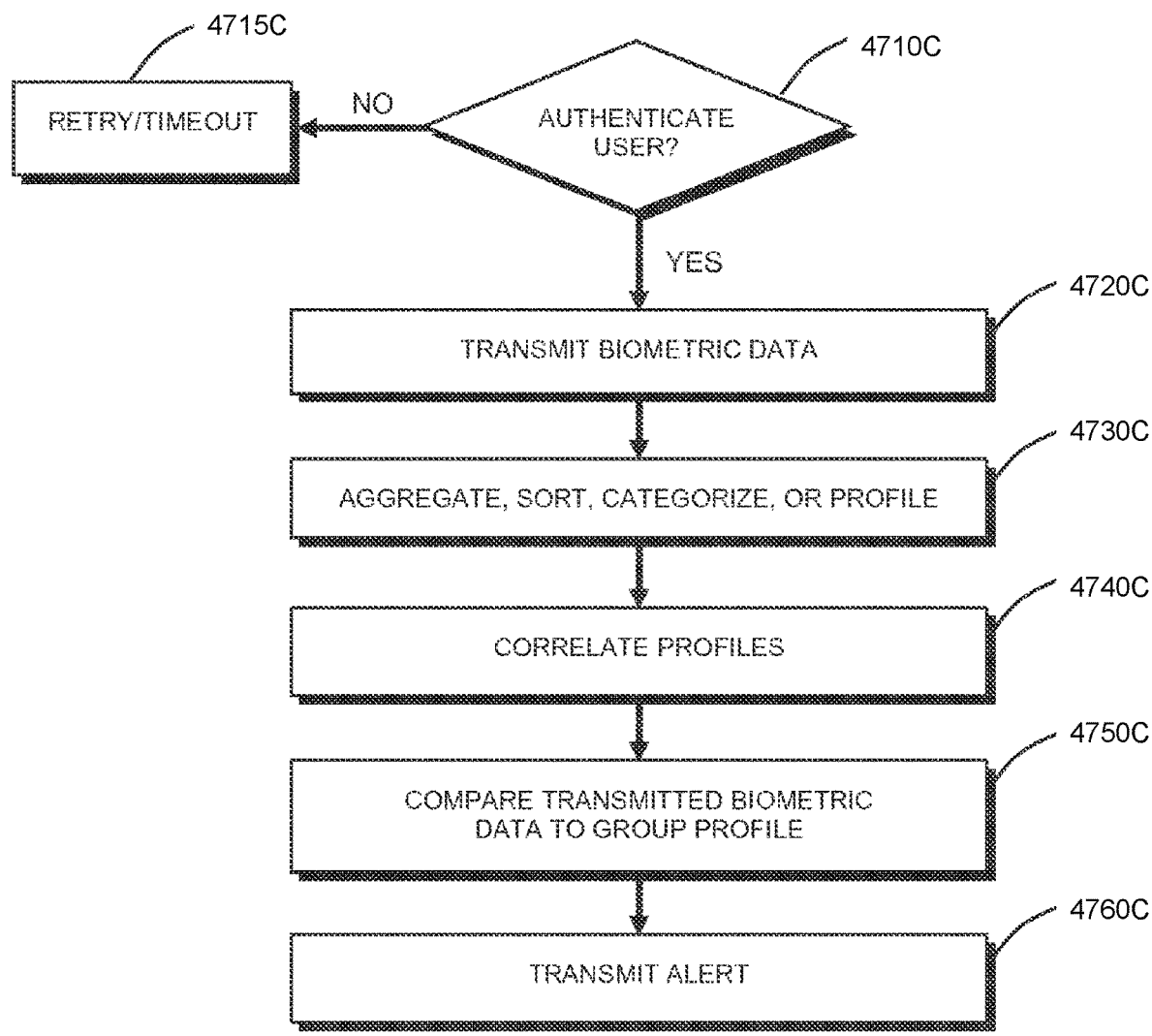

FIG. 32B depicts a block process diagram for generating and managing alerts according to one or more aspects of the disclosure and FIG. 32C is a flow chart depicting a method for generating and managing alerts according to one or more aspects of the disclosure.

At block 4710C, and as shown at process block 4710B, the user is authenticated with respect to the WCD. In this regard, a single user can be associated with a single WCD and can be associated with a predetermine identifier, such as an alphanumeric number. If the user is not authenticated or the authentication process is not conclusive, the WCD may invite the user to retry authentication at block 4715C until the user is successfully authenticated. In some examples, the WCD may timeout the authentication process, lock the WCD, or place the WCD in safe mode in the event of too many unsuccessful authentication attempts as a security measure.

The user can be authenticated according to any of the authentication methods described in the present application, such as via a unique capillary map, a unique ECG profile, etc.

If the user is authenticated, biometric data can be transmitted to the server at block 4720C. The captured biometric data 4720B can be transmitted to the server via network 4720A, 47222B

Once received at the server, the biometric data can be aggregated, sorted, categorized, or profiled at block 4730C and as shown at process block 4730B. In this regard, a profile (corresponding to the alphanumeric identifier) may be created at a database at the server that stores data for a particular user. The profile can store transmitted biometric data, as well as other data, such as user gender, height, weight, age, family history, disease information, location, etc.

In some examples, identifying information may be removed from the data and/or not transmitted to allow for anonymity and/or to comply with regulations regarding transmission of medical data. The transmitted biometric data can be normalized in order to comply with predetermined data requirements in order to be added to the profile. In one example, a minimum amount of data may be required in order to be considered viable for association with the profile. The biometric data of a single profile can be aggregated, or in other examples multiple profiles can be aggregated simultaneously.

Aggregation of the user's biometric data into a single profile allows for the profile to be visualized or analyzed according to any number of methods. For example, a timeline can be created showing biometric data over a period of time. The data can also be synthesized or analyzed to calculate trend data, or other mathematical features.

Although only one WCD is depicted, it is contemplated that a plurality of WCDs can exist, with each WCD corresponding to a distinct user (and distinct alphanumeric identifier) and therefore resulting in a plurality of distinct profiles at the server. Accordingly, each of the distinct users/WCDs may be authenticated separately according to the methods described herein.

At block 4740C, once the transmitted data has been associated with the user profile, the updated profile can be correlated with one or more other profiles stored at the server as shown as process block 4740B. The profiles may be correlated according to any number of correlation standards, such as correlating users with similar traits such as age, gender, location, profession, or by any other data stored at the server. In some examples, one or more of the traits can be used to make such a correlation. The biometric data from the one or more users that are correlated with one another can be combined to form a group profile. The group profile can be the aggregation, average, range, or sum of individual profiles that form the group profile. For example, for a particular group profile, a range of resting heart can be generated by taking the maximum and minimum values of resting heart from the individual profiles. In other examples, an average (and standard deviation or standard deviation of the mean) can be generated for each trait, such as average resting heart rate, average active heart rate, average blood pressure, average blood sugar, average skin temperature, ECG profiles, as well as any other features capable of being detected by the WCD as described above.

At block 4750C, transmitted biometric data can be compared to the established values from the group profile. In this way, if a user's heart rate deviates by a predetermined threshold (such as by predetermined magnitude or standard deviation), an alert can be generated at process block 4750B. The comparison process can occur at the server after transmission of the biometric data. In another example, the group profile data can be transmitted to the WCD for comparison at the WCD. This advantageously allows the comparison to be made where the WCD cannot establish a network link. The group profile can be updated on a continuous basis or a predetermined time interval or at each transmission of biometric data.

At block 4760C, the alert is transmitted to the WCD and displayed to the user at process block 4760B. The alert, can indicate that the user's biometric data has deviated from the profile group and may advise the user to seek medical attention. In another example, the server can directly contact a medical health professional. In the example where block 4750C occurs at the WCD, transmission of alert information from the server may not be necessary.

The alert at the WCD can be any type of audio or visual indicator, such as an LED, haptic feedback, audible alarm, etc. The indicator may also invite the user to rest, make an appointment with a medical health professional, recommend a particular medication, or suggest certain physical activities that may health condition that caused the alert.

As shown in FIG. 32B, the authentication 4710B, aggregation 4730B, and correlation 4740B can occur at server 4730A, which can include a process, memory, and any other features of a general purpose computer. The authentication 4710B, aggregation 4730B, and correlation 4740B can access a database stored at the memory, where profiles, group profiles, and biometric data can be stored.

Figure 33A:
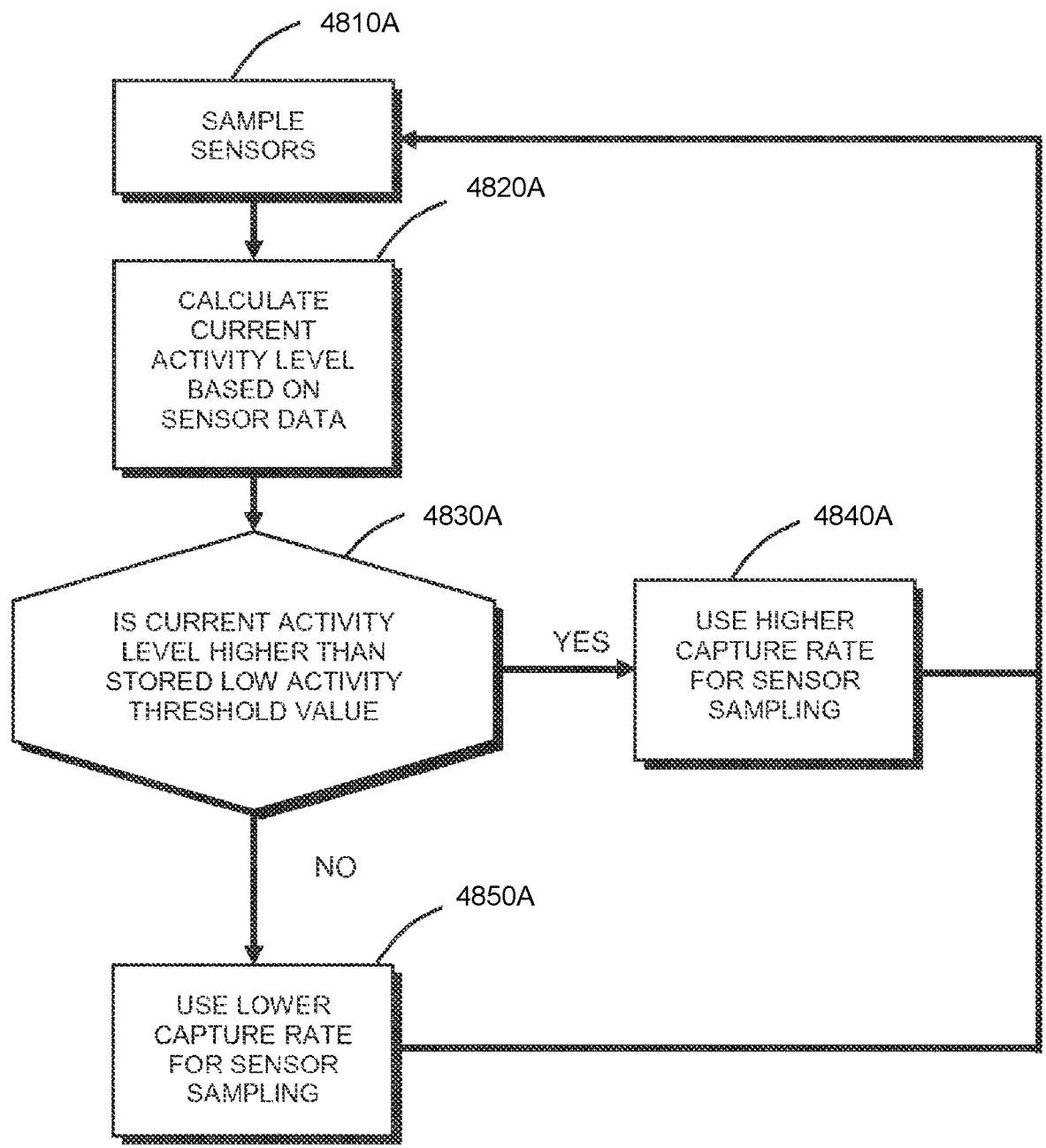
FIGS. 33A-C are sampling embodiments according to one or more aspects of the disclosure.

FIG. 33A is a method for variable sampling according to one or more aspects of the disclosure. As described above, the processor module of the WCD can determine (e.g., based on identified physical activities, routine pattern, and/or time) a frequency at which one or more sensors in the sensor modules should operate.

At block 4810A, one or more sensors of the WCD may take one or more measurements. For example, the WCD can detect temperature, heart rate, acceleration, as described above.

At block 4820A, the WCD can calculate an activity level of a user. For example, the WCD can compare to a number of stored activity profiles (as described above) stored by the user, or can compare the sensor measurements to sensor threshold values corresponding to different activities, such as sitting, running, sleeping etc. In one example, the WCD detect acceleration values over time to generate an activity level for a particular time period.

At block 4830A, the WCD may compare the identified activity level to a predetermine activity threshold value. In one example, the WCD may categorize the detected activity as either a high level activity or a low level activity. High level activities can include running, swimming, biking etc., while low level activities may include sitting, standing still, or sleeping.

At block 4840A, the WCD can set a first sample rate for high level activities and at block 4850A, the WCD can set a second sample rate for low level activities. The first sample rate can be a shorter time interval than the second sample rate, resulting in more data being detected and generated during a set amount of time while the user is active. This allows for increased power efficiency of the WCD while also providing the advantage of generating more data when a user is more active, thereby providing added biometric data for later analysis.

In another example, the sample rate can be scaled according to activity level. For example, the sample rate can be scaled to be directly proportional to heart rate. This results in a shorter time interval for sampling (more frequent data gather) for running than for walking.

As activity level changes, the method above can be repeated a plurality of times at certain intervals in order to quick or abrupt activity changes.

Figure 33B:
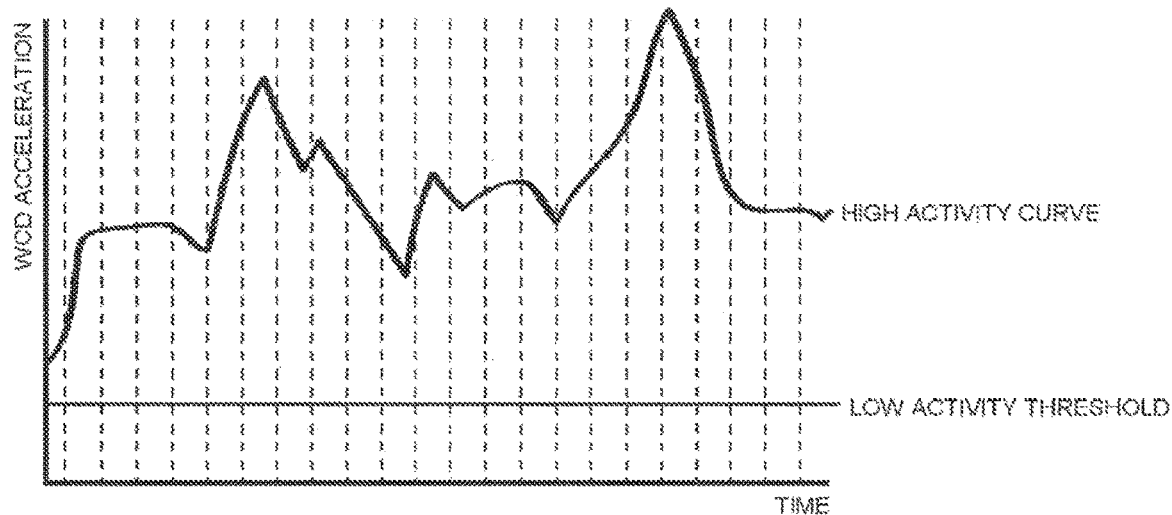
Figure 33C:
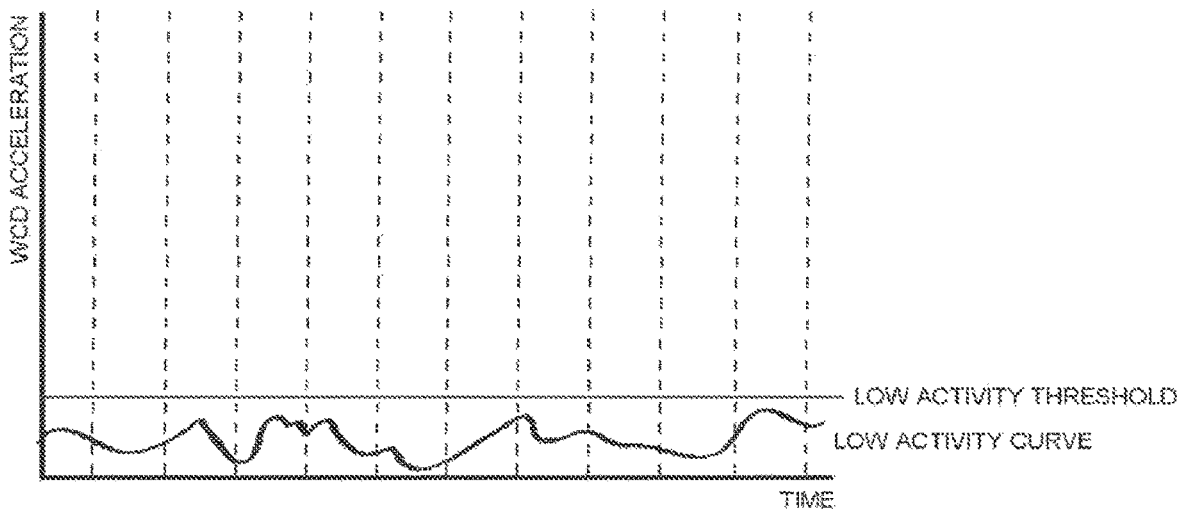

FIGS. 33B and C are graphs depicting one or more aspects of the sample method of FIG. 33A. As shown in FIG. 33B, the WCD may determine a user is engaging in a high level activity by detecting acceleration values that are above a predetermined threshold value. In this regard, a shorter time interval (more frequent data gathering) can be set. As shown in FIG. 33C, the user is engaging in a low level activity since the acceleration values are below a predetermined threshold. A longer sample rate (less frequent data gathering) can be set in this instance.

Figure 34:
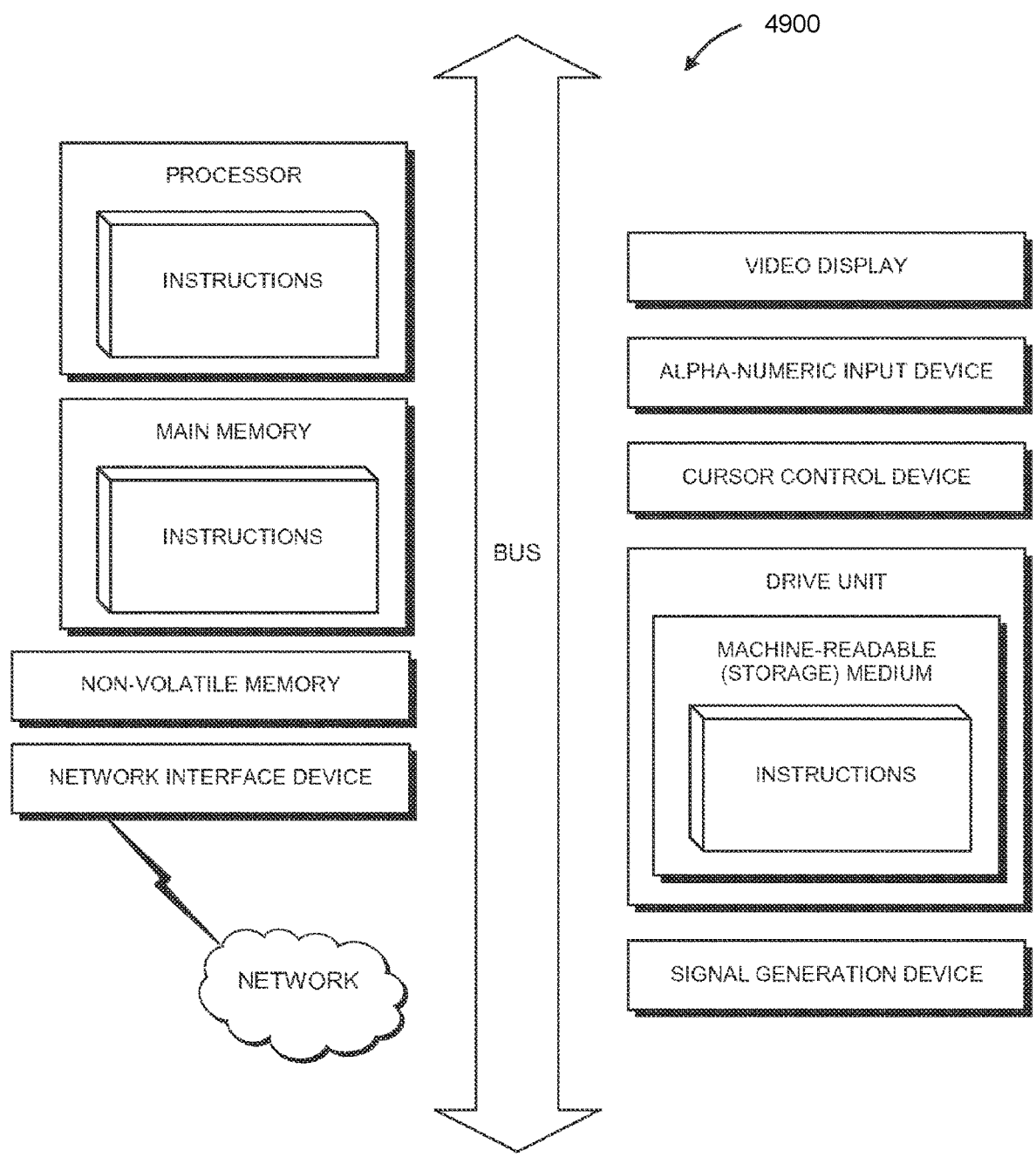
FIG. 34 is a diagrammatic representation of a machine in the example form of a computer system within which a set of instructions, for causing the machine to perform any one or more of the methodologies discussed herein, may be executed.

FIG. 34 a diagrammatic representation of a machine in the example form of a computer system 4900 within which a set of instructions, for causing the machine to perform any one or more of the methodologies discussed herein, may be executed. Specifically, FIG. 34 shows a diagrammatic representation of a machine in the example form of a computer system within which instructions (e.g., software or program code) for causing the machine to perform any one or more of the methodologies discussed herein may be executed. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute instructions to perform any one or more of the methodologies discussed herein.

The example computer system includes a processor (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory, and a non-volatile memory, which are configured to communicate with each other via a bus. The computer system may further include graphics display unit (e.g., a plasma display panel (PDP), a liquid crystal display (LCD), a projector, or a cathode ray tube (CRT)). The computer system may also include alphanumeric input device (e.g., a keyboard), a cursor control device (e.g., a mouse, a trackball, a joystick, a motion sensor, a touch screen, or other pointing instrument), a storage unit, a signal generation device (e.g., a speaker), and a network interface device, which also are configured to communicate via the bus.

The storage unit includes a non-transitory machine-readable medium on which is stored instructions embodying any one or more of the methodologies or functions described herein. The instructions may also reside, completely or at least partially, within the main memory or within the processor (e.g., within a processor's cache memory) during execution thereof by the computer system, the main memory and the processor also constituting machine-readable media. The instructions may be transmitted or received over a network via the network interface device.

While machine-readable medium is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium that is capable of storing instructions for execution by the machine and that cause the machine to perform any one or more of the methodologies disclosed herein. The term "machine-readable medium" includes, but not be limited to, data repositories in the form of solid-state memories, optical media, magnetic media, or other non-transitory machine readable medium.

Conclusion

It should be clear that the WCD arrangements described according to various aspects of the disclosure provide a highly versatile and useful item of wearable electronics that is comfortable and convenient to wear, conveniently charged, and weatherproof for all-purpose and all-condition wearing. Various options for style and appearance can be implemented, as well as a variety of storage options. The functions and structure of the device lend themselves to both a ring version and a wrist-worn version. All versions are designed for long-life with minimal maintenance, and are adaptable to intemperate with a variety of networked devices including computers, smartphones, home controllers, security systems, and virtually any other device capable of communicating over a wireless link—including another WCD or TCD.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein various directional and orientational terms such as "vertical", "horizontal", "up", "down", "bottom", "top", "side", "front", "rear", "left", "right", and the like, are used only as relative conventions and not as absolute orientations with respect to a fixed coordinate system, such as the acting direction of gravity. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process, application, and/or processor here herein can be implemented using electronic hardware, software consisting of a non-transitory computer-readable medium of program instructions, or a combination of hardware and software. Also, while a variety of visible and near-visible radiation sources are described as LEDs, it is expressly contemplated that other types of sources can be employed according to aspects of the disclosure—for example plasma discharge sources and bioluminescent sources, as well as sources that are based upon developing technologies. Electronic circuits and RF components can similarly be based on alternate and/or developing technologies. Accordingly, this description is meant to be taken only by way of example, and not to otherwise limit the scope of this invention.

We claim:

1. A wearable computing device configured to be worn around a finger of a wearer comprising:
    an external housing having an outer surface, an interior surface and sidewalls, wherein the interior surface and the sidewalls are characterized by approximately a C-shaped cross section and define an interior space, and wherein the interior space is configured to retain a plurality of components;
    wherein the plurality of components comprises:
    a curved rechargeable battery disposed within the interior space of the housing, wherein the rechargeable battery is curved to conform to the interior surface;
    a printed circuit board disposed within the interior space configured to approximately conform to the interior surface;
    one or more sensors disposed upon the printed circuit board, wherein the one or more sensors are selected from a group consisting of: an accelerometer, a gyroscope, and a motion sensor, wherein the one or more sensors are configured to sense physical perturbations and to output sensed data;
    a memory disposed upon the printed circuit board, the memory configured to store one or more executable instructions;
    a short-range communication module disposed upon the printed circuit board, the short-range communications module configured to communicate a first set of data to a client computing device via a first communications protocol;
    a first temperature sensor configured to provide first temperature data associated with a temperature of a wearer of the wearable computing device;
    a processor disposed upon the printed circuit board and coupled to the battery, the one or more sensors, the memory, the short-range communication module, and the first temperature sensor, wherein the processor is configured to receive the sensed data, is configured to perform the one or more executable instructions in response to the sensed data, and is configured to direct the short-range communication module to output data to the client computing device; and
    a potting material disposed in the interior space encapsulating the plurality of components, wherein the potting material forms an interior wall of the wearable computing device, wherein the potting material is substantially transparent to light selected from a group consisting of: visible light, infrared light, and ultraviolet light.

2. The wearable computing device of claim 1
    wherein the printed circuit board comprises a plurality of rigid circuit boards coupled via flexible regions; and
    wherein adjacent rigid circuit boards from the plurality of rigid circuit boards form an angle therebetween, enabling the adjacent rigid circuit boards to approximately conform to the interior surface.

3. The wearable computing device of claim 2
    wherein the plurality of rigid circuit boards comprises a first rigid circuit board, a second rigid circuit board and a third rigid circuit board, wherein the second rigid circuit board is disposed between the first rigid circuit board and the third rigid circuit;
    wherein the computing device further comprising:
    an infrared light source disposed upon the first rigid circuit board, wherein the infrared light source is configured to illuminate a portion of skin of the finger with infrared light; and
    an imaging device disposed upon the second rigid circuit board, wherein the imaging device is configured to receive reflected light from the portion of the skin in response to the infrared light.

4. The wearable computing device of claim 1 wherein the potting material is selected from a group consisting of: silicone, epoxy, polyester resin, and a polymer.

5. The wearable computing device of claim 4 wherein the housing material comprises a metal is selected from a group consisting of: a metal alloy, stainless steel, tungsten carbide, a titanium alloy, silver, platinum and gold.

6. The wearable computing device of claim 1 wherein the first temperature sensor is selected from a group consisting of: a thermistor, a positive temperature coefficient thermistor, a negative temperature coefficient thermistor, and an infrared sensor.

7. The wearable computing device of claim 6 further comprising a second temperature sensor configured to provide second temperature data associated with an ambient temperature.

8. The wearable computing device of claim 1 further comprising:
    a module disposed upon the printed circuit board and coupled to the curved rechargeable battery and to the processor, wherein the module is configured to manage power to and from the curved rechargeable battery.

9. The wearable computing device of claim 8 further comprising:
    an external electromagnetic inducting charging mechanism configured to output a magnetic field; and wherein the plurality of components also comprises an electromagnetic induction charging coil configured to be disposed proximate to the external electromagnetic inducting charging mechanism, wherein the electromagnetic induction charging coil is configured to receive the magnetic field in a direction normal to the interior surface of the external housing.

10. The wearable computing device of claim 1
wherein a width of the external housing is within a range of 3 mm to 8 mm; and
wherein a thickness of the wearable computing device is within a range of 1.5 to 3 mm.

11. The wearable computing device of claim 1
wherein the short-range communication module is selected from a group consisting of near field communication (NFC), and Bluetooth; and
wherein the output data comprises authentication data associated with the client computing device.

12. The wearable computing device of claim 1
wherein the one or more sensors are configured to sense the physical perturbations at a first detection frequency or a second detection frequency; and
wherein the processor is configured to direct the one or more sensors to change detection frequency from the first detection frequency to the second detection frequency in response to the sensed data.

13. The wearable computing device of claim 12
wherein the processor is configured to determine a plurality of temperatures associated with the wearer with respect to time in response to the first temperature data; and
wherein the processor is configured to direct the short-range communication module to output the plurality of temperatures associated with the wearer with respect to time to the client computing device.

14. A wearable computing device configured to be worn around a finger of a wearer comprising:
an external housing having an outer surface forming an exterior wall of the wearable computing device, an interior surface and sidewalls, wherein the external housing is characterized by approximately a C-shaped cross section and define an interior space, and wherein the interior space is configured store a plurality of components;
wherein the plurality of components comprises:
a curved rechargeable battery disposed within the interior space of the housing, wherein the rechargeable battery is curved to conform to a curvature of the interior surface;
a printed circuit board comprising a plurality of rigid circuit boards coupled via flexible regions, wherein the printed circuit board is disposed within the interior space and piecewise linearly conforms to the curvature of the interior surface;
one or more sensors disposed upon the printed circuit board, wherein the one or more sensors are selected from a group consisting of: an accelerometer, a gyroscope, and a motion sensor, wherein the one or more sensors are configured to sense physical perturbations and to output sensed data;
a memory disposed upon the printed circuit board, the memory configured to store one or more executable instructions;
a short-range communication module disposed upon the printed circuit board, the short-range communications module configured to communicate a first set of data to a client computing device via a first communications protocol;
a first temperature sensor configured to provide first temperature data associated with a temperature of a wearer of the wearable computing device;
a processor disposed upon the printed circuit board and coupled to the battery, the one or more sensors, the memory, the short-range communication module, and the first temperature sensor, wherein the processor is configured to receive the sensed data, is configured to perform the one or more executable instructions in response to the sensed data, and is configured to direct the short-range communication module to output data to the client computing device; and
a potting material disposed in the interior space encapsulating the plurality of components, wherein the potting material forms an interior wall of the wearable computing device, wherein the potting material is substantially transparent to light selected from a group consisting of: visible light, infrared light, and ultraviolet light.

15. The wearable computing device of claim 14
wherein adjacent rigid circuit boards from the plurality of rigid circuit boards form an angle therebetween, enabling the adjacent rigid circuit boards to approximately conform to the curvature of the interior surface;
wherein the plurality of rigid circuit boards comprises a first rigid circuit board, a second rigid circuit board and a third rigid circuit board, wherein the second rigid circuit board is disposed between the first rigid circuit board and the third rigid circuit;
wherein the wearable computing device further comprises:
a first infrared light source disposed upon the first rigid circuit board, wherein the first infrared light source is configured to illuminate a first portion of skin of the finger with infrared light;
a second infrared light source disposed upon the third rigid circuit board, wherein the second infrared light source is configured to illuminate a second portion of skin of the finger with infrared light; and
an imaging device disposed upon the second rigid circuit board, wherein the imaging device is configured to receive reflected light from the first portion of the skin and the second portion of the skin.

16. The wearable computing device of claim 14
wherein the potting material is selected from a group consisting of: silicone, epoxy, polyester resin, and a polymer; and
wherein the housing material comprises a metal is selected from a group consisting of: a metal alloy, stainless steel, tungsten carbide, a titanium alloy, silver, platinum and gold.

17. The wearable computing device of claim 14
wherein the first temperature sensor is selected from a group consisting of: a thermistor, a positive temperature coefficient thermistor, a negative temperature coefficient thermistor, and an infrared sensor.

18. The wearable computing device of claim 14 further comprising:
an external electromagnetic inducting charging mechanism configured to output a magnetic field;
wherein wearable computing device is removably coupled to the external electromagnetic inducting charging mechanism; and wherein the plurality of components also comprises an electromagnetic induction charging coil configured to be disposed proximate to the external electromagnetic inducting charging mechanism, wherein the electromagnetic induction charging coil is configured to receive the magnetic field in a direction normal to the interior surface of the external housing.

19. The wearable computing device of claim 14
wherein the short-range communication module is selected from a group consisting of near field communication (NFC), and Bluetooth; and
wherein the output data comprises authentication data associated with the client computing device.

20. The wearable computing device of claim 14
wherein the one or more sensors are configured to sense the physical perturbations at a first detection frequency or a second detection frequency; and
wherein the processor is configured to direct the one or more sensors to change detection frequency from the first detection frequency to the second detection frequency in response to the sensed data.

\* \* \* \* \*